(12) United States Patent
Jimenez et al.

(10) Patent No.: US 10,159,248 B2
(45) Date of Patent: *Dec. 25, 2018

(54) METHODS OF INHIBITING, PREVENTING, KILLING AND/OR REPELLING INSECTS USING SIMULATED BLENDS OF CHENOPODIUM

(71) Applicant: Bayer CropScience LP, Research Triangle Park, NC (US)

(72) Inventors: Desmond Jimenez, Woodland, CA (US); Giselle Janssen, Mountain View, CA (US); Dennis Long, Demorest, GA (US); Brett Highland, Nokomis, FL (US); Tara Lu, Davis, CA (US); Gerardo Bueno, Davis, CA (US); Nicholas Wright, N. Chesterfield, VA (US)

(73) Assignee: Bayer CropScience LP, Research Triangle Park, NC (US)

( * ) Notice: Subject to any disclaimer, the term of this patent is extended or adjusted under 35 U.S.C. 154(b) by 388 days.

This patent is subject to a terminal disclaimer.

(21) Appl. No.: 15/050,100

(22) Filed: Feb. 22, 2016

(65) Prior Publication Data

US 2016/0165882 A1    Jun. 16, 2016

Related U.S. Application Data

(63) Continuation of application No. 13/961,857, filed on Aug. 7, 2013, now Pat. No. 9,295,250, which is a continuation of application No. 12/815,274, filed on Jun. 14, 2010.

(60) Provisional application No. 61/329,020, filed on Apr. 28, 2010, provisional application No. 61/286,314, filed on Dec. 14, 2009, provisional application No. 61/256,257, filed on Oct. 29, 2009, provisional application No. 61/247,885, filed on Oct. 1, 2009, provisional application No. 61/246,872, filed on Sep. 29, 2009, provisional application No. 61/213,470, filed on Jun. 12, 2009.

(51) Int. Cl.
*A01N 27/00* (2006.01)
*A01N 25/02* (2006.01)
*A01N 25/24* (2006.01)

(52) U.S. Cl.
CPC ............. *A01N 27/00* (2013.01); *A01N 25/02* (2013.01); *A01N 25/24* (2013.01)

(58) Field of Classification Search
None
See application file for complete search history.

(56) References Cited

U.S. PATENT DOCUMENTS 9,295,250 B2 * 3/2016 Jimenez ................. A01N 27/00
2008/0075796 A1 * 3/2008 Enan ...................... A01N 27/00
424/731

* cited by examiner

*Primary Examiner* — Michael Barker
(74) *Attorney, Agent, or Firm* — Michelle L. Samonek

(57) ABSTRACT

The present invention provides natural and/or simulated, synthetic, synergistic pesticidal compositions comprising terpenes, such as extracts from *Chenopodium ambrosioides* near *ambrosioides*, or compositions based on those found in *Chenopodium ambrosioides* near *ambrosioides*. The present invention also provides methods of using said compositions to kill, inhibit, prevent and/or repel plant pests from contacting and/or damaging plants.

7 Claims, 13 Drawing Sheets

FIGURE 5

Contact LC50 Assay Against Beet Armyworm

- a-Terpinene
- Carrier
- d-Limonene
- p-Cymene
- C13

Control of Western Flower Thrips (*Frankliniella occidentalis*) on Peppers with C12 and C14. Hughson, CA Control of Melon Aphid Nymphs (*Aphis gossypii*) on Tomatoes with C12 and C14. Ripon, CA Control of Melon Aphid Adults (*Aphis gossypii*) on Tomatoes with C12 and C14. Ripon, CA Control of Two Spotted Spider Mite Eggs (*Tetranychus urticae*) on Cotton with C12 and C14, Hughson, CA Control of Two Spotted Spider Mite Nymphs (*Tetranychus urticae*) on Cotton with C12 and C14. Hughson, CA Control of Two Spotted Spider Mite Adults (*Tetranychus urticae*) on Cotton with C12 and C14. Hughson, CA

METHODS OF INHIBITING, PREVENTING, KILLING AND/OR REPELLING INSECTS USING SIMULATED BLENDS OF CHENOPODIUM

CROSS-REFERENCE TO RELATED APPLICATIONS

This application claims priority to and is a continuation of U.S. patent application Ser. No. 13/961,857, filed Aug. 7, 2013, which in turn claims priority to and is a continuation of U.S. patent application Ser. No. 12/815,274, filed Jun. 14, 2010, which in turn claims priority to U.S. Provisional Application No. 61/213,470, filed on Jun. 12, 2009, U.S. Provisional Application No. 61/246,872, filed on Sep. 29, 2009, U.S. Provisional Application No. 61/247,885, filed on Oct. 1, 2009, U.S. Provisional Application No. 61/256,257, filed on Oct. 29, 2009, U.S. Provisional Application No. 61/286,314, filed on Dec. 14, 2009, and U.S. Provisional Application No. 61/329,020, filed on Apr. 28, 2010. The contents of the aforementioned patent applications are hereby incorporated by reference into the present disclosure.

TECHNICAL FIELD

This invention relates to the technical field of formulation technology of plant protection agents and to methods of preparing and using such formulations.

BACKGROUND

The use of extracts obtained from *Chenopodium ambrosioides* for controlling established insect or mite infestations on plants has been described previously, including the use of such extracts that include natural terpenes isolated from *Chenopodium*. See, for example, US Published Patent Application Nos. 2003/0091657 and 2009/0030087; PCT Publication Nos. WO 2001/067868 and WO 2004/006679; William Quarles (1992) Botanical Pesticides from *Chenopodium*, The IPM Practitioner Volume XIV, Number 2, 11 pages; and Lorenzo Sagrero-Nieves (March/April 1995) Volatile Constituents from the Leaves of *Chenopodium ambrosioides* L., J. Essent. Oil Res. 7:221-223, each of which is specifically incorporated by reference herein in its entirety. The prior art teaches that such extracts can be applied to plants to kill or otherwise control certain insect species and/or mites on plants.

The prior art, however, does not appreciate that simulated blends comprising substantially pure terpenes can effectively mimic the insecticidal and acaricidal activity of the *Chenopodium* plant extracts. There is a long-standing need to substitute natural extract from plants with active substantially pure chemicals which can mimic the functions of the natural extract when mixed, due to limited availability of plant resources, variability in plant extract compositions, longer production cycle and higher cost of natural extract compared to synthetic chemicals. However, it has been always a challenge for researchers to identify the active ingredients in the natural extracts from plants, and even if such ingredients were identified, problems still remain: in some cases, such ingredients can not be synthesized through known pathways; in other cases, even if such ingredients could be synthesized, a mere combination of them may recapitulate no, or much lower, activity compared to the natural extract.

For example, despite the fact that Marinol (dronabinol) is the only US FDA-approved synthetic cannabinoid (chemical compound in natural *cannabis*), it typically provides only limited relief to select patients, particularly when compared to natural *cannabis* and its cannabinoids, since several other cannabinoids in *cannabis* may also contribute to the therapeutical effect, and synergism exists when these compounds are applied together.

For another example, it has been more and more accepted that synthetic crystalline vitamins differ from vitamins in natural products in many ways, since vitamins in natural products are complexes of critical combinations and cannot be split off without destroying the biological activities, while synthetic vitamins are only synthesized fractions of a vitamin complex.

For yet another example, in Jiang, Z., et al., "Comparative Toxicity of Essential Oils of *Litsea pungens* and *Litsea cubeba* and Blends of Their Major Constituents against the Cabbage Looper, *Trichoplusia ni*" J. Agric. Food Chem. (2009) 57, 4833-4837, the authors describe the extract of *L. cubeba*, which includes the major terpenes present in *Chenopodium*, α-terpinene, d-limonene and p-cymene, as well as other components. The Jiang reference notes that mortality caused by mixtures of the six known components of the extract was significantly lower than that caused by the natural essential oil, suggesting that the 10% of the unknown constituents had a significant contribution to toxicity. Further, a combination of γ-terpinene, R-limonene and p-cymene was only 40% effective against *Trichoplusia ni* and a combination containing α-terpinene, β-pinene and α-pinene had almost no mortality against *T. ni* larvae.

Beghyn et al., Natural Compounds: Leads or Ideas? Bioinspired Molecules for Drug Discovery, 28 Jun. 2008, Chemical Biology & Drug Design, 72(1):3-15, summarize the results of their review as follows: "In this article, we compare drugs of natural origin to synthetic compounds and analyze the reasons why natural compounds occupy a place of choice in the current pharmacopoeia." Thus, it is well known by those skilled in the art that the synthetic analog of a natural extract may have very different biological activities. This is particularly so where, as in the present invention, the extract contains more than one active ingredient.

U.S. Patent Application Publication Nos. 2008/0075796 and 2008/0020078 describe some synergistic combinations of plant oils for controlling insects. These publications provide long lists of essential oils, including selected terpenes, that may or may not be included in such compositions. These publications fail to provide specific guidance or examples that would lead one of ordinary skill in the art to arrive at the simulated, synthetic terpene compositions of the present invention or to use the simulated, synthetic terpene compositions of the present invention to control insects. For example, US Patent Application Publication No. 2008/0075796 describes a composition comprising d-limonene, α-pinene and p-cymene that is shown as being active against only farm ants. As demonstrated by the Jiang reference described above, it is not possible to simply combine various terpenes without testing specific combinations and amounts of such terpenes to arrive at insecticidally effective compositions.

Thus, the simulated, synthetic and synergistic pesticidal compositions of the present invention are not obvious over the prior art, since a person with ordinary skill in the art will not be able to predict the necessary active ingredients to be combined to make such pesticidal compositions and the synergistic pesticidal effects of the compositions.

In addition, the prior art does not appreciate that certain terpene extracts obtained from *Chenopodium ambrosioides*, natural analogs of such terpenes from other plant species or other organisms, and/or the synthetic versions of such terpenes can also be used in preventative or prophylactic methods of plant protection (i.e., applied to plants before the insects and/or mites reach the economic threshold on the plants). Furthermore, the prior art does not appreciate that such terpene extracts, natural analogs of such terpenes from other plant species or other organisms, and/or synthetic versions of such extracts, can be used to kill or otherwise control lepidopteran plant pests.

Furthermore, the prior art does not appreciate that such terpene extracts, natural analogs of such terpenes from other plant species or other organisms, and/or synthetic versions of such extracts, can be used to kill or otherwise control lepidopteran plant pests. While Highland et al. (Submitted Paper Abstracts, Entomological Society of America Eastern Branch 78th Annual Meeting, March 2007, Appendix F, page 55) provide some information showing that extracts obtained from *Chenopodium ambrosioides* can control sod webworms (when applied at rates that are at least 300 times the norm for the extracts) and spotted tentiform leafminers, it remained unappreciated until the present invention that such terpenes can control a wider variety of lepidopteran species when applied at lower rates under both field and greenhouse conditions.

SUMMARY

The present invention provides compositions comprising three terpenes, i.e. α-terpinene, p-cymene and limonene, as pesticidally active chemical compounds. The three terpenes in the compositions used in the present invention can be obtained from any source such as, for example, as an extract from *Chenopodium ambrosioides* near *ambrosioides*, or as an extract from another plant genus/species that produces such terpenes, or produced synthetically (i.e., by a chemical synthesis process), and/or as a compound produced naturally by any organism (i.e., as a compound separate from an extract per se). In one example, all three terpenes are from natural extracts obtained from *Chenopodium ambrosioides* near *ambrosioides*. In one example, all three terpenes are from natural analogs of such terpenes as extract from other plant species or other organisms. In still another example, all three terpenes are synthetic versions of the terpenes obtainable from *Chenopodium ambrosioides* near *ambrosioides* or other plant species or other organisms. In yet other examples, the three terpenes are any possible combination of natural and/or synthetic versions of the three terpenes. In yet another example, the three terpenes are obtained from any source or by any means except from an extract of *Chenopodium ambrosioides* or except from an extract of *Chenopodium*.

In one embodiment, the compositions comprise an excipient and pesticidally active compositions, such as extracts obtained from *Chenopodium ambrosioides*, or a simulated blend consisting essentially of α-terpinene, p-cymene and limonene not obtained from *Chenopodium ambrosioides* or not obtained from *Chenopodium*. In another embodiment, the compositions consist essentially of an excipient and extracts obtained from *Chenopodium ambrosioides*, or a simulated blend consisting essentially of α-terpinene, p-cymene and limonene. In a further embodiment, the compositions consist of an excipient and extracts obtained from *Chenopodium ambrosioides*, or a simulated blend consisting essentially of α-terpinene, p-cymene and limonene. In some embodiments, the compositions do not contain thymol, carvacol, carvone, carveol and/or nerol. In particular embodiments, the simulated blends in the above compositions are not from an extract of *Chenopodium ambrosioides* or from an extract of *Chenopodium*.

In one embodiment, the pesticidally active compositions of the present invention only include the essential oil extracts from or based on those found in *Chenopodium ambrosioides* near *ambrosioides*. In another embodiment, the pesticidally active compositions of the present invention only include a synthetic blend simulating the essential oil extract from or based on those found in *Chenopodium ambrosioides* near *ambrosioides*. In another embodiment, the pesticidally active compositions of the present invention include a mixture of the essential oil extract and the synthetic blend. In some embodiments, the compositions to be applied to plants as a protectant are "normalized" by adding specific amounts of synthetic versions of one or more of the terpene compounds found in the natural extract and/or synthetic terpenes so as to produce a composition with a set ratio of the three terpenes, such as the ratio observed in certain standardized or preferred natural extracts from or based on those found in *Chenopodium*. In still other embodiments, the compositions used in the methods of the present invention are reconstituted, as explained more herein.

In some embodiments, the simulated blends simulating the *Chenopodium* extract consist essentially of natural analogs of such terpenes from other plant species or other organisms, and/or the synthetic versions of such terpenes. In some embodiments, simulated blends comprise the three substantially pure α-terpinene, p-cymene and limonene, optionally with at least one volume filler that replaces the volume taken up by the minor components normally present in the extract of *Chenopodium ambrosioides* near *ambrosioides*. In some embodiments, the volume filler is vegetable oil or mineral oil. In further embodiments, the simulated blends consist essentially of α-terpinene, p-cymene and limonene, and an oil wherein the α-terpinene, p-cymene and limonene are substantially pure and are not obtained from a *Chenopodium* extract, and wherein the excipient is not an essential oil. In some embodiments, the limonene is prepared from citrus peels or pines by cold press method.

The concentration of α-terpinene in the compositions of the present invention, whether as an extract and/or a synthetic version, ranges from about 30% to about 70% by weight; the concentration of p-cymene in the compositions, whether as an extract and/or a synthetic version, ranges from about 10% to about 30% by weight, and the concentration of limonene in the compositions, whether as an extract and/or a synthetic version, ranges from about 1% to about 20% by weight.

In some embodiments, the concentration of α-terpinene in the compositions, whether as an extract and/or a synthetic version, ranges from about 35% to about 45% by weight; the concentration of p-cymene in the compositions, whether as an extract and/or a synthetic version, ranges from about 15% to about 25% by weight, and the concentration of limonene in the compositions, whether as an extract and/or a synthetic version, ranges from about 5% to about 15% by weight.

In some embodiments, the concentration of substantially pure α-terpinene in the compositions is about 39% by weight; the concentration of substantially pure p-cymene in the compositions is about 17% by weight, and the concentration of substantially pure limonene in the compositions is about 12% by weight.

In some embodiments, the absolute concentration of α-terpinene in the compositions is about 36% by weight; the absolute concentration of p-cymene in the compositions is about 14.9% by weight, and the absolute concentration of limonene in the compositions is about 11.4% by weight.

In some embodiments, the relative ratio among α-terpinene, p-cymene, and limonene in the compositions is about 35-45 α-terpinene to about 12-20 p-cymene to about 10-15 limonene. Other relative ratios are described in more detail below.

The present invention also provides biopesticidal compositions comprising the compositions of the present invention. The biopesticidal compositions can further comprise at least one vegetable oil as carrier or solvent, and/or at least one spreader/sticker. In some embodiments, the biopesticidal compositions further comprise one or more additional pesticidally active compounds against plant pests, wherein the additional pesticidally active compounds may be a carrier, a solvent or another pesticide, such as another insecticide, or biopesticide. Non-limiting examples of such additional pesticides which can be added to the compositions of the present invention include, one or more fungicides, insecticides, miticides or acaricides, bactericides and the like as well as combinations thereof. The biopesticidal compositions of the present invention also can further comprise at least one adjuvant to increase the effectiveness of the active ingredient. The adjuvant can be selected from the group consisting of spreaders-stickers, surface-active agents, e.g. emulsifiers and/or dispersing agents, penetrants, safeners, anticaking agents, and mixtures thereof. In some embodiments, adjuvants (e.g., solvents and/or carriers) added to the terpenes themselves act as pesticides. In one embodiment, the carrier/solvent is a hydrocarbon, for example, a vegetable oil, such as canola oil, methyl ester of soybean oil, or mixture of thereof. In one embodiment, the emulsifier is Tween™ 80.

The present invention also provides the formulation technologies for preparing such compositions of plant protecting agents. In one embodiment, the compositions of the present invention are formulated as emulsifiable concentrates (EC). In one embodiment, the formulation is a highly concentrated liquid. In another embodiment, the formulation is a spray concentrate. In another embodiment, the formulation is an ultra low volume (ULV) concentrate. In another embodiment, the formulation is a highly diluted liquid or oil solution. In still another embodiment, the formulation is in an encapsulated form.

The present invention also provides methods of using compositions of the present invention to inhibit, prevent, kill, and/or repel plant pests from contacting plants and/or feeding on plants so as to reduce or eliminate any kinds of damage to the plants caused by such plant pests, for example, such as the damage caused by said plant pests feeding of plants, or damages caused by viruses transmitted by the plant pests. In one embodiment, the compositions of the present invention are applied to plants before plant pests populations reach the economic threshold for a particular plant pest species and plant species combination. In one embodiment, the compositions of the present invention are applied to plants at any stage, before, during or after the plant pests populations reach the economic threshold for a particular plant pest species and plant species combination. For example, the application occurs at, during or after transplantation of the plant or emergence of the plant. In some embodiments, the compositions are applied one or more additional times during the life cycle of the plant.

The present invention also provides methods of using the compositions of the present invention to reduce or eliminate plant disease infection by plant pests by inhibiting, preventing, killing and/or repelling plant pests from contacting plants and/or feeding on plants, wherein the plant pests can carry or transmit one or more plant diseases. In one embodiment, the plant disease is a virus.

In some embodiments, the plant pests are insects and/or mites. In some embodiments, the insects are aphids or *thrips* or white flies or psyllids. In some embodiments, the insects are lepidopteran pests. In still another embodiment, the lepidopterans controlled by the present invention are any lepidopteran other than sod webworms and/or any webworm species, and/or spotted tentiform leafminers.

The methods of the present invention can be accomplished by applying to a plant or plant part or an area around a plant or plant part a composition that includes a simulated blend of an essential oil extract of *Chenopodium ambrosioides* near *ambrosioides* in which such simulated blend consists essentially of substantially pure α-terpinene, substantially pure p-cymene, and substantially pure limonene, wherein these substantially pure compounds are not obtained from a *Chenopodium* extract. The composition used in the above method may also comprise a carrier and/or volume filler, which may be an oil, such as a vegetable oil. In some embodiments, the carrier and/or volume filler may acts as a pesticide. In some embodiments, the carrier and/or volume filler act as an insecticide. In some embodiments, the composition does not contain thymol, carvacrol, carvone, carveol and/or nerol. In some embodiments the composition does not contain the aforementioned five essential oils and does not contain any other essential oils, except those other essential oils that are present as minor impurities in the substantially pure α-terpinene, p-cymene and limonene. In some embodiments, the composition does not contain essential oils other than α-terpinene, p-cymene and limonene.

The methods of the present invention include using the compositions of the present invention to inhibit, kill, prevent and/or repel plant pests from contacting the plants, wherein the inhibiting, killing, preventing and/or repelling of plant pests is effective for at least 1 day after application. In another embodiment, inhibiting, killing, preventing, and/or repelling of plant pests is effective at least 2 days after application. In yet another embodiment, the inhibiting, killing, preventing and/or repelling plant pests is effective for at least 3 days after application. In still another embodiment, the inhibiting, killing, preventing and/or repelling plant pests is effective for at least 1 week after application. In other embodiments, the inhibiting, killing, preventing and/or repelling plant pests is effective for more than 1 week after application (e.g., for at least 8 days, or at least 9 days, or at least 10 days or at least 11 days, or longer).

The methods of the present invention include applying the compositions of the present invention at any time during the life cycle of a plant, during one or more stages of a plant's life cycle, or at regular intervals of a plant's life cycle, or continuously throughout the life of the plant. By applying the compositions to plants before insect populations reach the economic threshold for a particular insect and plant species combination, the preventative, inhibitory and/or repelling effect of the extract compositions can be maintained for as long as desirable by repeated applications. For example, the compositions can be applied before, during and/or shortly after the plants are transplanted from one location to another, such as from a greenhouse or hotbed to the field. In another example, the compositions can be applied shortly after seedlings emerge from the soil or other growth media (e.g., vermiculite). In yet another example, the compositions can be applied at any time to plants grown hydroponically. The compositions can be applied at any desirable time but before the plant pests reach an economic threshold, as explained in more detail herein, or the compositions can be applied at any desirable time, during or after the plant pests reach an economic threshold.

The present invention encompasses (i) a method for preventing and/or reducing plant damage by insects and/or mites and/or (ii) a method for reducing or preventing disease transmission to the plant by disease-carrying insects and/or mites comprising applying to a plant or plant part and/or applying to an area around a plant or plant part a composition comprising α-terpinene, p-cymene and limonene, wherein the application occurs prior to the plant or plant part having an economic threshold of the insects and/or mites. In one embodiment the plant damage or disease transmission is caused by feeding of the insects and/or mites on the plant. In another embodiment the disease is a viral disease.

The methods of the present invention also include pretreatment of plants or plant parts with compositions of the present invention wherein such methods may be useful for quarantine purposes. Examples of such quarantine purposes include but are not limited to locations and situations where minimum residue levels or zero tolerance for pests, such as for exotic pests, may be important.

The present invention also provides methods of enhancing the inhibiting, preventing, killing, and/or repelling activity of the compositions described herein against plant pests by applying the compositions on plants for multiple times with desired interval period. In one embodiment, the interval period is about 1 hour, about 5 hours, about 10 hours, about 24 hours, about two days, about 3 days, about 4 days, about 5 days, about 1 week, about 10 days, about two weeks, about three weeks, about 1 month or more.

BRIEF DESCRIPTION OF THE DRAWINGS

FIG. 5 depicts the estimated $LC_{50s}$ when the samples were run as a nested set using probit analysis, calculating the slope, and the 95% confidence intervals.

DETAILED DESCRIPTION

Figure 1:
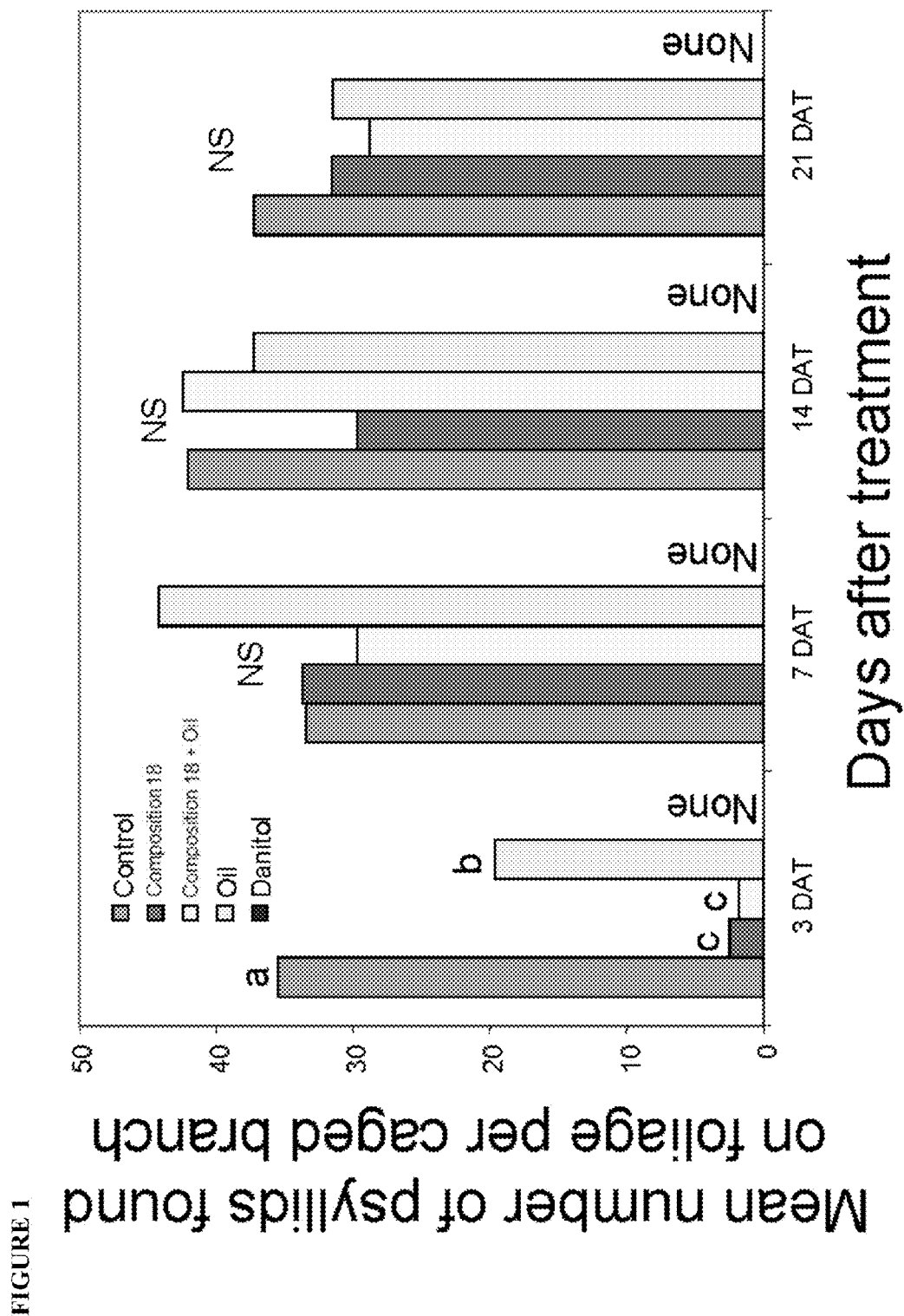
FIG. 1 represents psyllid repellency at 3 DAT, 7 DAT, 14 DAT and 21 DAT on untreated control plants, plants treated with Composition 18, Composition 18+citrus oil, citrus oil, and danitol.

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

DEFINITIONS

Unless defined otherwise, all technical and scientific terms used herein have the same meaning as commonly understood by one of ordinary skill in the art to which this invention belongs.

As used herein, the term "control" or "controlling" means to kill plant pests; or to inhibit the activity of plant pests (e.g., reduced mobility, appetite and/or reproductive capability); or to repel plant pests from a host or area.

As used herein, the phrase "active ingredient" refers to an ingredient of one chemical compound, or mixture of several chemical compounds, wherein the ingredient is pesticidally active.

An insecticidally effective amount of an active ingredient is an amount effective to control plant pests and/or to reduce plant damage. In some embodiments, control is 50% kill, inhibition and/or repellency of plant pests, in others, control is about 60%, in others about 70%, in others about 75%, in others about 80%, in others about 85%, in others about 90%; in others about 100%, compared to a host or area not treated with the active ingredient.

As used herein, the term "plant extract" refers to any substance obtained from plants. Plant extracts include but are not limited to aromatic substances, such as phenols or tannins, and alkaloids. Plant extracts are generally obtained from plants by removing the desired substance, usually an active ingredient, from a plant or plant part using a suitable solvent, which is evaporated away, and adjusting the residue to a desired amount, such as a desired or prescribed standard amount of the active substance.

As used herein, the phrase "normalized extract" refers to a composition formulated so that some or all of at least one of the active substances in a particular plant extract are derived from another source, either synthetic or natural.

As used herein, the phrase "simulated blend" refers to a composition assembled from synthetically produced compounds and/or compounds derived from one or more plant extracts, which simulates the activity of a plant extract, and in which no compound is obtained from the plant extract whose activity is being simulated.

As used herein, the phrase "essential oil extract" means the volatile, aromatic oils obtained by steam or hydrodistillation of plant material and may include, but are not restricted to, being primarily composed of terpenes and their oxygenated derivatives. Essential oils can be obtained from, for example, plant parts including, for example, flowers, leaves, seeds, roots, stems, bark, wood, and etc.

As used herein, the term "terpene" refers to a large and varied class of hydrocarbons, produced primarily by a wide variety of plants and by some insects. They are the major components of resin, and or turpentine produced from resin. They are the primary constituents of the essential oils of many types of plants and flowers.

As used herein, the term "penetrants" refers to chemical compounds that facilitate the transfer of biopesticide into the plant tissues. They can be lipids or detergent (also called surfactant), including but not limited to heavy petroleum oils and distillates, polyol fatty acid esters, polyethoxylated fatty acid esters, polyhydric alcohols, and alkyl phosphates.

As used herein, the term "safeners" refers to substances added to mixtures of pesticides to limit the formation of undesirable reaction products, e.g. alcohol sulfates, sodium alkyl butane diamate, polyesters of sodium thiobutane dioate, and benzene acetonitrile derivatives.

As used herein, the term "partially purified" means that the extract is in a form that is relatively free of proteins, nucleic acids, lipids, carbohydrates or other materials naturally associated in a plant.

As used herein, the term "substantially pure" means that a compound or a combination of compounds contains minor amounts of other compounds. In one aspect, substantially pure compounds are made synthetically and separated from their starting materials and/or other byproducts. In another aspect, a substantially pure compound(s) of interest (i.e., a target compound(s)) is isolated from an organism, such as a plant or a microorganism, such that the isolated compound or compounds only contain minor amounts of non-target compounds. In one embodiment, a substantially pure compound contains less than or equal to about 10% other compounds; in another less than or equal to about 9% other compounds; in another less than or equal to about 8% other compounds; in another less than or equal to about 7% other compounds; in another less than or equal to about 6% other compounds; in another less than or equal to about 5% other compounds; in another less than or equal to about 4% other compounds; in another less than or equal to about 3% other compounds; in another less than or equal to about 2% other compounds; in another less than or equal to about 1% other compounds; and in another less than or equal to about 0.5% other compounds.

As used herein, the term "emulsifier" refers to a substance which stabilises an emulsion, e.g. a surfactant.

As used herein, the term "surfactant" refers to a substance which serves as a wetting agent that lowers the surface tension of a liquid, allowing easier spreading, and lowers the interfacial tension between two liquids.

As used herein, the term "spreader/binder", or "spreader-sticker" refers to a substance which improves the performance of many biopesticides/pesticides by making them more resistant to rewetting and run off caused by rain and irrigation water.

As used herein, the term "Tween™" refers to a group of polysorbate surfactant whose stability and relative non-toxicity allows it to be used as a detergent and emulsifier in number of domestic, scientific, pharmacological, agricultural applications. It is a polyoxyethylene derivative of sorbitan monolaurate, and is distinguished by length of the polyoxyethylene chain and the fatty acid ester moiety. For example, Tween™ 20 (a. k. a. polysorbate 20) is a chemical compound having the following structure:

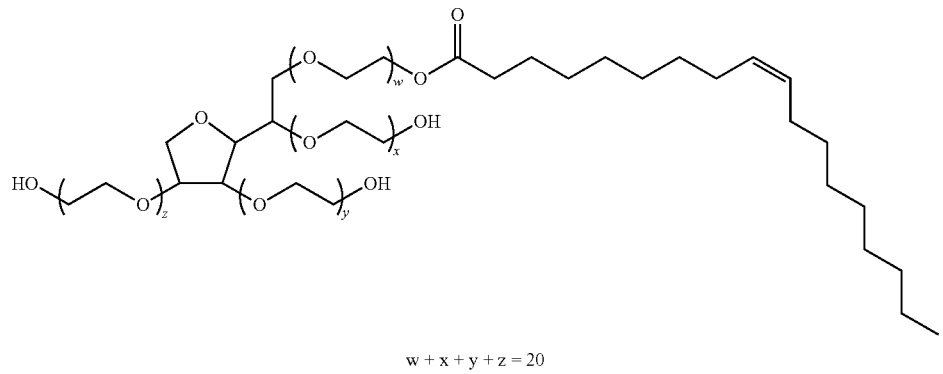

$w + x + y + z = 20$

As used herein, the phrase "insect repellent" refers to a substance applied to plant which discourages one or more insects (and arthropods in general) from contacting a plant, such as landing, climbing, or feeding on that plant.

As used herein, the phrase "economic threshold" refers to the density of a pest at which a control treatment by conventional pesticide use will provide an economic return. Thus, the economic threshold for insects refers to the timing for applying a pesticide which is based on the number of insects per plant, per plant part or per defined geographical area, such as the number of a particular insect per acre or per hectare. The number of insects can be determined visually or by any other suitable method, such as but not limited to inspection of the plant or part using a microscope or other suitable instrument. The insect density can be based on the number of whole insects, insect eggs, insect parts, insect damage, or by any other suitable method and combinations of all such methods. The insect density considered to be the economic threshold for a particular insect on a particular plant species varies depending on the factors such as the particular insect species, plant species, plant parts, plant development stage, commodity prices for the crop and the relative cost of pesticide and application.

As used herein, the verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "solvent" or "carrier" refers to a liquid or gas, or a mixture of two or more types of liquid or gas, that dissolve solid, liquid, or gaseous solute, resulting in a solution. The most common solvent is water. Most other commonly-used solvents are organic (carbon-containing) chemicals.

As used herein, the phrase "emulsifiable concentrate" refers to a liquid formulation in which the active ingredient(s) has been dissolved in oil or other solvents and an emulsifier has been added so that the formulation can be mixed with water or oil for spraying.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, brassica leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other brassica leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of cucumis melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberryies, gooseberries, honeysuckles, mayapples, nannyberries, Oregongrapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fibber crops (e.g. hemp, cotton), ornamentals, and the like.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, fruit and the like. The two main parts of plants grown in some sort of media, such as soil, are often referred to as the "above-ground" part, also often referred to as the "shoots", and the "below-ground" part, also often referred to as the "roots".

The compositions and methods of the present invention can be applied to any plant or any part of any plant grown in any type of media used to grow plants (e.g., soil, vermiculite, shredded cardboard, and water) or applied to plants or the parts of plants grown aerially, such as orchids or staghorn ferns. Such treatment can be for any purpose for inhibiting, killing, preventing and/or repelling any plant pathogen, including as a prophylactic (i.e., preventative) treatment or in reducing or eliminating the presence of a plant pathogen on a plant. The presence of the plant pathogen may be non-infective or infective, or invasive or non-invasive, either before or during application of the compositions of the present invention.

The present invention provides biopesticidal compositions and methods of using such compositions for the effective control of many plant pest species and types. For example, in some embodiments, the compositions and methods of the present invention can be used to control one or more of the following insects: psyllids, *thrips*, leafhoppers, leaf miners, Lepidopterans, mites, two-spotted spider mites, and whiteflies. In some embodiments, the insects controlled by the compositions and methods of the present invention do not include one or more of the following insects: ants, such as red ants and farm ants.

Plant Insect Pests

Agricultural insect pests can be classified into: chewing insects, sucking insects, and soil insects. Common chewing insects are, for example, beet armyworm (*Spodoptera exigua*), diamondback moth (*Plutella xylostella*), corn earworm (*Heliothis zea*, a.k.a. bollworm and tomato fruitworm), blister beetles (Epicauta and others), carrot weevils (*Listronotus oregonensis, Hyperodes texana*), cabbage looper (*Trichopulsia ni*), grasshopper (several species), flea beetles (e.g., tobacco fleabeetle (*Epitrix hirtipennis*), eggplant fleabeetle (*E. fuscula*), potato fleabeetle (*E. cucumeri*) and other species), fall armyworm (*Spodoptera frugiperda*), Lesser cornstalk borer (*Elasmopalpus lignosellus*), Texas leafcutting ant (*Atta texana*), citrus leafminer (*Phyllocnistis citrella*), leafminers (*Liiriomyza* spp.), yellowstriped armyworm (*Spodoptera ornithogalli*). Common sucking insects are, for example, stink bugs (e.g. *Nezara viridula* and other species), sharpshooters (*Homalodisca* spp. and *Oncopmetopia* spp.), whiteflies (e.g. sliverleaf whitefly, greenhouse whitefly, sweetpotato whitefly (*Bemisia tabaci*)), greenhouse whitefly (*Trialeuroides vaporariorum*), psyllid (e.g. Asian citrus psyllid), squash bug (*Anasa tristis*), leaffooted bugs (*Leptoglossus* spp.), leafhoppers (e.g., bean leafhopper, *Empoasca solana*, aster leafhopper, *Macrosteles fascifrons*, western potato leafhopper, *Empoasca abrupta*, grape leafhopper, variegated leafhopper, beet leafhopper, *Circulifer tenellus*), aphids (*Aphidoidea*, e.g. green peach aphid, turnip aphid, melon aphid, potato aphid, rosy apple aphid, spirea aphid,). Common rasping insects include, but are not limited to, *thrips* (e.g. citrus *thrips*, western flower *thrips* (*Frankliniella occidentalis*), onion *thrips* (*Thrips tabaci*), melon *thrips*, chili *thrips*). Common soil insects are, for example, granulate cutworm (*Feltia subterranea*), mole crickets (e.g. northern mole cricket, *Neocurtilla hexadactyla*, southern molre cricket *Scapteriscus acletus*), corn rootworm (e.g. *Diabrotica undecimpunctata howardi*), pillbugs and sowbugs (several species), sweetpotato weevil (*Cylas formicarius elegantulus*), white grubs (*Pyllophaga* spp.), wireworms (several species).

In addition, most of the plant viral diseases are transmitted through the agency of different insects or mites. Both chewing and sucking insects and/or mites are capable of transmitting viral diseases. The transmission may be simply mechanical or may be biological. In the latter case the specific insect and the specific viral pathogen have some kind of association or relationship. In such case, insects are called the "vector" for particular viral pathogen. In case of mechanical transmission the pathogen is simply carried externally or internally by insects. Virus carried biologically by insect vectors are of two types: non-persistent viral pathogen, wherein the viral pathogens require no latent or incubation period in the insect body, and persistent viral pathogen, wherein viral pathogens requiring certain incubation period inside the vector body before they are inoculated or transmitted to healthy host. The insects responsible for transmission of viral diseases are, for example, aphids, jassids (leaf hoppers), psyllids, whiteflies, mealy bugs, etc.

Besides viral pathogens, insects are also responsible for the transmission of many other bacterial and fungal plant pathogens. Non-limiting examples of plant pathogens transmitted by insects are, beet leafcurl virus, sugarbeet savoy virus, and beet latent rosette disease transmitted by ash-gray leaf bugs in the genus *Piesma*; over 150 different kinds of plant viruses (e.g., beet mosaic, cabbage black ringspot, carnation latent, cauliflower mosaic, cherry ringspot, cucumber mosaic, onion yellow dwarf, pea wilt, potato Y, tobacco etch, tobacco mosaic, tomato spotted wilt, and turnip yellow mosaic) transmitted by *Aphidoidea*; over 80 known types of plant disease (e.g., *mycoplasma*-like organisms (MLOs), spiroplasmas, aster yellows, beet curly top, blueberry stunt, dwarf disease of rice, phony peach, and Pierce's disease of grapes) transmitted by Leafhoppers (family Cicadellidae); over 20 plant diseases (e.g., cereal tillering disease, maize mosaic, Northern cereal mosaic, oat sterile dwarf, rice hoja blanca, rice stripe, and sugarcane Fiji disease) transmitted by superfamily Fulgoroidea; yellow mosaic diseases in at least 20 plant species including cowpeas, roses, soybeans, and tomatoes, and leaf curl viruses in cotton, potato, tomato, tobacco, and other plants, which are transmitted by whiteflies (family Aleyrodidae); viral pathogen that causes pseudo-curly top disease in eggplants and other Solanaceae, transmitted by treehoppers (family Membracidae); several plant viruses (e.g., cocoa swollen shoot virus and cocoa mottle leaf virus) transmitted by mealybugs (family Pseudococcidae); *mycoplasma*-like organisms responsible for pear decline and greening disease of citrus, transmitted by psyllids (family Psyllidae); viral pathogens (e.g., tomato spotted wilt virus and squash vein yellowing virus) transmitted by *thrips* or whiteflies, such as the silverleaf whitefly (respectively); tobacco mosaic virus and sowbane mosaic virus transmitted by leafminer flies (family Agromyzidae) in the genus *Liriomyza*; more than 35 plant viruses (e.g., broad bean mottle, turnip yellow mosaic, southern bean mosaic, and rice yellow mottle) transmitted by leaf beetles (family Chrysomelidae); fungal pathogens in trees transmitted by bark beetles (family Scolytidae); *Ceratocystis ulmi* (pathogen of Dutch elm disease) transmitted by elm bark beetle (*Scolytus multistriatus*); blue stain fungus (*Ceratocystis ips*) transmitted by pine engraver (*Ips pini*) and other bark beetles; *Endothia parasitica* (pathogen of chestnut blight) transmitted by Scolytidae; *Sclerotinia fructicola* (fungal pathogen of brown rot) transmitted by Plum curculio, *Conotrachelus nenuphar* (family Curculionidae); *Erwinia amylovora* (bacterial pathogen of fire blight) transmitted by honey bees, *Apis mellifera* (family Apidae) and other pollinating insects; and blueberry fungus (pathogens for mummy berry) transmitted by ants (family Formicidae) and bees, tobacco mosaic virus transmitted by butterfly caterpillars (Lepidoptera). More examples are described in Leach, *Insect Transmission of Plant Disease*, 2007, Daya Publishing House, ISBN 8176220051, 9788176220057, which is incorporated by reference herein by its entirety for all purposes.

Common insect and mite pests in North America include, but are not limited to, Heteroptera Cicadellidae (e.g., White Apple Leafhopper, *Typhlocyba pomaria*, Rose Leafhopper, *Edwardsiana rosae*, Potato Leafhopper, *Empoasca fabae*), Heteroptera, Miridae, (e.g., Tarnished Plant Bug, *Lygus lineolaris*, Mullein Bug, *Campylomma verbasci*), Hemiptera, Diaspididae (e.g., San Jose Scale, *Quadraspidiotus perniciosus*), Hemiptera, Aphididae (Apple grain aphid, *Rhopalosiphum fitchii*, Rosy apple aphid, *Dysaphis plantaginea*, Woolly apple aphid, *Eriosoma lanigerum*), Hymenoptera, Tenthredinidae (e.g., European Apple Sawfly, *Hoplocampa*, and *testudinea*), Thysanoptera, Thripidae (e.g., Pear Thrips, *Taeniothrips inconsequens*), Diptera, Tephritidae (e.g., Apple maggot, *Rhagoletis pomonella*), Coleoptera, Curculionidae (e.g., *Plum curculio, Conotrachelus nenuphar*), Coleoptera, Scarabaeidae (e.g., Japanese Beetle, *Popilia japonica*), Coleoptera, Buprestidae (e.g., Flatheaded apple tree borer, *Chrysobothris femorata*), Coleoptera, Cerambycidae (e.g., Roundheaded apple tree borer, *Saperda candida*), Acari, Tetranychidae (e.g., European Red Mite, *Panonychus ulmi*, Twospotted Spider Mite, *Tetranychus urticae*), Heteroptera, Miridae (e.g., Mullein Bug, *Campylomma verbasci*), Heteroptera, Rhopalidae (e.g., Western box-elder bug, *Leptocoris rubrolineatus*), Heteroptera, Pentatomidae (e.g., Consperse stink bug, *Euschistus conspersus*, Conchuela stink bug, *Chlorochroa ligata*), Hemiptera, Diaspididae (e.g., San Jose Scale, *Quadraspidiotus perniciosus*), and Hemiptera, Aphididae (e.g., Green apple aphid, *Aphis pomi*, Rosy apple aphid, *Dysaphis plantaginea*, and Woolly apple aphid, *Eriosoma lanigerum*).

Lepidopterans

Lepidopterans present a continuous and serious threat to plant growth, health and production throughout the United States and the world. Typical examples of lepidopteran pests in the eastern United States include, but are not limited to, Tortricidae (e.g, Codling Moth (*Cydia pomonella*), Oriental Fruit Moth (*Cydia molesta*), Lesser Appleworm (*Grapholita prunivora*), Tufted apple bud moth (*Platynota idaeusalis*), Oblique banded leafroller (*Choristoneura rosaceana*), Redbanded leafroller (*Argyrotaenia velutinana*)), Cossidae (e.g., Leopard moth (*Zeuzera pyrina*)), Agonoxenidae (e.g., Apple Pith Moth (*Blastodacna atra*), Sesiidae (e.g., Dogwood borer (*Synanthedon scitula*), Apple bark borer (*Synanthedon pyri*)), Noctuidae (e.g, Green Fruitworm (*Orthosia hibisci*)), Geometridae (e.g., Green Pug Moth (*Chloroclystis rectangulata*)), Lymantriidae (e.g., Gypsy Moth, (*Lymantria dispar*)), Gracillariidae (e.g., Apple Blotch Leafminer (*Phyllonorycter crataegella*), Spotted Tentiform Leafminer (*Phyllonorycter blancardella*)), and Lyonetidae (e.g., Apple Leafminer (*Lyonetia prunifoliella*)). Typical lepidopteran pets in western United States include, but are not limited to, Tortricidae (e.g., Codling Moth (*Cydia pomonella*)), Oriental Fruit Moth (*Cydia molesta*), Lesser Appleworm (*Gra-

*pholita prunivora*), Oblique banded leafroller (*Choristoneura rosaceana*), Redbanded leafroller (*Argyrotaenia velutinana*)), Noctuidae (e.g., *Lacanobia* fruitworm (*Lacanobia subjuncta*), and Gracillariidae (e.g., Western Tentiform Leafminer (*Phyllonorycter elmaella*)).

More lepidopterans are described by Kristensen (*Lepidoptera, moths and butterflies*, Volume 4, Part 35 of Handbuch der Zoologie, Publisher: Walter de Gruyter, 1999, ISBN 3110157047, 9783110157048), Scoble (*The Lepidoptera: Form, Function and Diversity*, Publisher: Oxford University Press, 1995, ISBN 0198549520, 9780198549529), and Wells et al. (*Lepidoptera: Hesperioidea, Papilionoidea*, Volume 31 of Zoological catalogue of Australia, Publisher: CSIRO Publishing, 2001, ISBN 0643067000, 9780643067004). All publications are incorporated by reference herein by their entireties for all purposes.

Leaf Miners

Leaf miners are insects, the larva of which tunnels inside of leaves or other plant parts. Only some lepidopterans are also known as leaf miners. The most commonly seen leaf miners are the larvae of several different families of small moths, which usually infest trees and plants used for landscaping. Leaf-mining moths belong to the families Coleophoridae, Cosmopterigidae, Gracillariidae, Heliozelidae, and Lyonetiidae. On vegetables, the most common leafminers are the larvae of small flies in the genus *Liriomyza*, including the vegetable leaf miners, the serpentine leaf miners, and the pea leaf miners.

Thus, in one embodiment, the present invention provides methods of using blends of natural and/or synthetic terpene compounds from or based on those found in *Chenopodium ambrosioides* near *ambrosioides* to kill and/or inhibit and/or repel lepidopterans that are not spotted tentiform leaf miners.

Plant Mite Pests

Mites, a.k.a., ticks, belong to subclass Acarina (or Acari) and the class Arachnida. Many live freely in the soil or water, but there are also a large number of species that live as parasites on plants, animals, and some that feed on mold. Some of the plant mite parasites are spider mites (family Tetranychidae), thread-footed mites (family Tarsonemidae), and the gall mites (family Eriophyidae). For example, plant mite parasites include, but are not limited to, two-spotted spider mite (e.g., *Tetranychus urticae, Tetranychus marianae, Oligonychus* spp. and others species); Kanzawa spider mite (e.g., *Tetranychus kanzawai*); citrus red mite (e.g., *Panonychus citri*); European red mite (e.g., *Panonychus ulmi*), yellow spider mite (e.g., *Eotetranychus carpini*); Texas citrus mite (e.g., *Eotetranychus banksi*); citrus rust mite (e.g., *Phyllocoptruta oleivora*); broad mite (e.g., *Polyphagotarsonemus latus*); false spider mite (e.g., *Brevipalpus* sp.); bulb mite (e.g., *Rhizoglyphus robini*) and mold mite (e.g., *Tyrophagus putrescentiae*); strawberry spider mite; pacific mite; willamette spider mite; six-spotted spider mite; citrus red mite and citrus rust mite. More plant mite parasites can be found in Ellis et al. (Ellis et al., *The organic gardener's handbook of natural insect and disease control*, Published by Rodale, 1996, ISBN 0875867531, 9780875967530).

Leafhoppers

Leafhopper is a common name applied to any species from the family Cicadellidae. Leafhoppers, colloquially known as "hoppers", are plant-feeding insects in the superfamily Membracoidea in the order Hemiptera. Non-limiting examples of leafhoppers families include, Acostemminae, Agalliinae, Aphrodinae, Arrugadinae, Austroagalloidinae, Bythoniinae, Cicadellinae (e.g., *Bothrogonia, Graphocephala, Homalodisca*, and *Zyzzogeton*), Coelidiinae, Deltocephalinae (e.g., *Circulifer, Graminella, Hecalusina*), Errhomeninae, Euacanthellinae, Eupelicinae, Eurymelinae (e.g., *Eurymela, Eurymeloides*), Euscelinae, Evacanthinae, Evansiolinae, Gyponinae, Hylicinae, Iassinae, Idiocerinae (e.g., *Idiocerus*), Ledrinae (e.g., *Neotituria*), Macropsinae, Makilingiinae, Megophthalminae, Mileewinae, Mukariinae, Neobalinae, Neocoelidiinae, Neopsinae, Nioniinae, Nirvaninae (e.g., *Nirvana* and *Sophonia*), Phereurhininae, Selenocephalinae, Signoretiinae, Stegelytrinae (e.g., *Aculescutellaris, Cyrta, Doda, Paracyrta*, and *Pseudododa*), Tartessinae, Tinterominae, Typhlocybinae (e.g., *Dziwneono, Empoasca, Erasmoneura, Eupteryx*, and *Typhlocyba*), and Xestocephalinae.

Psyllids

Psyllids (a.k.a. jumping plant lice) are small plant-feeding insects that tend to be very host specific, i.e. they only feed on one plant species (monophagous) or feed on a few related plants (oligophagous). The present restricted definition still includes 71 genera in the Psyllidae, including *Acizzia, Agonoscena, Allocaridara, Arytainilla, Bactericera, Blastopsylla, Boreioglycaspis, Cacopsylla, Ceropsylla, Cryptoneossa, Ctenarytaina, Diaphorina, Eucalyptolyma, Euphyllura, Glycaspis, Heteropsylla, Mycopsylla, Pachypsylla, Phylloplecta, Prosopidopsylla, Psylla, Psyllopsis, Retroacizzia, Tetragonocephela*, and others.

*Thrips*

*Thrips* (Order Thysanoptera) are tiny, slender insects with fringed wings. Other common names for *thrips* include thunderflies, thunderbugs, storm flies, and corn lice. *Thrips* species feed on a large variety of sources both plant and animal by puncturing them and sucking up the contents. A large number of *thrips* species are pests of commercial crops due to the damage caused by feeding on developing flowers or vegetables which causes discoloration, deformities, and reduced marketability of the crop. So far around 5,000 species have been described. Non-limiting examples of *thrips* family include, Adiheterothripidae, Aeolothripidae, Fauriellidae, Hemithripidae, Heterothripidae, Jezzinothripidae, Karataothripidae, Melanthripidae, Merothripidae, Phlaeothripidae, Scudderothripidae, Stenurothripidae, Thripidae, Triassothripidae, and Uzelothripidae.

Plant Insect Repellents

An insect repellent is different from an insecticide per se. Insect repellent is a substance applied to surfaces of a plant which discourages insects from landing, climbing, or feeding on the plant, while insecticide is a pesticide used against insects in all development forms by killing, damaging, or inhibiting growth after they have made contact with the plant. For example, pymetrozine or flonicamid/Beleaf are categorized as insecticides since they act directly on the insect to disrupt its physiology and prevent feeding. In some cases insecticides can even worsen virus transmission since the insects, e.g., aphids, keep probing and trying to feed.

Insect repellent is applied to the plant before the emergence or appearance of insects, or after the emergence or appearance of insects but before the insect density reaches economic threshold, while insecticide is applied after the emergence or appearance of insects, preferably after the insect density reaches the economic threshold for a particular insect species and a particular plant species.

Insect repellents include compounds that disrupt the normal feeding cycle rather than just making the plants or plant parts distasteful. While not wishing to be bound by any particular theory, it is believed that the methods of the present invention involve using compositions containing natural terpene extracts from or based on those found in

*Chenopodium ambrosioides* near *ambrosioides* and/or synthetic versions of such extracts wherein such compositions make the plant distasteful to the potential insect and/or mite pest.

Commonly used plant insect repellents include, but are not limited to 2-ethyl-1,3-hexanediol; N-octyl bicycloheptene dicarboximide; N,N-diethyl-M-toluamide; 2,3:4,5-Bis(2-butylene) tetrahydro-2-furaldehyde; Di-n-propyl isocinchomeronate; 2-hydroxyethyl-n-octyl sulfide; N-(cyanomethyl)-4-(trifluoromethyl)-3-pyridine-carboxamide (e.g. Flonicamid, FMC BELEAF™® 50 SG INSECTICIDE); and pymetrozine (e.g. Fulfill®). More plant insect repellents are described in U.S. Pat. Nos. 4,769,242, 4,869,896, 4,943,563, 5,221,535, 5,372,817, 5,429,817, 5,559,078, 5,591,435, 5,661,181, 5,674,517, 5,711,953, 5,756,113, 6,559,175, 6,646,011, 6,844,369, 6,949,680, 7,381,431, 7,425,595, each of which is incorporated by reference in its entirety herein, including all drawings/photographs that are a part thereof.

Thus, the present invention provides methods of using compositions comprising terpenes extract of *Chenopodium ambrosioides* near *ambrosioides*, natural analogs of such terpenes from other plant species or other organisms, and/or simulated blends of terpenes inspired by the extract of *Chenopodium*, to inhibit, prevent, kill and/or repel insect and/or mite contact of plants and/or feeding on plants so as to reduce or eliminate any kind of damage to the plants caused by such insect and/or contact, such as the damage caused by plant pests feeding of plants. In one embodiment, the blends based on those found in *Chenopodium ambrosioides* can be applied to plants with at least a second insect repellents as described herein, in combination (e.g., in mixture, and/or in subsequence), and/or in rotation.

Compositions of the Present Invention

The present invention provides a pesticidal composition comprising at least one active ingredient.

In one embodiment, the pesticidal composition further comprises at least one carrier/solvent.

In one embodiment, the pesticidal composition further comprises at least one carrier/solvent, at least one adjuvant, wherein the adjuvant is selected from the group consisting of emulsifier, spreader/binder, penetrants, safeners, anticaking agents, and mixture of thereof.

The active ingredient in the present invention at least comprises three terpenes, α-terpinene, p-cymene and limonene. The three terpenes in the compositions used in the present invention can be obtained from any source such as, for example, as an extract from *Chenopodium ambrosioides* near *ambrosioides*, which extract has insecticidal and acaricidal activity, as described in detail in US Published Patent Application Nos. 2003/0091657 and 2009/0030087; PCT Publication Nos. WO 2001/067868 and WO 2004/006679, or as an extract from another plant genus/species that produces such terpenes, or as a compound produced naturally by any organism (i.e., as a compound separate from an extract per se), or produced synthetically (i.e., by a chemical synthesis process). For example, the three terpenes can be from natural extracts obtained from *Chenopodium ambrosioides* near *ambrosioides*, natural analogs of such terpenes as extract from other plant species or other organisms, or synthetic versions of the terpenes, or combination thereof. Thus in one embodiment, the active ingredient in the present invention is the essential oil extract of *Chenopodium ambrosioides* near *ambrosioides*. In another embodiment, the active ingredient is a simulated blend simulating the essential oil extract of *Chenopodium ambrosioides* near *ambrosioides*. In still another example, the active ingredient is a combination of the essential oil extract of *Chenopodium ambrosioides* near *ambrosioides* and the simulated blend.

*Chenopodium ambrosioides* near *ambrosioides* plants, methods of preparing, harvesting and storage of such plants, methods of extracting essential oil, and composition of said essential oil, have been described elsewhere. See, for example, US Published Patent Application Nos. 2003/0091657 and 2009/0030087; PCT Publication Nos. WO 2001/067868 and WO 2004/006679; and Lorenzo Sagrero-Nieves (March/April 1995) Volatile Constituents from the Leaves of *Chenopodium ambrosioides* L., J. Essent. Oil Res. 7:221-223, each of which is incorporated by reference in its entirety herein, including all drawings/photographs that are a part thereof. The three biopesticidally active chemical compounds in the extract are α-terpinene, p-cymene and limonene.

The essential oil extract of *Chenopodium ambrosioides* near *ambrosioides* consists mainly of α-terpinene, p-cymene, limonene, and of other minor terpene constituents, which may include carvacrol, L-carveol (43% cis+54% trans), thymol, and γ-terpinene, which are pesticidal and are present at low levels. Example II of PCT Publication No. WO 2004/006679 notes that these minor components are likely to have a much greater impact on the activity of the oil than the major components. Applicants, however, have discovered that the three pesticidally active chemical compounds in the essential oil extract are α-terpinene, p-cymene and limonene and that the minor components are not necessary for activity. Any enantiomer of limonene will work in the methods of the present invention, including but not limited to d-limonene.

Essential oil extracts of *Chenopodium ambrosioides* may contain substantial quantities of the bicyclic monoterpene ascaridole, depending on the cultivar and the growing conditions. Because of concerns over mammalian toxicity of this compound, it is desirable to reduce or eliminate ascaridole from this preparation since this product for worker safety and to minimize ingestion of the compound after application of the product to fruits, vegetables or grains. The *C. ambrosioides* near *ambrosioides* cultivar was originally selected for its relatively low levels of ascaridole. In addition, as ascaridole can be physically removed or chemically converted to another product. Processes for physical removal include molecular distillation or supercritical $CO_2$ extraction. These methods lead to a near quantitative extraction of ascaridole from the essential oil. Chemical reduction methods have also been employed to convert ascaridole to the corresponding and relatively non-toxic 2,3 cis diol.

An entirely different strategy to eliminate ascaridole is to reconstitute the essential oil from other terpene sources, either natural or synthetic.

In one example, the concentration of α-terpinene in the extract of *Chenopodium ambrosioides* ranges from about 35% to about 45%, by weight. The concentration of p-cymene in the extract of *Chenopodium ambrosioides* ranges from about 15% to about 25%, by weight. The concentration of limonene in the extract of *Chenopodium ambrosioides* ranges from about 5% to about 15%, by weight. The concentration of minor terpene constituents and impurities in the extract of *Chenopodium ambrosioides* ranges from about 25% to about 35%, by weight. For a non-limiting example, in one extract, the concentrations (by weight) are as follows: 39% α-terpinene, 17% p-cymene, 12% limonene and 32% minor terpene constituents and impurities, by weight.

The concentration of the essential oil extract in the composition to be applied to plants and plant parts, depending on whether it is in the concentrated or diluted (ready-to-spray) form, can be at least about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, by weight.

For example, in some embodiments the final concentration of the extract in the composition to be applied to plants is about 0.05%, or about 0.1%, or about 0.2% or about 0.7%, by weight.

The present invention also provides compositions of simulated terpene blends which simulate the essential oil extract of *Chenopodium ambrosioides* near *ambrosioides*. The simulated terpene blends of the present invention comprise α-terpinene, p-cymene, and limonene at concentrations that are the same or about the same as their respective concentrations in extracts of *Chenopodium ambrosioides* near *ambrosioides*, wherein such extracts include additional minor terpene ingredients and impurities not present in the simulated blends of the present invention. Greenhouse and field testing unexpectedly demonstrates that there are no material differences in performance and/or plant safety between the simulated terpene blends of the present invention and the extract of *Chenopodium ambrosioides* near *ambrosioides* when used at the same rates or at about the same rates. The present invention provides for the first time a simulated blend of three terpenes that successfully mimics the pesticidal/insecticidal effects of extracts of *Chenopodium ambrosioides* near *ambrosioides*.

The simulated terpene blend of the present invention only comprises three pesticidally active terpene compounds (α-terpinene, p-cymene, and limonene) that when combined with inerts (carrier/solvent, emulsifier, and/or spreader/binder) are sufficient to mimic the pesticidal effects of the extract of *Chenopodium ambrosioides* near *ambrosioides*. Thus, the terpene blends of the present invention do not contain the minor terpene ingredients and impurities found in the *Chenopodium ambrosioides* near *ambrosioides* extract, such as thymol, carvacrol, carvone, carveol and/or nerol, wherein one or more of such minor terpenes may have insecticidal activity. In one embodiment, the simulated blend does not contain thymol, carvacrol, carvone, carveol and/or nerol. In one embodiment, the terpenes of the simulated terpene blend are not obtained from *Chenopodium ambrosiodes*. In another embodiment, they are not obtained from *Chenopodium*.

Simulated blends simulating the *Chenopodium* extract can be made according to the present invention by mixing together three substantially pure pesticidally active chemical compounds, α-terpinene, p-cymene and limonene, optionally with at least one volume filler, for example, vegetable oil (e.g. food grade), or mineral oil that replaces the volume taken up by the minor components normally present in the extract.

As used herein, the term "vegetable oil" refers to lipid materials derived from plants, which do not contain, or only contain trace amount of fragrances or essential oils, such that the materials are non-volatile, non-scented plant oils. Thus, as used herein, a vegetable oil is not prepared by method of distillations, which are usually utilized to prepare fragrances and/or essential oils. Instead, vegetable oil is typically extracted from plants by chemical extraction and/or physical extraction. Chemical extraction comprises using a chemical agent as a solvent to extract vegetable oils from plant. A common solvent is hexane, which can be derived from petroleum. Another way is physical extraction, which does not use solvent extracts. Physical extraction involves what is known as the "traditional" way by using several different types of mechanical extraction. Expeller-pressed extraction is one type, and there are two other types that are both oil presses: the screw press and the ram press. A vegetable oil can be saturated or unsaturated, and can be edible or inedible. Examples of vegetable oils include, but are not limited to, canola oil, sunflower oil, safflower oil, peanut oil, bean oil, including soybean oil, linseed oil, tung oil, olive oil, corn oil, sesame oil, cumin oil, peanut oil, and castor oil. In one embodiment, vegetable oil is extracted from a whole plant, or from a plant part (e.g., seeds).

α-terpinene, p-cymene and limonene are publicly available to those skilled in the art, can be produced synthetically using known methods, or can be purified from various plant extracts, as described in more detail below. In addition, all three of these terpenes are commercially available (e.g., Sigma-Aldrich®, Acros Organics, MP Biomedicals, Merck Chemicals). The concentration of each pesticidally active chemical compound is described below in the composition section. Unless otherwise noted, the percentages provided below reflect the percentage of each terpene present in the simulated blend, and exclude any impurities present in each of these substantially pure compounds. For example, if the simulated blend contains alpha-terpinene that is 90% pure, the percentage shown below reflects the amount of pure alpha-terpinene that is included in the composition, excluding the 10% impurities. Therefore, if such simulated blend constitutes 40% alpha-terpinene, the substantially pure alpha-terpinene used to prepare the blend is about 44%, with 40% alpha-terpinene and 4.4% impurities.

Methods for synthesizing or purifying the terpenes in the simulated blend are well known to those of skill in the art. Each of the terpene components of the simulated blend may be obtained by either chemical synthesis or from a plant extract. For example, α-terpinene may be obtained from acid isomerization of terpinolene. p-cymene may be obtained by disproportionation of dipentene or by dehydration of camphor. In addition, p-cymene may be obtained from limonene, as described in Martin-Luengo, M. A., et al. "Synthesis of p-cymene from limonene, a renewable feedstock" Applied Catalysis B: Environmental (Jun. 24, 2008) 81(3-4), 218-224. The term chemical synthesis, as used herein, includes synthesis using a plant extract as a starting material. For example, as described above, p-cymene may be obtained from limonene. In turn, the limonene starting material may be obtained from a citrus extract. The terpene components of the simulated blend may all be obtained by chemical synthesis or all from one or more non-*Chenopodium* plant extracts, or some components may be made by chemical synthesis and others obtained from non-*Chenopodium* plant extracts. In one embodiment, the alpha-terpinene and the p-cymene are synthetically produced and the limonene is derived from a plant extract.

Numerous plant species produce terpenes, some of which produce the terpene compounds utilized in the methods of the present invention.

At least the following plant species produce α-terpinene: *Anethum graceolens, Artemisia argyi, Cuminum cyminum, Elettaria cardomonum, Melaleuca alternifolia, Cardamom* spp. and *Origanum majorana*.

At least the following plant species produce limonene, including d-limonene: *Anethum graceolens, Anethum sowa, Carum carvi, Citrus, Foeniculum vulgare, Mentha piperita* and *Peppermint*. Limonene may be obtained by steam distillation after alkali treatment of citrus peels and pulp, and also by the fractionation of orange oil.

At least the following plant species produce p-Cymene: *Coridothymus sativum, Coridothymus captitatus, Cuminum cyminum, Origanum vulgare* and *Thymus vulgaris*.

For additional information on plants that produce terpene, see, for example, Paul Harrewijn et al., *Natural terpenoids as messengers: a multidisciplinary study of their production, biological functions, and practical applications*, Published by Springer, 2001 (ISBN 0792368916, 9780792368915); Paul M. Dewick, Medicinal Natural Products: A Biosynthetic Approach, Published by John Wiley and Sons, 2009 (ISBN 0470741678, 9780470741672); Ronald Hunter Thomson, *The Chemistry of natural products*, Published by Springer, 1993 (ISBN 0751400149, 9780751400144); and Leland J. Cseke et al. *Natural products from plants*, Published by CRC Press, 2006, (ISBN 0849329760, 9780849329760), each of which is incorporated by reference herein in its entirety.

In one embodiment, essential oils, and/or certain fractions of essential oils (e.g., certain terpenes) can be extracted from a plant by distillation. As used herein, "Essential Oil Extract" means the volatile, aromatic oils obtained by steam or hydro-distillation of plant material and may include, but are not restricted to, being primarily composed of terpenes and their oxygenated derivatives. Essential oils can be obtained from, for example, plant parts including, for example, flowers, leaves, seeds, roots, stems, bark, wood, etc. A variety of strategies are available for extracting essential oils from plant material, the choice of which depends on the ability of the method to extract the constituents in the extract of the present invention. Examples of suitable methods for extracting essential oil extracts include, but are not limited to, hydro-distillation, direct steam distillation (Duerbeck, K., et al., (1997) The Distillation of Essential Oils. Manufacturing and Plant Construction Handbook. Protrade: Dept. of Foodstuffs and Agricultural Products. Eschborn, Germany. pp. 21-25.), solvent extraction, and Microwave Assisted Process (MAP™) (Belanger et al., (1991) Extraction et Determination de Composes Volatils de L'ail (*Allium sativum*), Riv. Ital. EPPOS 2: 455-461.). Detailed distillation methods have been described in WO 2001/067868 and WO 2004/006679, which are incorporated by reference in their entireties.

In one embodiment, a volume filler is added to the terpenes in the simulated blend to replace the minor terpene components of the *Chenopodium* plant extract. The volume filler is a compound that mixes well with terpenes and creates a good suspension of terpenes, may be inert or have some insecticidal activity, and does not cause phytotoxicity. The excipients described below may serve as both excipients and volume fillers.

In one aspect of the invention, the concentration of the biopesticidally active chemical compounds in the simulated blend are about the same as their respective concentrations in the extract of *Chenopodium ambrosioides* near *ambrosioides*, and the fraction of volume composed by filler is about the same as that of the minor terpene constituents and impurities in such *Chenopodium* extract. In such embodiment, the relative percentages of the active ingredient (i.e., the three major terpenes) and volume filler (replacing the minor terpene constituents) can vary within certain ranges.

In one embodiment, the concentration of α-terpinene in the simulated blend ranges from about 30% to about 70%, by weight; the concentration of p-cymene in the simulated blend ranges from about 10% to about 30%, by weight; and the concentration of limonene in the simulated blend ranges from about 1% to about 20%, by weight. For example, the concentration of α-terpinene in the simulated blend ranges from about 32% to about 50%, by weight. The concentration of p-cymene in the simulated blend ranges from about 12.5% to about 20%, by weight. The concentration of limonene in the simulated blend ranges from about 9% to about 15%, by weight. The concentration of volume filler ranges from about 15% to about 47%, by weight. As noted above, the above percentages reflect pure compounds. Use of substantially pure compounds is also contemplated and described herein, and substantially pure compounds, as described above, may have impurities, which would increase the percentage of substantially pure compound in the mixture. For example, the range of concentrations, by weight, of substantially pure terpenes in the simulated blend may range from about 33% to about 78% α-terpinene and from about 11% to about 33% p-cymene and from about 1.1% to about 22% limonene. The other ranges would also increase similarly, and may increase by about 10%, in the case of use of substantially pure compounds. As explained further herein elsewhere, these concentrations represent the concentrations of the terpenes in a concentrated composition that is typically diluted for application to plants and/or the areas around plants or to any other area where control is desired. In one embodiment, the extract is mixed with other components (e.g., carrier, emulsifier, spreader-sticker) to produce a formulated product, wherein the extract is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the formulated product, by weight. For example, the extract is about 25% of the formulated product, by weight. In such a formulated product, the concentration of α-terpinene ranges from about 8.75% to about 10.25%, by weight; the concentration of p-cymene ranges from about 3.75% to about 6.25%, by weight; the concentration of limonene ranges from about 1.25% to about 3.75%, by weight.

In another embodiment, the concentration of each pesticidally active chemical compound can be higher or lower than the one in the essential oil extract, but roughly maintaining relative ratio to each others as in the essential oil extract. For non-limiting example, the relative ratio of α-terpinene, p-cymene, and limonene is about 39:17:12, or about 40:15:12, or about 36:14.9:11.4, or about 10.175:3.9:3.05. In some other embodiments, the range of α-terpinene in the relative ratio may be about 30 to about 50, the range of p-cymene in the relative ratio may be about 10 to about 20, and the range of limonene in the relative ratio may be about 5 to about 20; i.e., 30-50:10-20:5-20. Still in some other embodiments, the relative ratio of α-terpinene, p-cymene, and limonene is about 35 to about 45 for α-terpinene, about 12 to about 18 for p-cymene and about 10 to about 15 for limonene. One skilled in the art will be able to determine the actual ratio of each terpene in a blend according to the relative ratios. For example, the synthetic blend can consist of: between about 35% and about 45% by weight of α-terpinene, between about 15% and about 25% by weight of p-cymene, between about 5% and about 15% by weight of limonene, and between about 0% and 99.715% by weight of volume filler wherein the relative ratio among these three terpenes is selected from the group consisting of about 39:17:12, or about 40:15:12, or about 36:14.9:11.4, or about 10.175:3.9:3.05 or about 35-45:12-18:10-15. In addition, no matter what concentrations of α-terpinene, p-cymene, limonene are in a composition, the relative ratio among these three terpenes may be within the ranges set forth above in this paragraph.

In one embodiment, the relative amounts by weight of the natural and/or synthetic terpenes and of the fillers in the composition are as follows: about 36% α-terpinene, about 15% p-cymene, about 11% limonene and about 33% solvent (e.g., vegetable oil), by weight. The percentages in this embodiment do not total 100% because the terpenes used are substantially pure and contain some impurities. For example, in one embodiment, the alpha-terpinene is 90% pure, the limonene is 95% pure and the cymene is 99% pure. In one embodiment, the impurities are not compounds that are detectable in an extract of *Chenopodium ambrosioides* near *ambrosioides*. In yet another embodiment, the impurities are not thymol, carvacrol, carvone, carveol and/or nerol.

In another aspect of the invention, the natural and/or synthetic terpenes and fillers in the simulated blend are mixed with other components (e.g., carrier, emulsifier, spreader-sticker, referred to herein collectively as excipients) to produce a formulated product, wherein the substantially pure natural and/or synthetic terpenes and fillers are about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the formulated product, by weight. For example, the substantially pure natural and/or synthetic terpenes and fillers are about 25% of the formulated product, by weight. In one embodiment of such a formulated product containing 25% simulated blend, the simulated blend portion of the composition consists of between about 8% and about 12.5% by weight of α-terpinene, between about 3% and about 5% by weight of p-cymene, between about 2.0% and about 3.75% by weight of limonene, and between about 3.75% to about 11.75% by weight of volume filler. In another embodiment, the concentration of α-terpinene is about 10%, by weight; the concentration of p-cymene is about 3.75%, by weight; the concentration of limonene is about 3%, by weight; and the filler(s) is about 8.25%, by weight. In yet another embodiment, the concentration of α-terpinene is about 9%, by weight; the concentration of p-cymene is about 3.72%, by weight; the concentration of limonene is about 2.85%, by weight; and the filler(s) is about 8.25%, by weight.

Spray formulations include aqueous solutions, water-soluble powders, emulsifiable concentrates, water miscible liquids/powders (for pesticidal compounds that are soluble in water), wettable powders or water-dispersible powders, flowable/sprayable suspensions or suspension concentrates, and oil solutions. Although sprays are a very popular method of applying pesticides, only a small number of pesticides are sufficiently soluble in water to be formulated into an aqueous solution, water-soluble powder, or water miscible liquid or powder. Therefore, most spray formulations need an organic solvent or a specialized formulation to enable them to be mixed with water for spray application.

An important spray formulation for the invention is an emulsifiable concentrate. In an emulsifiable concentrate, a concentrated organic solvent based solution of the pesticidal compound (or the pesticidal compound alone if it is a liquid at room temperature) is added to an emulsifier. An emulsifier is a detergent-like (surfactant) material that allows microscopically small oil droplets to be suspended in water to form an emulsion. The concentrate is thereby dispersed evenly throughout an aqueous solution and generally remains suspended for an extended period of time (days).

Emulsifiers useful in the invention include Tween™ 200, Tween™ 600, sorbitol (polysorbate 80), propylene glycol, polyethylene glycol, ethanol (ethyl alcohol) and methanol (methyl alcohol). Another class of surfactant that can be used as an emulsifier for pesticide formulations is the phosphate esters. Examples of commercially available phosphate ester surfactants include: butyl phosphate, hexyl phosphate, 2-ethylhexyl phosphate, octyl phosphate, decyl phosphate, octyldecyl phosphate, mixed alkyl phosphate, hexyl polyphosphate, and octyl polyphosphate. For example, the emulsifier used is either Tween™ 200, sorbitol 80, propylene glycol, polyethylene glycol, or ethyl alcohol.

Emulsifiable concentrates are the preferred spray formulation for the pesticidal compounds of the invention since many pesticide compounds are poorly soluble in water and would otherwise settle out in the spray tank after dilution, altering the concentration during spraying.

Non-limiting examples of conventional carriers that may be used in formulations of the present invention include liquid carriers, including aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes), halogenated especially chlorinated, aromatic hydrocarbons (e.g., chlorobenzenes), cycloalkanes (e.g., cyclohexane), paraffins (e.g., petroleum or mineral oil fractions), chlorinated aliphatic hydrocarbons (e.g., methylene chloride, chloroethylenes), alcohols (e.g., methanol, ethanol, propanol, butanol, glycol), as well as ethers and esters thereof (e.g., glycol monomethyl ether), amines (e.g., ethanolamine), amides (e.g., dimethyl sormamide), sulfoxides (e.g., dimethyl sulfoxide), acetonitrile, ketones (e.g., acetone, methyl ethyl ketone, methyl isobutyl ketone, cyclohexanone), and/or water; as well as inert dispersible finely divided solid carriers such as ground natural minerals (e.g., kaolins, clays, vermiculite, alumina, silica, chalk, i.e., calcium carbonate, talc, attapulgite, montmorillonite, kieselguhr), and ground synthetic minerals (e.g., highly dispersed silicic acid, silicates). More non-limiting examples of suitable carriers/solvents include, but are not limited to, Isopar™ M, THFA™, ethyl lactate, butyl lactate, Soygold™ 1000, M-Pyrol, Propylene glycol, Agsolex™ 12, Agsolex™ BLO, Light mineral oil, Polysolve™ TPM, and Finsolv™ TN. In one embodiment, the solvent in said composition of present invention can be organic solvent, e.g. petroleum distillates or hydrocarbons. In one embodiment, the solvent is vegetable oil. For example, the solvent is canola oil. In another embodiment, the solvent is a methyl ester. For example, the solvent is methyl ester of soybean oil (a.k.a. methyl soyate). Methyl ester of soybean oil can be commercially produced, e.g. Steposol® SB-W. In a further embodiment of present invention, the solvent is mixture of canola oil and Steposol® SB-W. In one embodiment, the concentration of solvent in the composition of present invention is about 0%, at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, by weight. For example, the concentration of said solvent in a formulated composition of present invention ranges from about 0% to about 99%, by weight, from about 10% to about 50%, or from about 50% to about 99%, or from about 20% to about 50%, or from about 30% to about 50%, or ranges from about 30% to about 40%, by weight.

In some embodiments of the present invention the carrier is an oil, such as a fixed oil (including vegetable and animal oils) or a mineral oil, but excluding essential oils. In some embodiments of the present invention the carrier and/or volume filler is also an active compound against insects and/or mites. For example, such a carrier and/or volume filler is a vegetable oil. Vegetable oils, saturated or unsaturated, edible or inedible, include, but are not limited to, canola oil, sunflower oil, safflower oil, peanut oil, bean oil, linseed oil, tung oil, and castor oil. The concentration of said solvent in a formulated composition of present invention ranges from about 0% to about 99%, by weight, from about 10% to about 50%, or from about 50% to about 99%, or from about 20% to about 50%, or from about 30% to about 50%, or ranges from about 30% to about 40%, by weight.

The adjuvant in said composition of present invention can be selected from the group consisting of other additional carriers, spreaders-stickers, surface-active agents, e.g. emulsifiers and/or dispersing agent, penetrants, safeners, anticaking agents, and mixture thereof.

In one embodiment, the adjuvant comprises at least a second carrier, a spreader, and an emulsifier. In one embodiment, the total concentration of the second carrier, the spreader, and the emulsifier in the composition of present invention is about 0%, at least about 5%, about 10%, about 15%, about 20%, about 25%, about 30%, about 35%, about 36%, about 37%, about 38%, about 39%, about 40%, about 45%, about 50%, about 55%, about 60%, about 65%, about 70%, about 75%, about 80%, about 85%, about 90%, about 95%, or about 99%, by weight. For example, the concentration of said solvent in the composition of present invention ranges from about 0% to about 99%, by weight, from about 10% to about 50%, or from about 50% to about 99%, or from about 20% to about 50%, or from about 30% to about 50%, or ranges from about 30% to about 40%, by weight.

Non-limiting examples of suitable spreaders and/or sticking agents include, but are not limited to, Latex emulsion, Umbrella™, Adsee™ 775, Witconol™ 14, Toximul™ 858, Latron™ B-1956®, Latron™ CS-7®, Latron™ AG-44M, T-Mulz™ AO-2, T-Mulz™ 1204, Silwet™ L-774, SUSTAIN® (Western Farm Service, Inc.; Miller Chemical & Fertilizer Corp.), Pinetac® (Britz Fertilizers, Inc.), Nufilm P® (Miller Chemical & Fertilizer Corporation), Nufilm 17® (Miller Chemical & Fertilizer Corporation), Sufrix®, Cohere®, Induce®, Picclyte® (e.g., Picclyte A115), Peg600 Argimax 3H®, alpha and beta pinene polymers and co-polymers, PEG 400-DO, Lipopeg 10-S, Maximul 7301, and PEG 600ML®.

SUSTAIN® is a commercially available spreader/sticker, which comprises polyterpene resin (a proprietary mixture of pinene polymers). The chemical compound pinene is a bicyclic terpene ($C_{10}H_{16}$, 136.24 g/mol) known as a monoterpene. There are two structural isomers found in nature: α-pinene and β-pinene. As the name suggests, both forms are important constituents of pine resin; they are also found in the resins of many other conifers, and more widely in other plants. Both are also used by many insects in their chemical communication system. α-Pinene and β-pinene can be both produced from geranyl pyrophosphate, via cyclisation of linaloyl pyrophosphate followed by loss of a proton from the carbocation equivalent. Methods of producing α-pinene polymers and β-pinene polymers have been described in U.S. Pat. Nos. 3,466,271, 4,011,385 and U.S. Patent Publication No. 2009/0209720, and in Barros et al. (Potentially Biodegradable Polymers Based on—or—Pinene and Sugar Derivatives or Styrene, Obtained under Normal Conditions and on Microwave Irradiation, European Journal of Organic Chemistry, Volume 2007 Issue 8, pp. 1357-1363), and Radbil et al. (Preparation of High-Melting Polyterpene Resins from α-Pinene, Russian Journal of Applied Chemistry Volume 78, Number 7, pp. 1126-1130). In one embodiment, the biopesticidal composition of the present invention which comprises a simulated terpene blend as described previously (e.g., 25% of a simulated terpene blend, by weight) can further comprise a spreader/sticker, for example SUSTAIN®, wherein the concentration of the spreader ranges from about 1% to about 10%, for example about 5%, by weight.

Surface-active agents that can be employed with the present invention include, without limitation, emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin-hydrolyzates, and especially alkyl arylpolyglycol ethers, magnesium stearate, sodium oleate); and/or dispersing agents such as lignin, sulfite waste liquors, methyl cellulose.

Emulsifiers that can be used to solubilize the simulated blends of the present invention in water include blends of anionic and non-ionic emulsifiers. Examples of commercial anionic emulsifiers that can be used include, but are not limited to: Rhodacal™ DS-10, Cafax™ DB-45, Stepanol™ DEA, Aerosol™ OT-75, Rhodacal™ A246L, Rhodafac™ RE-610, Rhodapex™ CO-433, Rhodapex™ CO-436, Rhodacal™ CA, Stepanol™ WAC. Examples of commercial non-ionic emulsifiers that can be used include, but are not limited to: Igepal™ CO-887, Macol™ NP-9.5, Igepal™ CO-430, Rhodasurf™ ON-870, Alkamuls™ EL-719, Alkamuls™EL-620, Alkamide™ L9DE, Span™ 80, Tergitol™ TMN-3, Tergitol™ TMN-6, Tergitol™ TMN-10, Morwet™ D425, Tween™ 80, Alkamuls™ PSMO-5, Atlas™ G1086, Tween™ 20, Igepal™ CA-630, Toximul™ R, Toximul™ S, Polystep™ A7, and Polystep™ B1. In one embodiment, the emulsifier in said composition of present invention is Tween™. In one embodiment, the concentration of emulsifier in said composition of present invention is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, by weight. For example, the concentration of emulsifier in said composition of present invention ranges from about 1% to about 15%, or ranges from about 5% to about 10%, by weight. In one embodiment, the concentration of emulsifier in the composition is about 7.5%, by weight.

In one embodiment, the spreader-sticker is polyterpene resin, e.g. proprietary mixture of pinene polymers. In one embodiment, the spreader-sticker is Latron™ B-1956® (Dow AgroSciences, LLC), which consists of 77% modified phthalic glycerol alkyd resin and 23% butyl alcohol by weight. In one embodiment, the concentration of Latron™ B-1956® in said composition of present invention is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, by weight. For example, in some embodiments the concentration of spreader-sticker in said composition of present invention ranges from about 1% to about 15%, or ranges from about 5% to about 10%, by weight. In one embodiment, the concentration of spreader-sticker in the composition is about 7.5%, by weight. In some embodiments, the concentration of spreader-sticker in said composition of present invention is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, by weight. For example, the concentration of spreader-sticker in said composition of present invention ranges from about 1% to about 15%, or ranges from about 5% to about 10%, by weight. In one embodiment, the concentration of spreader-sticker in the composition is about 7.5%, by weight.

In one embodiment, the composition of the present invention is diluted with at least one solvent, for example, with water, by the end user before application. The amount of dilution depends upon various factors, including the nature of the crop and target insect or acari targeted and/or the amount of pest pressure. While not wishing to be bound by any particular theory, one mode of action of the compositions of the present invention is considered as non-toxic, and involves a process by which the compositions soften cuticles in target insects, resulting in a disruption of insect respiration. This occurs by direct contact and localized fumigant action. In plant hosts on which the insect or acari tends to target the topside of the plant, less active ingredient is required and a more dilute solution is used. For crops in which the insect or acari tend to target the underside of the leaf or in which the insect or acari are less exposed to a typical spray application, more active ingredient is necessary for control.

The composition can be diluted at least about 1.5 times, about 2 times, about 3 times, about 4 times, about 5 times, about 10 times, about 20 times, about 30 times, about 40 times, about 50 times, about 60 times, about 70 times, about 80 times, about 90 times, about 100 times, about 200 times, about 300 times, about 400 times, about 500 times, about 600 times, about 700 times, about 800 times, about 900 times, about 1000 times, about 1500 times, about 2000 times, about 2500 times, about 3000 times, about 4000 times, about 5000 times, about 6000 times, about 7000 times, about 8000 times, about 9000 times, or about 10000 times. For example, the composition can be diluted between about 1 time and about 50 times. For another example, the composition can be diluted between about 50 times to about 400 times.

In one embodiment, between about 1 quart and about 10 quarts of a formulation containing 25% of the simulated blend are diluted in 100 gallons of water and applied to an acre. In other embodiments, a formulated composition comprising higher level of active ingredient can be applied at an even lower rate.

In one specific example in which the formulated simulated blend contains 10% substantially pure alpha-terpinene, 3.75% substantially pure p-cymene and 3% substantially pure limonene, the final concentration of each substantially pure terpene applied upon dilution in 100 gallons of water is as shown in the Table 1 below.

TABLE 1

Exemplary final concentrations of terpenes after dilution of simulated blend

| | Terpinene (density = 0.84 g/ml) | p-cymene (density = 0.86 g/ml) | d-limonene (density = 0.84 g/ml) |
|---|---|---|---|
| 1 quart (400x dilution) | 0.021% | 0.008% | 0.006% |
| 2 quart (200x dilution) | 0.042% | 0.016% | 0.013% |
| 5 quart (80x dilution) | 0.105% | 0.04% | 0.0315% |

Regardless of the initial concentration of each terpene in a composition, the final composition applied by the end user to kill, inhibit, prevent and/or repel insect and mite plant pests will comprise the following components: between about 0.017% and about 0.21% by weight of α-terpinene, between about 0.008% and about 0.08% by weight of p-cymene, and between about 0.006% and about 0.063% by weight of limonene. For example, the composition will comprise between about 0.04% and about 0.1% by weight α-terpinene, between about 0.015% and about 0.04% by weight p-cymene, and between about 0.010% and about 0.03% by weight limonene. More examples are the compositions provided in the examples below.

The concentration of the simulated blend in the composition to be applied to plants and plant parts, depending on whether it is in the concentrated or diluted (ready-to-spray) form, can be at least about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, by weight.

Biopesticide Application

Biopesticidal compositions, either diluted or undiluted, can be applied in a number of different ways. For small scale application of a liquid pesticidal composition, backpack tanks, hand-held wands, spray bottles, or aerosol cans can be utilized. For somewhat larger scale application of liquid pesticidal compositions, tractor drawn rigs with booms, tractor drawn mist blowers, airplanes or helicopters equipped for spraying, or fogging sprayers can all be utilized. Small scale application of solid formulations can be accomplished in a number of different ways, examples of which are: shaking product directly from the container or gravity-application by human powered fertilizer spreader. Large scale application of solid formulations can be accomplished by gravity fed tractor drawn applicators, or similar devices.

In one embodiment, compositions of a simulated blend of *Chenopodium ambrosioides* near *ambrosioides* are applied to a plant or a plant part at any time during the life cycle of the plant, during one or more stages of the plant's life cycle, or at regular intervals of the plant's life cycle, or continuously throughout the life of the plant.

In another embodiment, the compositions of the present invention are applied to a plant before the emergence or appearance of a plant pest, or after the emergence or appearance of a plant pest but before the plant pest density reaches economic threshold. By applying the compositions to plants before the plant pest populations reach the economic threshold for a particular plant pest species and plant species combination, the lethal, preventative, inhibitory and/or repelling effect of the compositions can be maintained for as long as desirable by repeated applications. Economic threshold may vary depending on insect species, plant species, plant part and/or plant developmental stage. Economic threshold may vary depending on plant pest species, plant species, plant part and/or plant developmental stage. For example, Table 2 shows a number of recommended, representative economic thresholds.

TABLE 2

Recommended Economic Thresholds

| Insect Species | Plant Species/ Part | Recommended Economic Threshold |
|---|---|---|
| Alfalfa weevil | Alfalfa/Hay | 25-50% of leaves on upper ⅓ of stem, or 50-70% of foliage tips show injury |
| Alfalfa weevil | Alfalfa/Seed | 35-50% of plants show damage or 20-25 larvae/sweep |
| Birdcherry-oat aphid | Cereals | 12-15 aphids/stem prior to soft dough; |
| Birdcherry-oat aphid | Canaryseed | 10-20 aphids on 50% of the stems prior to soft dough |
| Corn leaf aphid | Cereals | 12-15 aphids/stem prior to soft dough |
| Russian wheat aphid | Cereals | 10% of the plants infested with at least 1 aphid when first node visible 10% of the tillers infested with 1 aphid when tip of flag leaf just visible |
| Green bug | Cereals | 12-15 aphids/stem prior to soft dough |
| Potato aphid | Flax | 2-3 aphids/main stem at full bloom* Flax 8 aphids/main stem at green boll stage |
| Pea aphid | Peas* | 2-3 aphids on top 20 cm of plant tip (Trapper peas can withstand considerably higher levels) *main stem is considered to be the main yield component of the plant (usually the primary stem) |
| Thrips Barley | Oats | 7-8 thrips/stem prior to head emergence; Red Clover 50-80 thrips per flower head |
| Beet Webworm | Canola | 20-30 larvae/m2; Flax >10 larvae/m2 |
| Clover cutworm | Canola | Mustard 20-30 larvae/m2; Flax Economic thresholds not yet established but expected to be lower than cereals |
| Cutworms | Cereals | 3-4 larvae/m2; Oilseeds Economic thresholds not yet established but expected to be lower than cereals |
| Diamondback moth | Canola | Mustard 100-150 larvae/$m^2$ in immature and flowering fields**; 200-300 larvae/$m^2$ in podded canola fields** **Note that these threshold numbers are based on stands averaging 150 to 200 plants/$m^2$. In areas where stands are thinner the economic threshold should be lowered accordingly. |
| Grasshoppers | Cereals | 8-12 grasshoppers/$m^2$ |
| Grasshoppers | Flax | Lentil 2 grasshoppers/$m^2$-depending on crop stage (i.e. lentil pods are far more prone to attack than is the foliage) |
| Grasshoppers | Canola | >14 grasshoppers/$m^2$ |
| Orange wheat blossom midge | Wheat | 1 midge/4-5 wheat heads |
| Painted lady butterfly | Sunflowers | 25% defoliation |
| Alfalfa plant bug | Alfalfa/Seed | 4 bugs/sweep |
| Alfalfa plant bug | Alfalfa/Hay | control not recommended |
| Lygus bug | Alfalfa/Seed | 8 bugs/sweep |
| Lygus bug | Alfalfa/Hay | control not recommended |
| Lygus bug | Canola | 1.5 bugs/sweep (may varies) |
| Red sunflower seed weevil | Sunflower Oil crop | 12-14 weevils/head at 85-100% bloom |
| Red sunflower seed weevil | Confectionery | 1-2 weevils/head at 85-100% bloom |
| Red turnip beetle | Canola | As soon as beetles become numerous |
| Sunflower beetle | Sunflowers | 1 adult beetle/2-3 seedlings at the 2-6 leaf stage or >10 larvae per plant during summer |

TABLE 2-continued Recommended Economic Thresholds

| Insect Species | Plant Species/ Part | Recommended Economic Threshold |
|---|---|---|
| Sunflower moth | Sunflowers | As soon as moths are present and >10% of blooms |
| Sweetclover weevil | Clover | 1st year stands: 1 weevil/3 seedlings (1/5 seedlings under dry conditions); 2nd year stands: 9-12 weevils/plant |

More recommended economic thresholds can be found in Lamb, et al. Agribinusts Conference, 2004, pp. 90-98; Ward, *Australian Journal of Entomology* (2005) 44, 310-315; Byrne et al. N.C. Toscano/Crop Protection 25 (2006) 831-834; Boica et al. Journal of Insect Science, 2008, vol. 8 pp. 8-9; Wright et al. Bulletin of Entomological Research, 2007 vol. 97, pp. 569-757; Meng et al. Journal of Biological Systems 2007, vol. 15, pp. 219-234; Wang et al. Yangzhou Daxue Xuebao Ziran Kexue Ban 2006, vol. 9, pp. 36-41; Dumbauld et al. Aquaculture, 2006 vol. 261, pp. 976-992; Ajeigbe et al. Crop Protection, 2006, vol. 25, pp. 920-925; Posey et al., Journal of Economic Entomology, 2006, vol. 99, pp. 966-971; Byrne et al. Crop Protection, 2006, vol. 25 pp. 831-834; Bird et al. Bulletin of Entomological Research, 2006 vol. 96, pp. 15-23; Ward, Australian Journal of Entomology, 2005, vol. 44, pp. 310-315; Duffield, Australian Journal of Entomology, 2005, vol. 44, pp. 293-298; Bhattacharyya et al. Australian Journal of Entomology, 2005, vol. 98, pp. 814-820; Zou, et al. Environmental Entomology, 2004, vol. 33, pp. 1541-1548; Fettig et al. Journal of Arboriculture, 2005, vol. 31, pp. 38-47; Hori, Applied Entomology and Zoology, 2005, vol. 38, pp. 467-473; Prokopy, Agriculture Ecosystems & Environment, 2003, vol. 94, pp. 299-309; Agnello, Agriculture Ecosystems & Environment, 2003, vol. 94, pp. 183-195; Schuster, Journal of Economic Entomology, 2002, vol. 95, pp. 372-376; Harris et al. *Calculating a static economic threshold and estimating economic losses for the pecan weevil*, Southwestern Entomologist; Dent, *Insect pest management* published by CABI, 2000, ISBN 0851993400, 9780851993409, Pimentel, *Biological invasions* Published by CRC Press, 2002, ISBN 0849308364, 9780849308369; R. Cavalloro, *Statistical and mathematical methods in population dynamics and pest control*, Published by CRC Press, 1984, ISBN 9061915481, 9789061915485; Metcalf et al., *Introduction to insect pest management*, William Henry Luckmann, Edition: 3, Published by Wiley-IEEE, 1994, ISBN 0471589578, 9780471589570; each of which is incorporated herein in its entirety.

For example, the compositions can be applied before, during and/or shortly after the plants are transplanted from one location to another, such as from a greenhouse or hotbed to the field. In another example, the compositions can be applied shortly after seedlings emerge from the soil or other growth media (e.g., vermiculite). In yet another example, the compositions can be applied at any time to plants grown hydroponically. In other words, according to the methods of the present invention the compositions can be applied at any desirable time but before the insect and/or mite pests reach an economic threshold, as explained in more detail herein. One skilled in the art of insect control will know the economic threshold for a particular plant species, a particular insect species, the stage of plant growth, the environmental conditions during plant growth, the amount of insect damage the grower and the market will tolerate, etc.

In another embodiment, the compositions of the present invention are applied to a plant and/or plant part any time in the life cycle of the plant. For example, the compositions can be applied to the plant before, during, or after the insect and/or mite density reaches economic threshold.

The present invention also provides methods of enhancing the killing, inhibiting, preventative and/or repelling activity of the compositions of the present invention by multiple applications. In some other embodiments, the compositions of the present invention are applied to a plant and/or plant part for two times, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. Still in some embodiments, the compositions of the present invention are applied to a plant and/or plant part for more than two times, for example, 3 times, 4 times, 5 times, 6 times, 7 times, 8 times, 9 times, 10 times, or more, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. The intervals between each application can vary if it is desired. One skilled in the art will be able to determine the application times and length of interval depending on plant species, plant pest species, and other factors.

5. Further Preparation of Pesticidal Composition

The formulated pesticidal composition can either be applied directly or can be diluted further before application. The diluent depends on the specific treatment to be accomplished, and the method of application. For example, a pesticidal composition that is to be applied to trees could be diluted further with water to make it easier and more efficient to spray with known spraying techniques. A biopesticidal composition of present invention can be diluted by solvent, e.g. water before application, wherein the final composition applied by the end user to inhibit, prevent and/or repel insects will comprise following components: between about 0.020% and 1.70% by weight of α-terpinene, between about 0.008% and 0.65% by weight of p-cymene, and between about 0.005% and 0.500% by weight of limonene. For example, the composition will comprise between about 0.044% and 0.28% by weight α-terpinene, between about 0.017% and 0.11% by weight p-cymene, and between about 0.013% and 0.086% by weight limonene. For another example, the composition will comprise between about 0.08% and 0.25% by weight α-terpinene, between about 0.035% and 0.080% p-cymene, and between about 0.030% and 0.075% by weight limonene.

Methods of Controlling Plant Pests Feeding on Plants

The present invention also provides methods of controlling plant pests, for example, methods of killing plant pests, inhibiting plant pests, preventing and/or repelling plant pests feeding on plants. In one embodiment, such a method consists of following steps:

i) Optional step if needed:
diluting the composition in the present invention with water into a final mixture, wherein said final mixture has at least following components: between about 0.017% and about 0.21% by weight of α-terpinene, between about 0.008% and about 0.08% by weight of p-cymene, and between about 0.007% and about 0.063% by weight of limonene. In another example, the composition will comprise between about 0.02% and about 0.1% by weight α-terpinene, between about 0.008% and about 0.04% by weight p-cymene, and between about 0.006% and about 0.03% by weight limonene.

In another example, the composition will comprise between about 0.04% and about 0.1% by weight α-terpinene, between about 0.015% and about 0.04% by weight p-cymene, and between about 0.010% and about 0.03% by weight limonene.

ii) applying said final mixture to the surface of plants wherein control of the insect and/or mite feeding on said plants is desired. For example, the insect and/or mite is killed, inhibited, and/or repelled or applying said final mixture to an area wherein control of the insect and/or mite feeding on said plant is desired.

In one embodiment, killing, inhibiting, preventing and/or repelling of plant pests contact and/or feeding on plants last for at least 1 day. In one embodiment, killing, inhibiting, preventing and/or repelling of plant pests contact and/or feeding on plants last for at least 2 days. In one embodiment, killing, inhibiting, preventing and/or repelling of plant pests contact and/or feeding on plants last for at least 3 days or at least 4 days, or at least 5 days, or at least 6 days. In one embodiment, killing, inhibiting, preventing and/or repelling of plant pests contact and/or feeding on plants last for at least 1 week. In other embodiments, killing, inhibiting, preventing and/or repelling of plant pests contact and/or feeding on plants last for at least 8 days, or at least 9 days, or at least 10 days, or at least 11 days, or at least 12 days, or at least 13 days, or at least 2 weeks, or at least 3 weeks, or at least one month or longer.

In some embodiments, said final mixture is applied to the surface of plants before the plant pest density reaches economic threshold, wherein the plant pest feeding on said plants is killed, inhibited, prevented and/or repelled. In other embodiments, said final mixture is applied to the surface of plants in any time during the life cycle of the plants. For example, said final mixture is applied to the surface of plants before, during, or after the plant pest density reaches economic threshold.

In some embodiments, the plants in said methods grow in a field, such as a grower's field or a farmer's field. In other embodiments, the plants in said methods grow in a hotbed, growth chamber, arboretum, solarium, on a window sill of home or office, or in a greenhouse. In other words, the methods of the present invention are useful in protecting plants from insects and/or mites wherever plants are grown and for whatever purpose the plants are cultivated, whether the plants be grown in pots, hydroponically or in a field in large-scale monoculture farming operations.

In some embodiments the formulated simulated blend is applied to a target area or host in order to control sucking, rasping and chewing pests, such as aphids, mites, white flies and *thrips*. In a particular embodiment the formulated simulated blend is applied to an insect, target area or host to control Asian citrus psyllids, green peach aphid, rosy apple aphid, spirea aphid, yellow aphid, black pecan aphid, turnip aphid, potato aphids, spirea aphid, silverleaf whitefly, sweetpotato whitefly, greenhouse whitefly, western flower *thrips*, eastern flower *thrips*, Florida flower *thrips*, onion *thrips*, chili *thrips*, citrus *thrips*, melon *thrips*, grape leafhoppers, variegated leafhoppers, and/or leafminers (*Liriomyza* spp.). In another embodiment, the formulated simulated blend is applied to an insect, a target area or host in order to control Lepidopterans (adults and/or larvae), such as melonworm, codling moth, oriental fruit moth, spotted tentiform leafminer, redbanded leafroller, and/or green fruitworm. In yet another embodiment the formulated simulated blend is applied to a target area or host to control mites such as the two-spotted spider mite, the Pacific spider mite, the European red mite, citrus rust mite, citrus red mite, Willamette spider mite, and/or the strawberry spider mite. In another embodiment, the formulated simulated blend is applied to a target area or host to control insects or mites that vector viral pathogens, or bacterial or fungal pathogens, which insects or mites and pathogens are described in detail above, and include, for example, whiteflies and psyllids that vector, for example, squash vein yellowing virus (which causes watermelon vine decline) or organisms that cause citrus greening or zebra chip disease, especially in potatoes, respectively.

In some embodiments, after application of the composition of the present invention, at least about 50% control of insects and/or mites is achieved compared to an area or host not treated with such compositions; in another embodiment at least about 60% control is achieved; in another at least about 70% control is achieved; in another at least about 80% control is achieved.

In some another embodiments, the compositions of present invention can be applied together, either mixed or separated but in consequences, or in rotations, with one or more other plant pest repellents to achieve inhibition, prevention, and/or repellency against broader plant pests species spectrum, and/or synergistic effects against specific plant pest species. Said other repellents may include, but are not limited to, 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; 2-hydroxyethyl-n-octyl sulfide; N-(cyanomethyl)-4-(trifluoromethyl)-3-pyridine-carboxamide (e.g. Flonicamid, FMC BELEAF™® 50 SG INSECTICIDE), pymetrozine (e.g. Fulfill®), and plant insect repellents described in U.S. Pat. Nos. 4,769,242, 4,869,896, 4,943,563, 5,221,535, 5,372,817, 5,429,817, 5,559,078, 5,591,435, 5,661,181, 5,674,517, 5,711,953, 5,756,113, 6,559,175, 6,646,011, 6,844,369, 6,949,680, 7,381,431, 7,425,595, each of which is incorporated by reference in its entirety herein, including all drawings/photographs that are a part thereof.

The following examples are given for purely illustrative and non-limiting purposes of the present invention.

EXAMPLES

Example 1

Exemplary Compositions of Present Invention

Table 3 below provides two non-limiting exemplary compositions C1 and C2 of the present invention, when the source of one or more terpenes has impurities.

TABLE 3

Exemplary compositions of the present invention

| Compound in Composition | % By Weight of Compound in Each of Compositions C1 and C2 | |
|---|---|---|
| | C1 | C2 |
| α-Terpinene | 36 | 39 |
| Limonene | 11.4 | 12 |
| p-Cymene | 14.9 | 17 |
| (Total of three above terpenes) | (62.3) | (68) |
| Minor terpene ingredients and impurities from extract used in C2 | | 32 |
| Impurities in C1 resulting from chemical synthesis and/or purification process | 4.7 | |
| Canola oil (filler) in wt % | 33 | |
| (Total weight percentage) | (100) | (100) |

Note:
C2 is a plant extract composition while C1 is a simulated blend composition. The percentage of each terpene in C1 reflects the percentage of absolutely pure compound with impurities subtracted out.

As set forth in Table 1, the terpenes used to make the simulated blend C1 are substantially pure but contain a small percentage of impurities by weight which are left over from the chemical synthesis and/or purification process. In C1, α-terpinene source (obtained by chemical synthesis) is about 90% pure, limonene source (obtained by purification from citrus peel and citrus oil) is about 95% pure, and p-cymene source (obtained by chemical synthesis) is about 99% pure. Thus, when mixing 39% α-terpinene source, 12% limonene source, and 17% p-cymene source with canola oil to simulate the plant extract composition C2, the percentage of absolutely pure compound with impurities subtracted out in C1 is 36% α-terpinene, 11.4% limonene source, and 14.9% p-cymene.

Table 4 below shows non-limiting exemplary formulated compositions C13 and C12 made from C1 or C2:

TABLE 4

Exemplary formulated compositions of the present invention.

| Ingredient | % By Weight of Ingredient in Each Formulated Composition C13 and C12 | |
|---|---|---|
| | C13 | C12 |
| Active = C1 (see Table 5) | 25 | |
| Active = C2 (see Table 5) | | 25 |
| Carrier/solvent | 35 | 37.5 |
| Other carrier/solvent, emulsifier, and spreader/binder | 40 | 37.5 |
| (Total Weight Percentage) | (100) | (100) |

Table 5 shows non-limiting exemplary compositions (C3 to C11, C15 and C19) of present invention.

TABLE 5

Exemplary compositions of the present invention

| Compound in wt % | C3 | C4 | C5 | C6 | C7 | C8 | C9 | C15 | C19 | C10* | C11* |
|---|---|---|---|---|---|---|---|---|---|---|---|
| α-Terpinene | 44.7 | 33 | 11.8 | 33 | 11.8 | 23.6 | 42 | 39 | 9.75 | 40 | 40 |
| limonene | 14.3 | 11 | 4.7 | 11 | 4.7 | 15.4 | 13 | 17 | 4.25 | 12 | 12 |
| p-Cymene | 19.2 | 18 | 6.9 | 18 | 6.9 | 13.8 | 14 | 12 | 3.00 | 15 | 15 |
| (Total of three above terpenes) | (78.2) | (62) | (23.4) | (62) | (23.4) | (52.8) | (69) | (68) | (17) | (67) | (67) |
| Carvacrol | | | | 0.43 | 0.43 | 0.43 | | | | | |
| L carveol (43% cis+ 54% trans) | | | | 0.58 | 0.58 | 0.58 | | 0.58 | 0.58 | | |
| Thymol | | | | 0.47 | 0.47 | 0.47 | | 0.47 | 0.47 | | |
| γ-Terpinene | | | | 0.14 | 0.14 | 0.14 | | 0.14 | 0.14 | | |
| Total terpene in wt % | 78.2 | 62 | 23.4 | 63.62 | 25.02 | 54.42 | 69 | | | | |
| Minor ingredients and impurities | | | | | | | | | | | 33 |
| Canola oil (filler) in wt % | 21.8 | 38 | 76.6 | 36.38 | 74.98 | 45.58 | 31 | | | 33 | |
| (Total weight percentage) | (100) | (100) | (100) | (100) | (100) | (100) | (100) | (100) | (100) | (100) | (100) |

** C11 is a plant extract composition, while C10 is a simulated blend composition. All numbers in the simulated blend C10 were calculated without considering the impurities in the source of each terpene. Thus, these numbers reflect the percentage of substantially pure compound.

Table 6 shows non-limiting exemplary formulated composition of present invention.

TABLE 6

Exemplary formulated composition of the present invention.

| | % by weight | |
|---|---|---|
| Ingredient | C16 | C17 |
| Active ingredients | 25.0 (of C11) | 25.0 (of C10) |
| Carrier/solvent | 35 or 37.5 | 35 or 37.5 |
| Other carrier/solvent, emulsifier, and spreader/binder | 40 or 37.5 | 40 or 37.5 |

Example 2

Efficacy of Exemplary Biopesticidal Composition 18 in Inhibiting Aphids

Material

TABLE 7

Composition 18

| Compound in wt % | C. 18 |
|---|---|
| α-Terpinene | Total 100% |
| | 10 |
| p-Cymene | 3.75 |
| limonene | 3 |
| Total terpene in wt % | 16.75 |
| Canola oil (volume filler) in wt % | 8.25 |
| Canola oil (carrier) | 35 |
| Steposol SB-W ® (carrier) | 25 |
| Tween 80 (emulsifier) | 7.5 |
| Latron™ B-1956 ® (Spreader-sticker) | 7.5 |

Composition 18 (C. 18, see Table 7) was made by mixing 25% by weight of synthetic blend, which consists of 40% of substantially pure α-Terpinene, 15% of substantially pure p-Cymene, 12% of substantially pure limonene and 33% canola oil (volume filler) by weight, with 35% of Canola oil (carrier), 25% of Steposol SB-W® (carrier), 7.5% Tween 80 (emulsifier) and 7.5% Latron™ B-1956® (Spreader-sticker) by weight.

Foliar biopesticidal trials to evaluate control of two aphid species (cotton aphid (CA) and green peach aphid (GPA)) by an exemplary composition provided by present invention were conducted in the southern United States. Aphid colonies maintained in the laboratory were used in all insecticide and transmission efficacy experiments.

Results

Foliar candidate biopesticides, including Composition 18, Endigo® ZC, and Fulfill® 50WG were applied using a $CO_2$ backpack sprayer equipped with a T-jet nozzle, delivering 40 gpa at 40 psi. Composition 18 was diluted either 200 times (0.5% v/v) or 100 times (1% v/v) with water before applications. Twenty-four hours after application, a single apterous adult aphid was confined to each test plant using a 1.2-cm-diameter clip cage on the abaxial surface of a leaf on the upper third of each test plant for the duration of the test. Sampling consisted of counting number of surviving aphids per test plant. Post-treatment counts were done on 1, 4 and 7 days after treatment (DAT) for *Ipomea setosa*, soybean, and potato. Percent control was calculated as (1-(treatment count/untreated control (UTC) count))×100 for that day. Analysis of variance was performed following transformation of count and percentage data using log 10(x+1). The Ryan-Einot-Gabriel-Welsch Multiple Range Test (REGWQ) was used to separate means, P=0.05.

Upon feeding, Green peach aphid can transmit Sweet potato feathery mottle virus to *Ipomea setosa*, or Potato virus Y to potato, while cotton aphid can transmit cucumber mosaic virus to soybean. Effectiveness of inhibiting and/or repelling of aphid feeding on plants can be indicated by No. of virus transmission archlets as determined by EPG. EPG experiments were conducted in a Faraday cage using a Giga 8 DC EPG amplifier with 1 Giga Ohm input resistance and an AD conversion rate of 100 Hz (Wageningen Agricultural University, Wageningen, The Netherlands). A DAS-800 Digital Acquisition Card (Keithley Instruments, Inc., Cleveland, Ohio) converted analogy signals into digital, which were visualized and recorded using WinDaq/Lite software (DATAQ Instruments, Inc., Akron, Ohio). Apterous adults were removed from either cotton or Chinese cabbage and immediately used in feeding behaviour studies. A 2-cm length of 25 μm gold wire (GoodFellow Metal Ltd, Cambridge, UK) was attached to the aphid dorsum with silver conductive paint (PELCO® Colloidal Silver no. 16034, Ted Pella, Inc., Redding, Calif.). Four test plants were placed randomly within the Faraday cage. Next, one aphid per test plant was then placed on the abaxial side of a leaf and feeding behaviour was recorded for 4 h, giving sufficient time for the aphid to phloem feed. This was repeated 10 times; 40 aphids per species, 120 h of aphid feeding on each test plant per aphid species. Pre-probe, xylem phase (G), E1 (sieve element salivation), and E2 (phloem sap ingestion) durations were recorded per 4 h feeding bout.

Table 8, Table 9, and Table 10 show efficacies of each candidate biopesticide to control green peach aphid or cotton aphid on *Ipomea setosa*, soybean and potato, respectively.

TABLE 8

Efficacy of insecticides to control green peach aphid on *Ipomea setosa*[a]

| Treatment/ | Rate | % control | | |
|---|---|---|---|---|
| formulation | product/A | 1 DAT | 4 DAT | 7 DAT |
| UTC | — | — | — | — |
| C 18 | 0.5% vol/vol | 0 a | 0 b | 22 b |
| C 18 | 1.0% vol/vol | 11 a | 11 b | 44 b |
| ENDIGO ® ZC | 4.50 oz | 22 a | 100 a | 100 a |
| FULFILL ® 50WG[b] | 2.75 oz | 33 a | 89 a | 100 a |

[a]Means followed by the same letter within columns are not significantly different (P > 0.05; REGWQ).
[b]Dyne-Amic was tank mixed with Fulfill at a rate of 3 pt/100 gal.

TABLE 9

Efficacy of insecticides to control cotton aphid on soybean[a]

| Treatment/ | Rate | % control | | |
|---|---|---|---|---|
| formulation | product/A | 1 DAT | 4 DAT | 7 DAT |
| UTC | — | — | — | — |
| C 18 | 0.5% vol/vol | 0 b | 27 c | 33 c |
| C 18 | 1.0% vol/vol | 0 b | 27 c | 53 b |
| ENDIGO ® ZC | 4.50 oz | 47 a | 93 a | 100 a |
| FULFILL ® 50WG[b] | 2.75 oz | 44 a | 60 b | 87 a |

[a]Means followed by the same letter within columns are not significantly different (P > 0.05; REGWQ).
[b]Dyne-Amic was tank mixed with Fulfill at a rate of 3 pt/100 gal.

TABLE 10

Efficacy of insecticides to control green peach aphid on potato[a]

| Treatment/ formulation | Rate product/A | % control 1 DAT | 4 DAT | 7 DAT |
|---|---|---|---|---|
| UTC | — | — | — | — |
| C 18 | 0.5% vol/vol | 11 a | 22 c | 22 c |
| C 18 | 1.0% vol/vol | 11 a | 22 c | 33 c |
| ENDIGO ® ZC | 4.50 oz | 22 a | 100 a | 100 a |
| FULFILL ® 50WG[b] | 2.75 oz | 11 a | 44 b | 67 b |

[a]Means followed by the same letter within columns are not significantly different (P > 0.05; REGWQ).
[b]Dyne-Amic was tank mixed with Fulfill at a rate of 3 pt/100 gal.

As Table 11 shows below, at least at 1 day after treatment (DAT), the number of virus transmission archlets on plants treated with Composition 18 as determined by EPG is significantly lower compared to that on untreated control plants.

TABLE 11

No. of virus transmission archlets as determined by EPG[a]

| Treatment/ formulation | Rate product/A | # of archlets ± se 1 DAT | 4 DAT | 7 DAT |
|---|---|---|---|---|
| UTC | — | 16 ± 2 a | 14 ± 2 a | 15 ± 1 a |
| C 18 | 0.5% vol/vol | 3 ± 1 b | 12 ± 3 a | 14 ± 4 a |

[a]Means followed by the same letter within columns are not significantly different (P > 0.05; REGWQ).

Conclusion

In this experiment, Composition 18 does not directly kill the aphids when it was applied to foliage that had been treated 24 hours earlier. The lower rate of virus transmission by aphids to the plants at 1 DAT on the plants compared to untreated control plants is due to the sublethal effects of Composition 18 on feeding behavior of aphids, which means Composition 18 at 0.5% v/v concentration can prevent, inhibit and/or repel aphids feeding on plants for at least 1 day.

Example 3

Efficacy of Exemplary Biopesticidal Composition 18 in Inhibiting Psyllid

Treatments

The treatments and rates compared are given in Table 12. These application rates were approximated by proportionally scaling down field rates for individual 2 foot long citrus tree branches. Each branch was sprayed with treatment solutions until run-off using a hand-held atomizer.

TABLE 12

Treatments and Rates

| Treatment | Rate |
|---|---|
| Untreated | |
| Danitol | 16 fl oz/a |
| Composition 18 | 4 qt/a |
| Composition 18 + Citrus Oil 435 | 4 qt/a, Citrus Oil 435 (2% v/v) |
| Citrus Oil 435 | 2% v/v |

Experimental Design

An experimental unit consisted of a tree branch on a mature flushing 'Valencia' tree. Each treatment was applied to six replicate tree branches, which were subsequently enveloped with mesh sleeve cages. Mesh cages were maintained over treatments either for the duration of the experiment or for 6 hour weekly periods.

Results

Psyllid mortality was tested. After application of treatments and caging of treated branches, 50 adult psyllids (4-8 days old) were released into each mesh sleeve cage. Cages were carefully removed 3, 7, 14, and 21 days after application when all dead psyllids that could be found were counted and removed. As shown, only treatment of danitol killed almost 100% after 7 DAT, while there was no significant difference between untreated control plants and plants treated with Composition 18 along or mixture of Composition 18 and citrus oil. After counting, cages were replaced over treated branches. Cumulative psyllid mortality over the course of the experiment was recorded.

Psyllid repellency was also tested. Three days after treatments were applied to branches, which were flagged for identification, all treated branches were sleeved as described above and 50 psyllids were released per sleeve cage between 8:00 AM and 9:00 AM. Six hours later, all psyllids that could be found on tree branch foliage or branches were counted and removed. Those psyllids found in cages but not on branches were also counted. Sleeves were carefully and slowly removed during this process. Psyllid repellency was measured by comparing the mean number of psyllids that were alighting on treated branches per treatment. This procedure was repeated on the 7th, 14th, and 21st day following application of treatments to tree branches. Although the majority of the total 50 psyllids per replicate treatment were accounted for, this procedure did not allow for 100% recovery of released psyllids. FIG. 1 shows the results. As it indicates, at 3 DAT, plants treated with Composition 18 alone or mixture of Composition 18 and citrus oil have significantly reduced mean number of psyllids found on foliage per caged branch compared to plants treated with citrus oil or untreated control.

Conclusion

Composition 18 causes citrus psyllid repellency for at least 3 days.

Example 4

Repellency of Mites Using Exemplary Biopesticidal Composition 18

Experimental Design

Biopesticidal experiments to evaluate repellency of mites by exemplary composition provided by present invention were conducted in the greenhouse. A two spotted spider mite colony maintained in the laboratory was used in all experiments. Two-spotted spider mites reproduce extremely fast and can overwhelm plants by sheer numbers. Leaves of plants infested with spider mites show a distinct spotted effect called stippling (or stipple). Spider mites cause stippling because they feed on plant cells one at a time.

Figure 2:
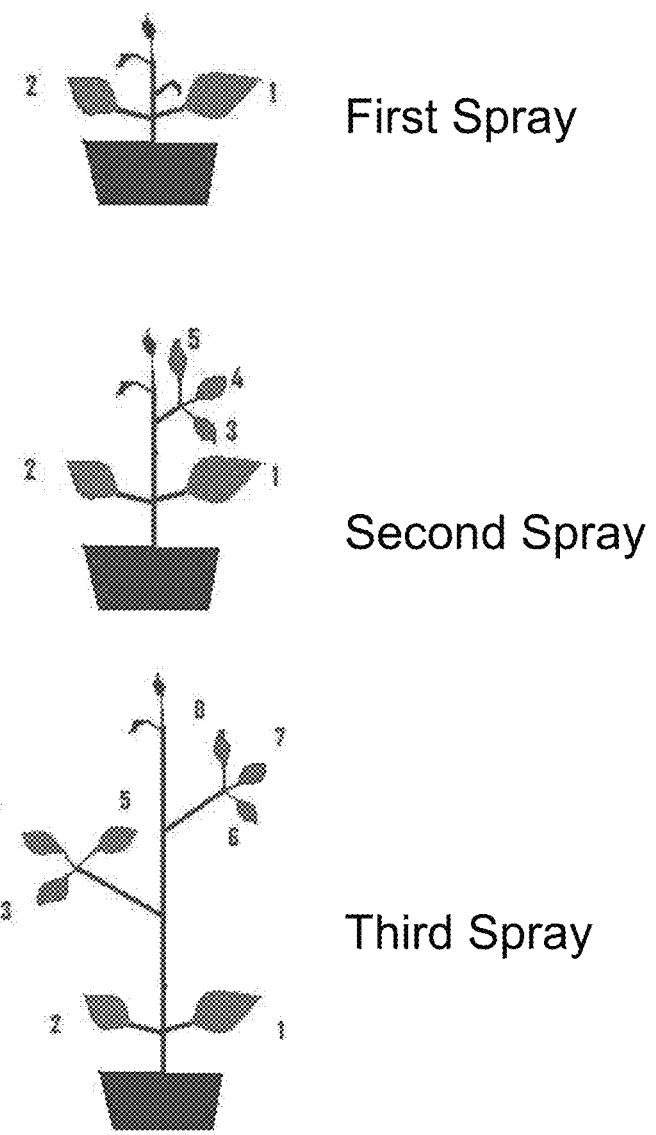
FIG. 2 represents the plant development stages upon each spraying, and way of numbering each bract.

40 pots of one-week-old Lima bean plants equilibrated by size and reduced to three to four plants per pot were used for experiment. Each 10 pots of lima bean plants was designated as a treatment group. These four treatment groups included a group of untreated control ("UTC") plants, and groups of plants sprayed with diluted Composition 18 (1%, v/v) once, twice, or three times before infesting with two spotted spider mites, respectively. Multiple sprays were done on a five-day interval. To infest lima plants, two inoculation leaves were placed on leaves of the 1st and the $2^{nd}$ bracts (equal to the first and the second true leaves, see FIG. 2) of UTC plants or plants treated with Composition 18 after all sprays were done. Each inoculation leaf provided about 50 to about 100 two spotted spider mites. FIG. 2 shows the plant development stages upon each spray, and method of numbering each bract.

Results

At 7 days after infection treatment ("DAT", the same date as the third spray was done), one leaf from the $5^{th}$ bract was harvested and counted for both the total number of two spotted spider mites, and the stipple number on leaf At 7 DAT, there was no significant difference between the number of total mites on the leaves from the 5th bract of UTC plants and that of plants sprayed with Composition 18 once, twice or three times, and there was no significant difference among groups in terms of stipple number, either.

Figure 3:
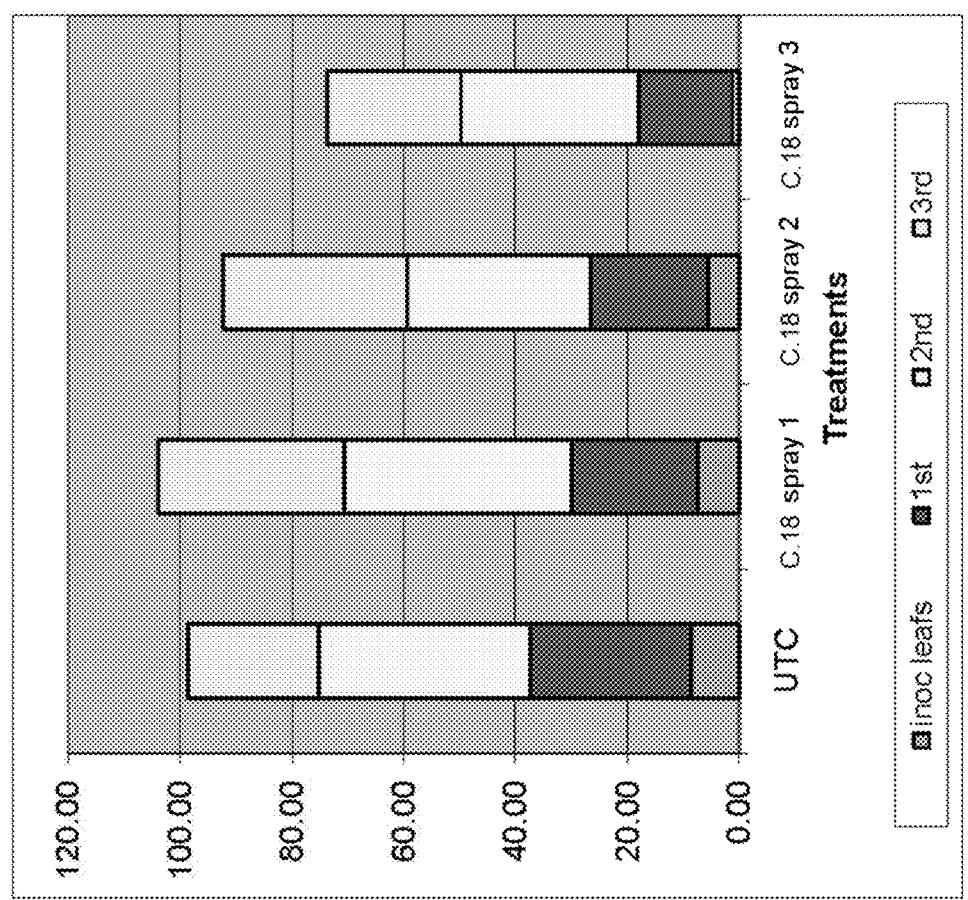
FIG. 3 represents distribution of two spotted spider mites on inoculation leaves, and the leaves of the $1^{st}$, $2^{nd}$, and the $3^{rd}$ bracts of each treatment group (UTC, C.18 spray 1, C.18 spray 2, and C.18 spray 3), counted at 10 DAT.

To evaluate if mites avoid the treated plant leaves, at 10 DAT, stipple numbers on inoculation leaf and leaves from the $1^{st}$, $2^{nd}$ and $3^{rd}$ bracts in each treatment group were counted. As FIG. 3 shows, the total number of stipples on leaves of plants sprayed twice or three times with diluted Composition 18 is lower compared to UTC. In addition, FIG. 3 shows that spider mites avoided the treated plant leaves. For example, total stipple number on the leaves of the $1^{st}$ and the $2^{nd}$ bracts of plants sprayed with Composition 18 once (C. 18, Spray 1) was lower than that of the UTC, which is consistent with more stipples on the leaves of the $3^{rd}$ bract in C. 18 spray 1 compared to UTC. This trend can be also observed in plants sprayed twice or three times before infesting (see FIG. 3).

At 10 DAT, the plant height was measured, leaves number was counted, and the average percent of plant stipple for each treatment group was calculated. There was no significant difference in terms of average percent of total plant stipple, plant height or number of leaves, respectively, suggesting that there are no fitness (i.e., physiological and/or phenotypical) costs for plants sprayed with diluted Composition 18.

Conclusion

Applying Composition 18 resulted in two spotted mite repellency for at least 10 days, without any fitness costs to lima bean plants.

Example 5

Evaluation of Composition 17 to Manage Watermelon Vine Decline (WVD) Caused by Squash Vein Yellowing Virus (SqVYV)

Composition 17 is as follows:

|  | C. 17 |
| --- | --- |
| Compound in wt % | Total 100% |
| α-Terpinene | 10 |
| p-Cymene | 3.75 |
| limonene | 3 |
| Total terpene in wt % | 16.75 |
| Canola oil (volume filler) in wt % | 8.25 |
| Canola oil (carrier) | 37.5 |
| Steposol SB-W ® (carrier) | 25 |
| Tween 80 (emulsifier) | 7.5 |
| SUSTAIN ® | 5.0 |

In the fall of 2009, a field trial will be conducted to evaluate the efficacy of Composition 17 to manage WVD caused by SqVYV transmitted by whiteflies. There will be three treatments for evaluation purposes which are listed in Table 13 below:

TABLE 13

| Treatments and Rate (1) | |
| --- | --- |
| Treatment | Rate |
| Untreated (UTC) | |
| Standard grower treatment* | See below |
| Standard grower treatment + Composition 17 | Composition 18: 2.0 qt/a |

*Standard grower treatment is characterized as: Admire Pro 10.5 oz/a at transplanting; week 1: Fulfill 8 oz/a, week 2: Fulfill 8 oz/a, week 3: Thionex 0.67 qt/a, week 4: Thionex 0.67 qt/a, week 5: Oberon 8.5 oz/a, week 6: Oberon 8.5 oz/a, week 7 & 8: no insecticide, week 9: Thionex 0.67 qt/a, week 10: Knack 10 oz/a, week 11: no insecticide, week 12: Thionex 0.67 qt/a Watermelon seedlings will be transplanted into fine sand. Treatment will be arranged in a randomized complete block design with 3 replications. Each replicate will consist of 2 rows 240 ft in length. Each plot will consist 10 plants spaced 36 inches, apart within in 27 ft of row with 10 ft between each plot and 12 ft between each row.

Whiteflies will be counted weekly starting 30 days after transplanting in each plot. Plants will be evaluated for disease severity (percentage of plant tissue affected) and also the type of WVD-associated symptoms such as yellowing, wilting, and tissue death, at 7 to 14 days intervals. The disease rating scale will be 0 through 5 as described below:
  0=healthy;
  1=foliage exhibiting yellowing;
  2=yellowing of foliage and wilting;
  3=yellowing, wilting, and necrosis (death) exhibited on one or more runners;
  4=most of the plant affected by all the symptoms of vine decline including more than 50% of plant dead;
  5=plant dead.

Disease incidence, or the number of plants exhibiting symptoms of vine decline regardless of severity will be determined. Fruit will be harvested and the number and weight per plot recorded. The fruit will be dissected and interior symptoms of vine decline on fruit will be taken using a disease rating based upon a 0 to 5 scale:

0=no fruit symptoms,
1=slight necrosis of rind only,
2=rind necrosis and slightly discolored flesh,
3=extensive rind necrosis and discolored flesh;
4=extensive rind necrosis and necrosis of flesh;
5=fruit completely rotten including discoloration and rotted flesh.

Mean rating and total fruit weight will be statistically evaluated. As one can expect, the result will show that at 45 days after treatment, approximately 35% of the plants in the UTC exhibit symptoms of WVD compared to approximately zero plants will show symptoms in the two other test treatments. It is expected that at 60 days after treatment, approximately 60% of the plants in the UTC exhibit symptoms compared to approximately 25% for the grower standard and approximately 0% for the Composition 17+grower standard treatment. At 75 DAT, approximately 90% of the plants in the UTC are expected to exhibit symptoms compared to approximately 65% for the grower standard and approximately 15% for the Composition 17+grower standard treatment. At 90 DAT (at harvest), 100% of the plants in the UTC and the grower standard treatment will be expected to exhibit symptoms compared to only approximately 25% for the Composition 17+grower standard treatment. These differences will most likely be statistically significant.

It is also expected that there will not be significant effect in adult whitefly counts per leaf over the entire period from approximately 30 days after transplanting to the end among all treatments. Fruit will be harvested and the number and weight per plot will be recorded. In addition, it is expected that both insecticide treatment programs will significantly increase yields compared to the UTC, while Composition 17+grower standard treatment will have a higher yield compared to grower standard treatment. These differences will most likely be statistically significant.

The results are expected to show that instead of killing whiteflies, Composition 17 will repel whiteflies feeding on plants, thus prevent Watermelon Vine Decline caused by Squash vein yellowing virus.

An experiment was conducted in the southeastern United States that was very similar to the above prophetic example. Specifically, watermelon seedlings were transplanted into fine sand. Treatments were arranged in a randomized complete block design with four replications. Each replicate consisted of 2 rows of 5 plants each spaced 36 in. in a 12 ft plot within each row. There were 10 ft between each row with a 10 ft buffer between each plot. Treatments and spray schedules are given in Table 14.

TABLE 14

Treatments, rates and application dates.

| Treatment | Description | Rate | Week of Application[x,y] |
|---|---|---|---|
| 1 | Untreated control | | |
| 2 | Admire | 10.5 oz/A | O |
|   | Fulfill | 2.75 oz/A | 1, 2 |
|   | Thionex | 1.33 qt/A | 3, 4, 5, 6 |
|   | Oberon | 8.5 oz/A | 7 |
| 3 | Actigard 50WG | 0.75 oz/A | A, C, E, G |
| 4 | Actigard 50WG | 0.75 oz/A | C, E, G |
|   | Admire | 10.5 oz/A | O |
|   | Fulfill | 2.75 oz/A | 1, 2, |
|   | Thionex | 1.33 qt/A | 3, 4, 5, 6 |
|   | Oberon | 8.5 oz/A | 7 |
| 5 | Cabrio | 16 oz/A | C, E, G |
|   | Bravo Weatherstik 6SC | 2 pts/A | A, B, D |
| 6 | Cabrio 20EG | 16 oz/a | C, E, G |
|   | Bravo Weatherstik 6SC | 2 pts/a | A, B, D |
|   | Admire | 10.5 oz/A | O |
|   | Fulfill | 2.75 oz/A | 1, 2 |
|   | Thionex | 1.33 qt/A | 3, 4, 5, 6 |
|   | Oberon | 8.5 oz/A | 7 |
| 7 | Admire | 10.5 oz/A | O |
|   | Fulfill | 2.75 oz/A | 1, 2 |
|   | Composition 17 | 2 qt/A | 3, 4, 5, 6, |
|   | Oberon | 8.5 oz/A | 7 |
| 8 | Admire | 10.5 oz/A | O |
|   | Fulfill | 2.75 oz/A | 1 |
|   | Composition 17 | 2 qt/A | 2, 4, 6 |
|   | Movento | 5.0 oz/A | 3 |
|   | Oberon | 8.5 oz/A | 5, 7 |

[y]Insecticide application dates: 0 = transplanting; 1 = 16 days after transplanting (DATr); 2 = 22 DATr; 3 = 29 DATr; 4 = 36 DATr; 5 = 43 DATr; 6 = 50 DATr; 7 = 57 DATr
[x]Other sprays: on A = 8 DATr; B = 14 DATr; C = 21 DATr; D = 28 DATr; E = 35 DATr; F = 42 DATr; G = 49 DATr Disease rating of the plants and the fruit, after harvested, were assessed on the scales described above. All insecticide treatments except treatment 8 yielded significantly fewer adult whiteflies than the untreated control. Each of the three different insecticide rotation treatments evaluated for nymphs (2, 7 and 8) resulted in significantly reduced total numbers of nymphs compared to the untreated control. Disease severity ratings for various treatments and a summary of fruit data collected after harvest are shown in Tables 15 and 16, respectively.

TABLE 15

Disease severity rating for management of Squash vein yellow virus on watermelon.

| | Mean Disease Rating | | |
|---|---|---|---|
| Treatment # | 42 days after transplant | 58 days after transplant | 64 days after transplant |
| 1 | 0.15 | 1.91 b | 3.36 ab |
| 2 | 0.10 | 1.20 c | 2.33 c |
| 3 | 0.10 | 1.50 bc | 3.22 b |
| 4 | 0.11 | 0.90 c | 2.16 c |
| 5 | 0.33 | 1.90 b | 3.63 ab |
| 6 | 0.10 | 2.82 a | 3.90 a |
| 7 | 0.36 | 1.21 c | 2.21 c |
| 8 | 0.10 | 1.05 c | 2.00 c |
| | 0.4559 | .0001 | .0001 |

[t]Disease severity ratings based on scale of 0-5 where 0 = no symptoms of vine decline and 5 = plant dead.)

TABLE 16

Summary of Fruit Data

| Treatment # | Mean Fruit Number per Plot | Mean Fruit Weight per Plot (lb) | Fruit Rating (0-5 scale) |
|---|---|---|---|
| 1 | 13.5 | 154 | 1.93 ab |
| 2 | 13.8 | 186 | 1.55 b |
| 3 | 14.3 | 168 | 2.13 ab |
| 4 | 18.0 | 249 | 1.82 ab |
| 5 | 11.3 | 91 | 1.87 ab |
| 6 | 12.5 | 143 | 2.26 a |
| 7 | 15.0 | 209 | 0.71 c |

TABLE 16-continued

Summary of Fruit Data

| Treatment # | Mean Fruit Number per Plot | Mean Fruit Weight per Plot (lb) | Fruit Rating (0-5 scale) |
|---|---|---|---|
| 8 | 13.3 | 160 | 2.42 a |
| P = | 0.7025 | 0.5133 | 0.0001 |

*Columns without letters or followed by the same letter are not significantly different at P value indicated.

Example 6

Evaluation of Composition 17 to Manage Disease Caused by Potato Virus Y (PVY)

I. Treatments.

In the fall of 2009, a field trial will be conducted to evaluate the efficacy of Composition 17 to manage disease caused by PVY transmitted by aphids. There will be three treatments for evaluation purposes which are listed in Table 17 below:

TABLE 17

Treatments and Rate (2)

| Treatment | Rate |
|---|---|
| Untreated (UTC) | |
| Standard grower treatment* | See below |
| Standard grower treatment + Composition 17 | Composition 17: 1.7 qt/a every 3-4 days |

*Standard grower treatment is characterized as: Spray once aphids are observed: Assail 1.7 oz/a on about July 17; Beleaf 2.8 oz/a on about July 30; Fulfill 5.5 oz/a on about August 3; Provado 3.8 oz/a on about August 18; Assail 1.7 oz/a on about August 30; Monitor 1 qt/a on about September 20

II Plot Size.

Dimensions:

24 ft rows×36" row (4 rows/plot)=540 ft²/plot 540 ft²/plot×48 plots experimental replicates separated by 3, 20' alleys total experiment size=0.6 acres Cultivar:

Treatment rows will consist of plant rows of virus-free *S. tuberosum*.

III. PVY Transmission

Transmission of Potato virus Y will be established by aphids feeding. Aphids will be introduced on plants after germination.

III. Treatment Evaluations.

Aphid counts per plant over the entire period will be determined. Incidence of PVY will be surveyed monthly by counting all symptomatic plants, and their relative position in each experimental plot. Total plot yield will be determined at the conclusion of the experiment from each plot.

IV. Expected Results.

It is expected that there will be no significant treatment effect difference in aphid counts per plant over the entire period among all treatments.

It is also expected that at about 30 days after introduction of aphids, approximately 5% of the plants in the UTC and the standard grower treatment exhibit symptoms of PVY, compared to no plants showing symptoms in Composition 17 treated plots. At 60 days, it is expected that approximately 20% of the plants in the UTC and the standard grower treatment will exhibit symptoms compared to approximately 2% for the Composition 17 treatment. At 90 days, approximately 35% of the plants in the UTC and grower standard are expected to exhibit symptoms compared to approximately 5% for the Composition 17 treated plots.

The results are expected to show that instead of killing aphids, Composition 17 will repel aphids feeding on plants, thus prevent disease caused by Potato Virus Y.

V. Actual Results from Similar Trial.

A potato trial was conducted consisting of four treatments, shown in Table 18 below, and one control replicated four times in a randomized complete block design. Individual treatment plots were four rows wide by 25 ft. long with 5 ft. alleyways separating the plots. The experiment was planted using machine-cut potato seed G2 *Solanum tuberosum* L., Cv: "Russet Burbank." Potato aphids from naturally occurring populations and green peach aphids introduced in the center two rows of each individual test plot 54 days after planting were counted periodically. Insecticides were applied 61 days after planting. ELISA tests were conducted on five randomly selected plants per plot before and 30 days after insecticide application to determine presence of potato virus Y (PVY).

TABLE 18

Treatment List

| Treatment # | Treatment | Rate/Acre |
|---|---|---|
| 1 | Untreated Control (UTC) | |
| 2 | Composition 17 | 32 oz. |
| 3 | Composition 17 | 64 oz. |
| 4 | Composition 17 | 96 oz. |
| 5 | BELEAF + NIS | 2.8 oz.; 0.25% V/V |

The lowest total cumulative number of green peach aphids after the insecticide applications was recorded in T5 (Beleaf). The cumulative number of aphids after the insecticide application for the three Composition 17 treatments decreased with the increase in the rate of the treatment and the lowest number was present at the highest rate (T4). The cumulative number of aphids for T2 and T3 was not different from the one in the UTC.

As with the green peach aphids, the cumulative number of potato aphids after the insecticide application for the three Composition 17 treatments decreased with the increase in the rate of the treatment and the lowest number was present at the highest rate (T4). The lowest total cumulative number of aphids after the insecticide applications was recorded in T5 (Beleaf). However, this number was not significantly different from the one in T4 (the highest rate of Composition 17). The cumulative number of aphids for T2 (lowest rate of Composition 17) after the application was not different from the one in the UTC.

No PVY infection was found at plant emergence in any of the plots. This indicated that the seed material in general had no detectable infection. ELISA sampling at 30 days after insecticide treatment indicated that T1 (UTC), T2 and T3 had 25% PVY infection. The high rate of Composition 17 reduced the percentage of PVY infection to 15%. Beleaf (T5) was the only treatment with no detectable level of infection at the last ELISA testing.

Example 7

Laboratory Screen for Activity of Plant-Extract Based Composition

This example provides a laboratory screen indicating the activity of the plant-extract based formulated composition C16. C16 contains 25% of C11 as active ingredient, 35% of a vegetable oil as carrier and 40% of other carrier/solvent, emulsifier, and spreader.

C16 was tested in initial screens which were high throughput, microtitre plant-based assays. The targets include:

Blatella germanica (Orthoptera: German cockroach nymphs),

Musca domestica (Diptera: House fly pupa/adults),

Tetranycus urticae (Acari: two spotted spider mites on leaf disks),

Spodoptera exigua (Lepidoptera; beet army worm eggs/larvae on artificial diet)

Diabrotica undecimpunctata (Coleoptera; Western spotted cucumber beetle eggs/larvae on artificial diet), and Caenorhabditis elegans (a mixed age culture of free living round worms in liquid suspension).

The targets were challenged with a serial dilution of C16 starting with a 3% v:v solution in water. A chemical control plate was run for each target assay on each experimental date.

For the beet armyworm assay, caterpillar eggs were used as the target "insect". Eggs were held and temporally synchronized, then washed, sterilized, and suspended in an egg:agar solution. Serially diluted test solutions, C16 in water, were overlaid onto the surface of artificial diet in a 96 well plate format and dried. The eggs were placed on top of the test solution and then dried quickly under forced air. The plates were heat sealed with perforated transparent Mylar and incubated at 28° C. Mortality was evaluated after five days. Ovicidal compounds resulted in dead eggs. Larvacidal activity was evaluated as contact (small dead neonates) or intoxication (death, stunted growth, moulting disruption, etc).

In the high throughput assay, the mortality was rated visually using an index where a rating of:

1—indicates 100% mortality (Active) and a rating of 4 indicated growth equal to untreated controls (Inactive).

2—indicates less than 100%, but greater than 50% mortality.

3—indicates it was less than 50%, but greater than 10% mortality.

Figure 4:
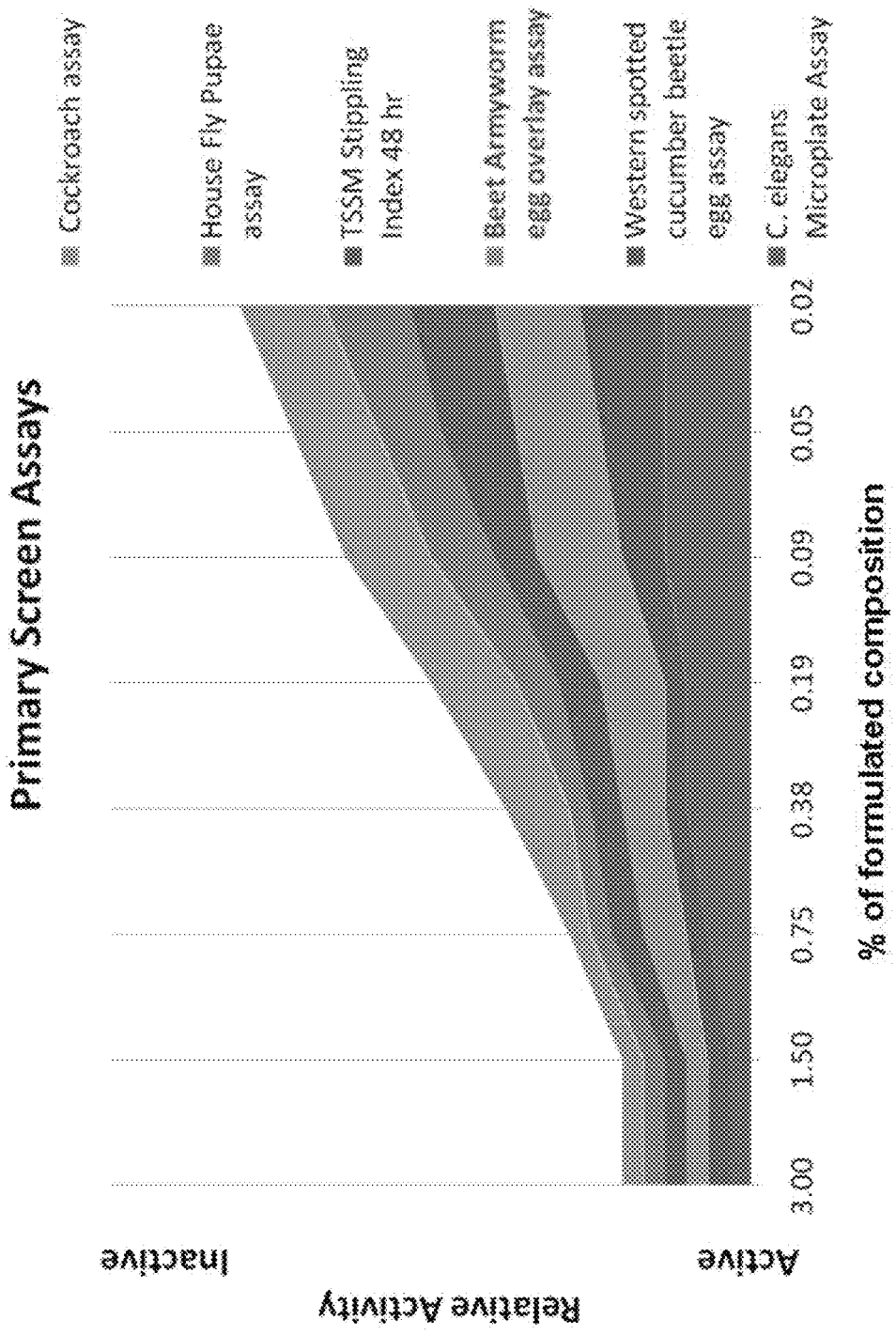
FIG. 4 depicts relative activity of C16 against screening insect targets.

FIG. 4 shows the relative activity of C16 in order of sensitivity (e.g., C. elegans was most sensitive). Serial dilutions of the chemical control yielded a dose response. The data illustrates that C16 is effective in controlling beet armyworm egg in the laboratory overlay assay.

Example 8

Laboratory Study of Activity of Individual Components of Synthetic Blend Based Composition Against Beet Armyworm The potency of the individual active ingredients in a synthetic blend-based composition C13 was estimated using a quantitative caterpillar egg assay, similar to the screening assay described herein. C13 contains 25% of C1 as active ingredient, 37.5% of the carrier (vegetable oil, in this formulation), 37.5% of other carrier/solvent, emulsifier, and spreader (see Table 3 and 4 for the compositions of C1 and C13, respectively).

Study Objective

The objective of this study was to evaluate the effects of synthetic blend-based composition C13 and each of its primary terpenes against lepidoptera eggs (Spodoptera exigua) in a laboratory assay that mimics contact activity on a leaf surface in the field. This was done by estimating the $LC_{50}$ of the solvent/carrier (in this instance, vegetable oil) and the three primary terpenes alone, and comparing those values to the estimated $LC_{50}$ of C13.

Method

Direct Contact Overlay LC Assay

A requirement of the Probit model used to estimate the $LC_{50}$ is that there should be a dose response with two rates above 50% mortality and two rates below 50%. Because of their solubility it was not possible to get this with a neat solution of oil or terpenes so, a series of preliminary assays were conducted to find a suitable carrier, testing solutions compatible with the terpenes and carrier. To achieve a stable emulsion of the individual terpenes that could be pipetted across a suitable range of concentrations, it was decided to use a universal diluent containing 0.25% Tween™ 81. Stock solutions of C13 (see Table 4, which include the simulated blend C1 (Table 3)) were diluted to a starting concentration of 25% v:v in deionized water containing 0.25% Tween™ 81.

Treatments tested:
1. α-terpinene at 10%, diluted in 0.25% Tween 81
2. d-limonene at 3%, diluted in 0.25% Tween 81
3. p-cymene at 3.75%, diluted in 0.25% Tween 81
   (The above concentrations represent approximately 25% of the concentrations found in natural plant extract of Chenopodium ambrosioides near ambrosioides for each terpene, as final product is a 25% emulsifiable concentrate).
4. C13 at 25% (at higher concentrations the effects are too strong to distinguish differences)
5. Carrier was tested at 45.75% (the total concentration found in C13 (8.25% in active ingredient (also referred to as "active ingredient" or "ai" elsewhere herein) plus 37.5% in product), diluted in 0.25% Tween 81.
6. Positive control: Javelin WG (Bacillus thuringiensis).
7. Negative control (blank): 0.25% Tween 81.

Stock solutions were transferred to deep, 96-well, microtitre plates. 1.4 ml of each stock solution was placed in the 2 ml wells that ran across the top row of the deep well plate (Row A; wells 1-12, see Table 15). A digital 12-channel Matrix pipette was then used to add 700 uls of 0.25% Tween 81 in deionized water (DI $H_2O$) to the remaining wells (Rows B-H; 1-12). The 12 channel pipette was used to perform serial dilutions by mixing, aspirating, and then dispensing 700 ul of each stock solution from row A into the adjoining 700 ul of diluent in row B. This process was repeated seven times to give a final concentration of eight, 50% serially diluted samples containing 700 µl.

The relative concentrations tested for each of the 5 test substances and the controls are given in Table 19.

TABLE 19

The relative concentrations tested for each of the 5 test substances and the controls

| Row | α-terpinene % | d-limonene % | p-cymene % | C13 % | Carrier | Other carrier/solvent, emulsifier, and spreader/binder |
|---|---|---|---|---|---|---|
| A | 10 | 3 | 3.75 | 25 | 45.75 | 1000 |
| B | 5 | 1.5 | 1.87 | 12.5 | 23.75 | 500 |
| C | 2.5 | 0.75 | 0.94 | 6.25 | 11.87 | 250 |
| D | 1.25 | 0.37 | 0.47 | 3.125 | 5.94 | 125 |

TABLE 19-continued

The relative concentrations tested for each of the 5 test substances and the controls

| Row | α-terpinene % | d-limonene % | p-cymene % | C13 % | Carrier | Other carrier/ solvent, emulsifier, and spreader/ binder |
|---|---|---|---|---|---|---|
| E | 0.625 | 0.18 | 0.23 | 1.56 | 2.97 | 62.5 |
| F | 0.31 | 0.93 | 0.12 | 0.78 | 1.48 | 31.2 |
| G | 0.16 | 0.47 | 0.06 | 0.39 | 0.74 | 15.6 |
| H | 0.78 | 0.23 | 0.03 | 0.195 | 0.37 | 7.80 |

An eight channel Matrix pipette was then used to mix, aspirate and distribute all eight of the serial dilutions from the deep well plate to a labeled 96 well plate containing a wheat germ/casein-based artificial diet. Aliquots containing 240 μl of each dilution were aspirated and 40 μl were dispensed into to six wells across the surface of the microtitre plate containing 200 μl of artificial diet/well. Two samples were tested on every plate with the one sample in rows A through H—columns 1 to 6, and the second sample in wells A through H columns 7 to 12. The last two samples in each assay contain the Javelin standard and 0.25% Tween in DI water as the untreated controls.

The samples were then dried under forced air at room temperature. This deposits a thin film of the treatment on the surface of the diet much the same way as applying a spray solution to a leaf surface. Once the plates were dried, then eggs were put in each well using a Matrix pipette with 5-10 temporally synchronized caterpillar eggs suspended in 20 μl of a 0.1% agar solution. This rehydrates the surface film and then the egg:agar was dried under forced air, a second time. Once the agar solution was dry the plates were heat sealed with a perforated Mylar film that seals the insects in the well, but allows for gas exchange. The plates were incubated at 28° C. on a 16:8 light: dark cycle. After five days the numbers of live insects in each row were recorded. Mortality was recorded as the number dead over the number treated and expressed as control corrected percent mortality. The $LC_{10}$, $LC_{50}$, and $LC_{90}$ were calculated using natural response and 95% confidence intervals.

Results

Results are summarized in FIG. 5 and Table 20.

TABLE 20

The estimated $LC_{50}$s when the samples were run as a nested set using probit analysis, calculating the slope, and the 95% confidence intervals.

| Treatment Initial Concentration | AVG $LC_{50}$ | Std Dev | Estimated $LC_{50}$ | Limits | Slope | g value |
|---|---|---|---|---|---|---|
| α-terpinene 10% | 4.336 | 2.13 | 4.776 | 3.847 to 6.209 | 2.150 +− 0.122 | 0.048 |
| d-limonene 3.00% | 2.093 | 1.48 | 1.905 | 1.524 to 2.553 | 2.160 +− 0.136 | 0.063 |
| p-cymene 3.75% | 1.539 | 1.14 | 2.682 | 1.635 to 6.261 | 1.371 +− 0.084 | 0.139 |
| C13 25% | 1.167 | 0.76 | 0.998 | 0.820 to 1.207 | 2.489 +− 0.111 | 0.04 |
| Carrier 45.75% | 3.082 | 1.46 | 2.918 | 2.156 to 3.933 | 2.282 +− 0.142 | 0.076 |

Table 21 shows relative activity of the individual components (AIs) compared to C13.

TABLE 21

Relative Activity of the individual components compared to C13

| Compound | % | LC 50 | 1% solution % in the tank | Times |
|---|---|---|---|---|
| C13 | | 0.998 | | |
| α-terpinene | 10 | 4.776 | 0.1 | 48X |
| d-limonene | 3 | 1.905 | 0.03 | 64X |
| p-cymene | 3.75 | 2.682 | 0.0375 | 72X |
| Carrier | 45.75 | 2.918 | 0.4575 | 6X |

Discussion

The complete mixture of C13 was significantly more lethal than the individual components, with an estimated $LC_{50}$ of 0.998%, and non overlapping 95% CIs of 0.820 to 1.207.

The active ingredients in C13 are a blend of terpenes and carrier whose combined activity is a function of their relative proportions within the mixture. For example, the relative proportion of α-terpinene in C13 is 10% of the total. The estimated $LC_{50}$ of C13 blend is 0.998%. If α-terpinene accounts for 10% of this activity, this translates to an $LC_{50}$ of only 0.0998%. Thus the 10% α-terpinene in $LC_{50}$ is significantly more active as a component in the blend given that when α-terpinene is used alone the $LC_{50}$ was estimated at 4.77%. The α-terpinene in the blend is 48 times more active than when tested alone.

A similar pattern is seen with d-limonene and p-cymene. When tested alone, the lethal concentration of d-limonene and p-cymene were estimated at 1.9% and 2.68% respectively. The relative proportion of these two terpenes in the C13 blend is 3% and 3.75% respectively. Based on the estimated $LC_{50}$ for C13, the 0.3% associated with d-limonene was 64 times more potent in the mixture. The proportion of the p-cymene in the mixture was 72 times more potent in the mix than alone. These data indicated that the efficacy of the active ingredients in the mixture were 40 to 70 times more active than the individual components alone.

Vegetable oil $LC_{50}$ is 2.9% and C13 is composed of 47.5% vegetable, then the projected vegetable oil $LC_{50}$ in C13 is 0.475×0.998=0.474%. Vegetable oil seems to behaves the same whether a stand alone or in the mixture. Vegetable oil is considered to have a physical mode of action only.

Conclusions

As for the plant extract, the data seems to support that the effectiveness of C13 is dependent on the activity of all three terpenes in combination.

Example 9

Control of Melonworm in Squash

Squash was seeded in a Rockdale soil in the Southeastern part of the United States of America. A Randomized Complete Block ("RCB") design was employed to provide 4 replicates each for eight treatments comprising a plot size of 2 rows, 30 ft. long. Application of all treatments was initiated after the appearance of melon worms on squash. All insecticides were applied foliarly on four dates—April 26, May 3, May 13 and May 21 by using a backpack sprayer with two nozzles per row at 30 psi delivering 70 gpa. No phytotoxicity was observed with any of the treatments. Evaluation of treatments was conducted 24 h after each application on April 26, May 3, May 13 and May 21 by thoroughly checking 10 randomly selected plants in each treatment plot for melonworm larvae. Melonworm feeding damage was rated by visually scoring squash plants in a plot on a scale of 0 to 6, where 0 stands for plants having more than 80% damage and 6 stands for plants with no damage. Numbers of marketable fruits were recorded by harvesting all fruits on randomly selected 10 plants/treatment plot. Data were analyzed with ANOVA and mean separation used the Duncan Multiple Range Test (DMRT).

All insecticide treatments significantly reduced melonworm larvae on squash plants when compared with the nontreated control (Table 18). Accordingly, insecticide treatments significantly increased foliage quality of squash by reducing feeding damage when compared with the non-treated control (Table 22). Mean numbers of fruits/10 squash plants were also significantly higher on treated plants than the non-treated control plants.

TABLE 22

Control of Melonworm in Squash

| Treatment | Rate oz/acre | Mean number of melon worms per squash plant | | | | | | Damage rating$^z$ | No. fruit/10 plants$^x$ |
|---|---|---|---|---|---|---|---|---|---|
| | | April 20 | April 27 | May 4 | May 14 | May 22 | Mean | | |
| Control | | 1.05a | 3.05a | 3.80a | 2.40a | 3.60a | 2.70a | 3.25b | 4.75b |
| Rimon | 12.0 | 1.00a | 0.55bc | 0.35b | 0.25b | 0.10b | 0.45b | 5.38a | 15.25a |
| C16 | 32.0 | 0.20b | 0.05d | 0.00c | 0.00b | 0.05b | 0.06e | 5.50a | 14.25a |
| Coragen | 5.1 | 0.70ab | 0.65b | 0.10bc | 0.10b | 0.00b | 0.31b-d | 6.00a | 14.00a |
| Radiant | 7.0 | 0.55ab | 0.20cd | 0.00c | 0.00b | 0.00b | 0.15de | 6.00a | 13.25a |
| Avaunt | 3.5 | 0.75ab | 0.20cd | 0.00c | 0.00b | 0.00b | 0.19c-e | 6.00a | 13.75a |
| Synapse | 3.0 | 1.00a | 0.70b | 0.05c | 0.05b | 0.00b | 0.36bc | 5.75a | 16.50a |
| Alverde | 16.0 | 0.65ab | 0.65b | 0.25bc | 0.15b | 0.05b | 0.35bc | 5.50a | 13.25a |

Means within a column followed by the same letter do not differ significantly (P > 0.05; DMRT).
$^z$Visually rated on a scale 0-6, where 0 is the plants with heavily damaged leaves and 6 is the plants with no feeding damage.
$^x$At the end of the season, all marketable fruits from randomly selected 10 plants/plot were collected.

Example 10

Control of Grape Leafhopper

Methods

The trial initiated against an underlying population of grape leaf hopper (LH), *Erythroneura bigemina*. A single application was made.

There were six treatments for evaluation purposes which are listed in Table 23 below. Six LH evaluations were made by counting and recording the number of hoppers per leaf on a sample of 5 randomly-selected leaves per plot (vine).

TABLE 23

Treatments and Rates (1)

| Treatment # | Description | Rate |
|---|---|---|
| #1 | Untreated control (UTC) | |
| #2 | C13 | 2 qt/a |
| #3 | C13 | 3 qt/a |
| #4 | C13 | 3 qt/a |
| #5 | C13 | 4 qt/a |
| #6 | Standard (Provado 1.6F (Imidacloprid)) | 3 qt/a |

Following a pre-count on the 0 DAT (day after treatment), evaluations were made on the 3 DAT, the 7 DAT, the 14 DAT, the 21 DAT, and the 28 DAT. The numbers of leafhopper nymphs reached peaks around 20 days after treatment. The results of these evaluations were presented in Table 24.

TABLE 24

Number of leafhopper nymphs per leaf

| | 0 DAT | 3 DAT | 7 DAT | 14 DAT | 21 DAT | 28 DAT |
|---|---|---|---|---|---|---|
| #1 Untreated | 13.8a | 15.3a | 25.8a | 53.6a | 60.8a | 13.1a |
| #2 C13 | 11.6a | 2.0b | 11.2ab | 23.7b | 35.9b | 5.7bc |
| #3 C13 | 9.9a | 1.5b | 2.3b | 8.9bc | 14.0bc | 4.1bc |
| #4 C13 | 10.4a | 0.8b | 2.2b | 9.4bc | 14.4bc | 4.1bc |
| #5 C13 | 11.2a | 1.5b | 4.8b | 20.6bc | 25.8b | 5.9b |
| #6 Standard | 10.9a | 0.3b | 0.0b | 0.0c | 0.0c | 0.5c |

Phytotoxicity evaluations were made at each post application LH evaluation, beginning on the 3-DAT and ending on the 28-DAT. The scale used to document phytotoxicity was from the protocol: a 0-10 scale where 0=no damage and 10=total tree damage. The results of these evaluations were presented in Table 25.

TABLE 25

Number of leaves with leafhoppers present out of 5 leaves

| | 0 DAT | 3 DAT | 7 DAT | 14 DAT | 21 DAT | 28 DAT |
|---|---|---|---|---|---|---|
| #1 Untreated | 5.0a | 5.0a | 5.0a | 5.0a | 5.0a | 5.0a |
| #2 C13 | 5.0a | 4.0ab | 3.8ab | 5.0a | 5.0a | 4.8ab |
| #3 C13 | 5.0a | 3.5ab | 3.0b | 5.0a | 5.0a | 4.8ab |
| #4 C13 | 5.0a | 2.5bc | 4.0ab | 5.0a | 5.0a | 3.8b |
| #5 C13 | 5.0a | 3.0b | 2.8b | 5.0a | 5.0a | 4.8ab |
| #6 Standard | 5.0a | 1.0c | 0.0c | 0.0b | 0.0b | 1.5c |

Results

In summary, compared to untreated control, above results indicate that C13 can significantly control grape leafhopper (*Erythroneura bigemina*).

Example 11

Control of Two-Spotted Spider Mites in Almonds

Methods

This almond trial was conducted in a commercial almond orchard located in west United States. The Almond trial received one broadcast application (see Table 10 for details of all treatments) with a tractor mounted FMC Airblast sprayer at 156.20 GPA. The almond test subplots were evaluated for the control of Two-Spotted Spider Mites, *Tetranychus urticae*. A pre-application evaluation was conducted on 0 DAT, followed by evaluations on the 3 DAT, the 7 DAT, the 14 DAT, the 21 DAT, the 28 DAT, and the 35 DAT.

TABLE 26

Treatments and Rates (2)

| Treatment # | Description | Rate |
|---|---|---|
| #1 | Untreated control (UTC) | |
| #2 | C13 | 2 qt/a |
| #3 | C13 | 3 qt/a |
| #4 | C13 | 4 qt/a |
| #5 | Standard (Fujimite 5EC (Fenpyroximate)) | 2 qt/a |

All subplots were evaluated for egg, immature mites, and adult Two Spotted Spider Mites. Evaluations were based on selecting a total of 10 leaves per replicate. The samples were placed in pre-labelled brown bags on blue ice. The leaves were brought back to the laboratory where they were brushed onto a clear glass plate with a sticky surface. The glass plate was then placed on a circular point transect template composed of dots that represented ten percent of the total surface area. This template was placed under a binocular microscope where the live Two-Spotted Spider Mites or eggs that touched a black dot on the circular point transect sheet was counted and recorded. This yielded the average number of live mites or eggs per leaf based on brushing ten leaves per replicate.

The data collected was then entered into the computer and subjected to a two-way analysis of variance complete with a Duncan's Multiple Range Test, (DMRT) at the 5% level of probability. The data represent the average number of mite eggs or motile mites per leaf per replicate and are averaged for four replicates per treatment. Any two means that are not followed by the same letter are deemed to be significantly different from each other. Additionally, the plots were evaluated for plant injury due to the application of the test material. This evaluation occurred at 7 DAT. The almonds trees were evaluated for phytotoxicity effects on a scale of 0 to 100 where 0=no injury to 100=total plant death or necrosis.

Results

The pretreatment counts indicated that the mite population was approaching an economic threshold for treatment. At the 3-DAT evaluation all of the treatments exhibited a knockdown of the mite eggs and motile forms while the untreated population continued to build. This trend carried forward through the 35-DAT evaluation. Tables 27 to 30 presents numbers of mite eggs per 10 leaves, numbers of mite juveniles per 10 leaves, numbers of mite adults per 10 leaves, and numbers of mite motiles per 10 leaves, respectively, on each observation point. As they show, all of the treatments were providing good suppression of live mites and eggs. Additionally, all of the treatments were statistically equal in their control and superior to the untreated check.

TABLE 27

Mean numbers of mite eggs per 10 leaves

| | 0 DAT | 3 DAT | 7 DAT | 14 DAT | 21 DAT | 28 DAT | 35 DAT |
|---|---|---|---|---|---|---|---|
| #1 Untreated | 11.5a | 11.25a | 12.25a | 0.0a | 10.0a | 8.25a | 7.5a |
| #2 C13 | 11.0a | 5.5b | 2.0b | 0.0a | 0.0b | 0.0b | 0.0b |

TABLE 27-continued

Mean numbers of mite eggs per 10 leaves

| | 0 DAT | 3 DAT | 7 DAT | 14 DAT | 21 DAT | 28 DAT | 35 DAT |
|---|---|---|---|---|---|---|---|
| #3 C13 | 11.5a | 6.0b | 2.5b | 0.0a | 0.0b | 0.25b | 0.75b |
| #4 C13 | 11.25a | 6.5b | 1.0b | 0.0a | 0.0b | 0.5b | 0.0b |
| #5 Standard | 10.75a | 5.75b | 0.75b | 0.0a | 0.25b | 0.5b | 0.25b |

TABLE 28

Mean numbers of mite juveniles per 10 leaves

| | 0 DAT | 3 DAT | 7 DAT | 14 DAT | 21 DAT | 28 DAT | 35 DAT |
|---|---|---|---|---|---|---|---|
| #1 Untreated | 8.0a | 13.5a | 9.0a | 7.0a | 7.75a | 8.5a | 5.75a |
| #2 C13 | 8.0a | 7.0b | 1.0b | 0.5b | 0.0b | 0.0b | 0.0b |
| #3 C13 | 8.0a | 7.0b | 0.0b | 0.75b | 0.0b | 0.25b | 0.5b |
| #4 C13 | 8.75a | 6.25b | 0.25b | 1.25b | 0.0b | 0.0b | 0.25b |
| #5 Standard | 8.0a | 6.5b | 0.25b | 2.5b | 0.5b | 0.25b | 0.0b |

TABLE 29

Mean numbers of mite adults per 10 leaves

| | 0 DAT | 3 DAT | 7 DAT | 14 DAT | 21 DAT | 28 DAT | 35 DAT |
|---|---|---|---|---|---|---|---|
| #1 Untreated | 3.0a | 12.5a | 8.0a | 8.0a | 2.25a | 1.0a | 2.75a |
| #2 C13 | 4.5a | 6.75a | 0.5b | 0.0b | 0.0b | 0.0b | 0.0a |
| #3 C13 | 2.5a | 7.0b | 0.0b | 0.5b | 0.0b | 0.0b | 0.0a |
| #4 C13 | 3.25a | 7.5b | 0.0b | 0.0b | 0.0b | 0.0b | 0.0a |
| #5 Standard | 3.75a | 8.25b | 0.0b | 0.25b | 1.0b | 0.0b | 0.0a |

TABLE 30

Mean numbers of mite motiles per 10 leaves

| | 0 DAT | 3 DAT | 7 DAT | 14 DAT | 21 DAT | 28 DAT | 35 DAT |
|---|---|---|---|---|---|---|---|
| #1 Untreated | 11.0a | 25.75a | 15.0a | 15.0a | 10.25a | 10.0a | 8.5a |
| #2 C13 | 12.5a | 13.75b | 0.5b | 0.0b | 0.0b | 0.0b | 0.0b |
| #3 C13 | 10.5a | 13.75b | 0.0b | 0.0b | 0.0b | 0.25b | 0.5b |
| #4 C13 | 12.0a | 13.75b | 0.0b | 0.0b | 0.0b | 0.0b | 0.25b |
| #5 Standard | 11.75a | 14.75b | 0.0b | 0.0b | 0.0b | 0.25b | 0.0b |

At the 42-DAT evaluation a decline in the live mite and egg populations began to occur in the untreated check. However the population increased gain at the 60-DAT evaluation. Again, all of the treatments provided acceptable suppression and control of the mites and eggs through the 60-DAT evaluation. No plant phytotoxicity was observed to the almond trees during this experiment.

In summary, compared to untreated control, above results indicate that C13 can effectively control two-spotted spider mites.

Example 12

Control of Pacific Spider Mite in Peaches

Methods

A single application was made to single-tree plots in a peach orchard. The application followed the methods described in Example 11 (see Table 31 for details of all treatments).

TABLE 31

Treatments and Rates (3)

| Treatment # | Description | Rate |
|---|---|---|
| #1 | Untreated control (UTC) | |
| #2 | C13 | 2 qt/a |
| #3 | C13 | 3 qt/a |
| #4 | C13 | 4 qt/a |
| #5 | Standard (Acramite (Bifenazate)) | 1 qt/a |

Twenty-four leaves per tree were sampled for mites, beginning on 0-DAT. Additional evaluations were done 3-, 7-, 14-, 21-, and 28-DAT. After mites were brushed onto clear glass plates covered with mineral oil, counts of all physiological stages were made under a dissecting microscope of three sections per 12 section pie template, so mite counts are reported as the equivalent of per six leaves. When present, predators were counted and analyzed. All recorded predators in this trial were predatory mites, although there was the occasional thrip beginning with the 14-DAT evaluation.

Phytotoxicity was evaluated twice on 7-DAT and 14-DAT. A 0-10 scale was used, where 0=no phytotoxic effects on leaves and 10=100% of tree with total leaf damage.

Results

Tables 32 to 35 presents numbers of mite eggs per 24 leaves, numbers of mite juveniles per 24 leaves, numbers of mite adults per 24 leaves, and numbers of predators per 24 leaves, respectively, on each observation point. As they show, all of the treatments were providing good suppression of live mites, mite eggs, and predators. Additionally, all of the chemical treatments were statistically equal in their control and superior to the untreated check.

TABLE 32

Mean # of mite eggs per 24 leaves

| | 0 DAT | 3 DAT | 7 DAT | 14 DAT | 21 DAT | 28 DAT |
|---|---|---|---|---|---|---|
| #1 Untreated | 9.0a | 14.0a | 17.0a | 14.3a | 12.3a | 10.5a |
| #2 C13 | 6.3ab | 2.0b | 0.0b | 0.8b | 3.0b | 2.3b |
| #3 C13 | 5.0b | 1.8b | 1.0b | 0.5b | 0.8b | 6.3ab |
| #4 C13 | 6.0ab | 2.3b | 0.0b | 0.8b | 2.5b | 2.8b |
| #5 Standard | 6.5ab | 0.8b | 0.0b | 0.0b | 0.5b | 0.5b |

TABLE 33

Mean # of mite juveniles per 24 leaves

| | 0 DAT | 3 DAT | 7 DAT | 14 DAT | 21 DAT | 28 DAT |
|---|---|---|---|---|---|---|
| #1 Untreated | 8.8a | 16.0a | 20.0a | 22.5a | 16.8a | 13.8a |
| #2 C13 | 7.5a | 0.3b | 0.0b | 0.3b | 1.3b | 2.5b |
| #3 C13 | 6.3a | 0.8b | 1.5b | 0.8b | 0.0b | 4.3ab |
| #4 C13 | 6.5a | 1.8b | 0.3b | 0.0b | 1.8b | 2.3b |
| #5 Standard | 8.0a | 0.0b | 0.0b | 0.0b | 0.0b | 0.8b |

TABLE 34

Mean # of mite adults per 24 leaves

| | 0 DAT | 3 DAT | 7 DAT | 14 DAT | 21 DAT | 28 DAT |
|---|---|---|---|---|---|---|
| #1 Untreated | 4.3a | 6.5a | 13.3a | 12.3a | 10.8a | 10.0a |
| #2 C13 | 3.0ab | 0.3b | 0.0b | 0.3b | 1.0b | 2.5a |
| #3 C13 | 2.0ab | 0.8b | 1.0b | 0.0b | 0.5b | 6.3a |
| #4 C13 | 1.8b | 1.0b | 0.0b | 0.0b | 1.5b | 3.5a |
| #5 Standard | 3.3ab | 0.0b | 0.0b | 0.0b | 0.3b | 0.5a |

TABLE 35

Mean # of mite eggs per 24 leaves

| | 0 DAT | 3 DAT | 7 DAT | 14 DAT | 21 DAT | 28 DAT |
|---|---|---|---|---|---|---|
| #1 Untreated | 4.3a | 6.5a | 13.3a | 12.3a | 10.8a | 10.0a |
| #2 C13 | 3.0ab | 0.3b | 0.0b | 0.3b | 1.0b | 2.5a |
| #3 C13 | 2.0ab | 0.8b | 1.0b | 0.0b | 0.5b | 6.3a |
| #4 C13 | 1.8b | 1.0b | 0.0b | 0.0b | 1.5b | 3.5a |
| #5 Standard | 3.3ab | 0.0b | 0.0b | 0.0b | 0.3b | 0.5a |

In summary, compared to untreated control, above results indicate that C13 can very effectively control pacific spider mites.

Example 13

Control of Asian Citrus Psyllid

Methods

A single application was made to citrus trees. Each branch was sprayed with treatment solutions until run-off using a hand-held atomizer. Table 36 shows details of each treatment.

TABLE 36

Treatments and Rates (4)

| Treatment # | Description | Rate |
|---|---|---|
| #1 | Untreated control (UTC) | |
| #2 | C13 | 4 qt/a |
| #3 | C13 | 2 qt/a |
| #4 | Tank mix | (C13 2 qt/a + mineral oil 5 gal/a) |
| #5 | Standard (Danti 2.4EC (Fenpropathrin)) | 1 pt/a |

The adult Asian citrus psyllid (ACP) was evaluated by the tap method. Specifically, a branch from each sample citrus tree is tapped using a piece of PVC pipe to knock any psyllids present onto a board. The number of psyllids on the boards (as well as any other insects) is then recorded. The thrips were only counted once after application due to the drop of flower petals causing thrips to leave the citrus trees.

Results

Table 37 presents numbers of psyllid adults per branch of peach tree on each observation point.

TABLE 37

Mean numbers of psyllid adults per branch

| | 0 DAT | 3 DAT | 7 DAT | 21 DAT | 33 DAT | 49 DAT |
|---|---|---|---|---|---|---|
| #1 Untreated | 6.3a | 6.0a | 5.5b | 3.1a | 2.2a | 4.7a |
| #2 C13 | 7.7a | 3.1a | 2.2b | 3.6a | 1.8ab | 3.7a |

TABLE 37-continued

Mean numbers of psyllid adults per branch

|  | 0 DAT | 3 DAT | 7 DAT | 21 DAT | 33 DAT | 49 DAT |
|---|---|---|---|---|---|---|
| #3 C13 | 5.4a | 3.3a | 3.1b | 2.6a | 1.6ab | 5.2a |
| #4 Tank mix | 5.3a | 2.3a | 2.5b | 1.9a | 1.1ab | 4.1a |
| #5 Standard | 5.0a | 1.5a | 0.8b | 1.0a | 0.7b | 3.6a |

As it shows, at two days after treatment (DAT), all treatments had lower ACP adults numerically than the UTC. At 7 DAT, all treatments had significantly reduced the number of adult ACP from the UTC and Danitol numerically had the lowest number of adult ACP. AT 20 DAT, Danitol numerically had the lowest number of adult ACP and C13+oil was next lowest. The same trend held true at 33 DAT. At 49 DAT, all plots were equal to the UTC.

Figure 6:
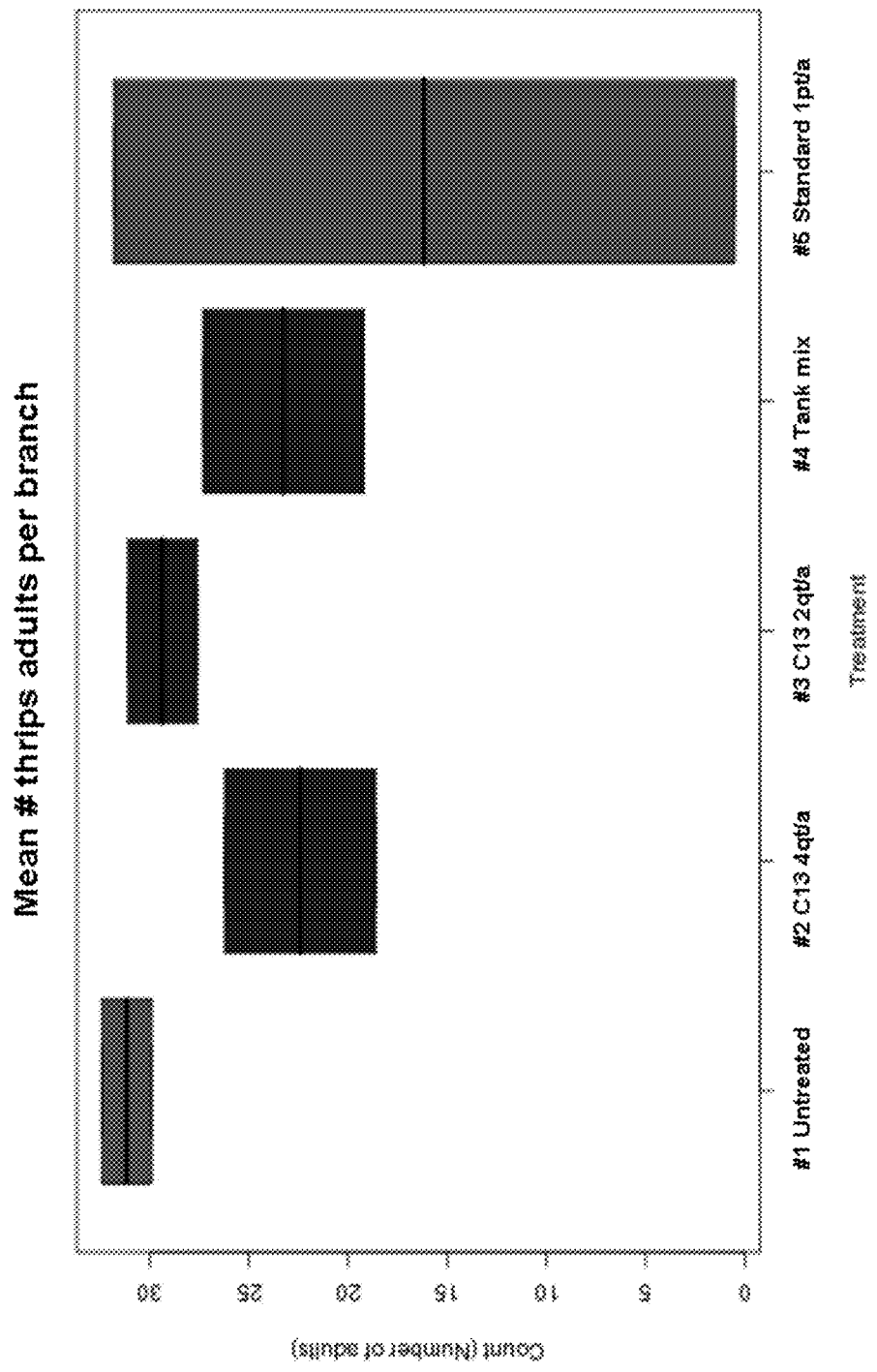
FIG. 6 depicts number of *thrips* in each treatment, wherein the colored bar shows the range of *thrips* and the bolded line presents the average number of *thrips* observed during the entire test.

FIG. 6 presents number of *thrips* in each treatment (colored bar shows the range of *thrips* and the bolded line presents the average number of *thrips* observed during the entire test). Danitol gave better control of flower *thrips* than C13. The high rate of C13 and C13+oil gave better control of *thrips* than the low rate of C13 alone. There was no phytotoxicity to the orange trees in this trial.

Example 14

Control of Chilli *Thrips* in Peppers

Methods

'Jalapeno' pepper transplants were set 12 in. apart on 8-in. high and 72-in. wide beds of Rockdale soil. The beds were fumigated two weeks prior to setting transplants with a mixture containing 67% methyl bromide and 33% chloropicrin at 220 lbs/acre. The beds were supplied with drip irrigation lines and covered with 1.5-mil thick black polyethylene mulch. Pepper plants were irrigated twice daily using a drip system. Fertilizer (N-P-K mix) was applied at 200-50-240 lb. per acre. To control weeds trifluralin (Treflan EC, 24 lbs. [product]/A) was used once 10 d before planting, supplemented during the middle of the season with mechanical cultivation.

Treatment plots consisted of 2 beds, each 30 ft. long and 6 ft. wide. Treatments evaluated in this study were shown in Table 38 below:

TABLE 38

Treatments and rates (5)

| Treatment | Rate/acre |
|---|---|
| Control | N/A |
| C13 | 4.0 qt |
| C13 followed by | 2.0 qt |
| Radiant | 7.0 oz |
| Radiant followed by | 7.0 oz |
| C13 | 2.0 qt |
| Radiant | 7.0 oz |

Radiant is a commercial pesticide, containing: 11.7% active compounds (mixture of 1H-as-Indaceno[3,2-d]oxacyclododecin-7,15-dione, 2-[(6-deoxy-3-O-ehtyl-2,4-di-O-methyl-a-L-mannopyranosyl)oxy]-13-[[(2R,5S,6R)-5-(dimethylamino)-tetrahydro-6-methyl-2H-pyran-2yl]oxy]-9-ethyl-, (2R, 3aR, 5aR, 5bS, 9S,13S, 14R, 16aS,16bR) and 1H-as-Indaceno[3,2-d]oxyacyclododecin,7,15-dione,2-[(6-deoxy-3-O-ethyl-2,4-di-O-methyl-a-L-manno-pyranosyl)oxy]-13-[[(2R, 5S, 6R)-5-(dimethylamino) tetrahydro-6methyl-2H-pyran-2yl]oxy]-9-ehtyl-2, 3, 3a, 5a, 5b, 6,9,10, 11,12,13,14, 16a, 16b-tetradecahydro-4,14-dimethyl-, (2S, 3aR, 5aS, 5bS, 9S, 13S, 14R, 16aS, 16bS), and 88.3% other inactive ingredients.

Treatments were arranged in a randomized complete block design with four replications. A non planted 5 feet area separated each replication. Treatments were applied on foliage by using a $CO_2$ backpack sprayer delivering 70 gpa at 30 psi. Application of all treatments was made on four dates—day 0, day 7, day 14, and day 21. Evaluation of treatments was made 48 h after each application on day 2, day 9, day 16, and day 23 by randomly selecting 10 leaves, one leaf/plant, from each treatment plot. Leaves were placed in a ziplock bag and transported to the laboratory. The leaves were then washed with 70% alcohol to separate chilli *thrips* and to record the numbers of adults and larvae.

Results

C13 alone reduced chilli *thrips* larvae on 'Jalapeno' pepper when compared with the nontreated control (Table 39).

TABLE 39

Mean number of larvae/10 leaf sample

| Treatment | Rate/acre | Day 2 | Day 9 | Day 16 | Day 23 | Mean |
|---|---|---|---|---|---|---|
| Control |  | 5.44a | 6.50a | 6.81a | 5.56a | 6.07a |
| C13 | 4.0 qt | 4.69a | 3.69b | 2.25b | 1.19b | 2.95b |
| C13 followed by Radiant | 2.0 qt 7.0 oz | 4.94a | 0.00c | 0.25c | 0.06c | 1.31c |
| Radiant followed by C13 | 7.0 oz 2.0 qt | 0.12b | 0.31c | 0.06c | 0.25c | 0.19d |
| Radiant | 7.0 oz | 0.06b | 0.19c | 0.00c | 0.00c | 0.00d |

Means within a column followed by a similar letter(s) do not differ significantly ($P > 0.05$; DMRT).

Use of C13 in rotation with Radiant further reduced the mean numbers of chilli *thrips* larvae when compared with C13 alone. Mean number of adults in C13 treated plants did not differ from nontreated control (Table 40). However, C13 in rotation with Radiant provided significant reduction of chilli *thrips* adults when compared with the nontreated control. A management program with Radiant followed by C13 did provide better reduction of chilli *thrips* larvae and adults than C13 followed by Radiant.

TABLE 40

Mean number of chilli thrips adults/10 leaf sample of 'Jalapeno' treated with various Treatments

| Treatment | Rate/acre | Day 2 | Day 9 | Day 16 | Day 23 | Mean |
|---|---|---|---|---|---|---|
| Control |  | 1.87a | 2.50a | 1.87a | 0.81a | 1.77a |
| C13 | 4.0 qt | 2.69a | 1.62a | 1.12b | 0.81a | 1.56a |
| C13 followed by Radiant | 2.0 qt 7.0 oz | 2.25a | 0.06b | 0.37c | 0.00b | 0.67b |
| Radiant followed by C13 | 7.0 oz 2.0 qt | 0.18b | 0.25b | 0.12c | 0.12b | 0.17c |
| Radiant | 7.0 oz | 0.06b | 0.12b | 0.00c | 0.00b | 0.05c |

Means within a column followed by a similar letter(s) do not differ significantly ($P > 0.05$; DMRT).

Mean numbers of marketable fruits were significantly higher on all treated plants than the nontreated plants (Table 41). Radiant treated plants had the highest number of fruits among all treatments.

TABLE 41

Mean numbers of marketable fruits/plant of 'Jalapeno' pepper treated with various insecticides

| Treatment | Rate/acre | Day 2 | Day 9 | Day 16 | Day 23 | Mean |
|---|---|---|---|---|---|---|
| Control | | 6.31b | 6.75c | 5.37c | 5.25c | 5.92d |
| C13 | 4.0 qt | 8.06ab | 7.87b | 4.94c | 6.50b | 6.84c |
| C13 followed by Radiant | 2.0 qt 7.0 oz | 7.62ab | 8.19ab | 6.94b | 7.06ab | 7.45bc |
| Radiant followed by C13 | 7.0 oz 2.0 qt | 8.25a | 8.25ab | 6.56b | 7.06ab | 7.53b |
| Radiant | 7.0 oz | 9.06a | 9.31a | 8.06a | 8.25a | 8.67a |

Means within a column followed by a similar letter(s) do not differ significantly (P > 0.05; DMRT).

Mean number of *O. insidiosus*/Jalapeno' pepper did not differ among treatments (Table 42). Both C13 and Radiant did not have any adverse effect on *O. insidiosus* when compared with the nontreated control.

TABLE 42

Mean number of *Orius insidiosus*/plant of 'Jalapeno' pepper treated with various insecticide treatments

| Treatment | Rate/acre | Day 2 | Day 9 | Day 16 | Day 23 | Mean |
|---|---|---|---|---|---|---|
| Control | | 0.19a | 0.12a | 0.06a | 0.12a | 0.12a |
| C13 | 4.0 qt | 0.62a | 0.19a | 0.19a | 0.12a | 0.28a |
| C13 followed by Radiant | 2.0 qt 7.0 oz | 0.25a | 0.19a | 0.12a | 0.06a | 0.16a |
| Radiant followed by C13 | 7.0 oz 2.0 qt | 0.12a | 0.12a | 0.06a | 0.06a | 0.09a |
| Radiant | 7.0 oz | 0.06a | 0.12a | 0.12a | 0.00a | 0.08a |

Means within a column followed by a similar letter(s) do not differ significantly (P > 0.05; DMRT).

Example 15

Control of Whitefly in Melon

Methods

The trial was conducted in west United States. Honeydew melon (variety: Greenbflesh) seedlings were transplanted into wet Holtville silty clay. Treatments were arranged in a randomized complete lock design with 4 replicates. Each plot had a size of 50'×13.3' (2 beds/plot, and one buffer bed between plots 10' buffer between blocks). Plots were irrigated very week. Herbicide (ProwlH2) was applied at a rate of 3 pt/acre.

Pesticides were applied using five TJ-60 11003VS bizzkes per bed (PSI:40, GPA: 53.42) on day 0, day 14, and day 22. Details of treatments are shown in Table 43 below. On day 0, eggs, nymphs, and adults whiteflies were counted.

TABLE 43

Treatments and rates (6)

| Treatment | Oz/acre | ml/4 gal | Application date | Plot #'s (FIG. 42) |
|---|---|---|---|---|
| 1. Untreated | — | — | — | 6, 21, 30, 54 |
| 2. Movento | 3.0 | 6.6 | day 1, day 15, and day 23 | 1, 17, 37, 46 |
| 3. Movento | 5.0 | 11.1 | day 1, day 15, and day 23 | 4, 26, 31, 56 |
| 4. Oberon 2SC | 7.0 | 15.5 | day 1, day 15, and day 23 | 13, 19, 32, 43 |
| 5. Oberon 2SC | 8.5 | 18.8 | day 1, day 15, and day 23 | 10, 22, 39, 44 |
| 6. Oberon 2SC fb C14 fb | 7.0 fb 64.0 | 15.5 f/b 141.5 | day 1 day 15 and day 23 | 7, 15, 33, 53 |
| 7. C14 | 64.0 | 141.5 | day 1, day 15, and day 23 | 12, 24, 29, 55 |
| 8. C14 | 96.0 | 212.3 | day 1, day 15, and day 23 | 3, 18, 40, 48 |
| 9. Venom 20 SG | 14.32 | 30.4 gm | day 1, day 15, and day 23 | 5, 28, 41, 51 |
| 10. Esteem 0.86 EC | 9.84 | 21.8 | day 1, day 15, and day 23 | 9, 20, 38, 49 |
| 11. Knack 0.86 EC | 9.84 | 21.8 | day 1, day 15, and day 23 | 8, 25, 36, 45 |
| 12. NNI-1010 20SC | 3.2 | 7.1 | day 1, day 15, and day 23 | 2, 27, 34, 50 |
| 13. NAI-2302 15 EC | 27.0 | 59.7 | day 1, day 15, and day 23 | 14, 16, 35, 52 |
| 14. NNI-0871 SC | 17.0 | 37.6 | day 1, day 15, and day 23 | 11, 23, 42, 47 |

*NIS @ 0.25% (37.9 ml/4 gal) was added to all spray mixtures.

**C14 comprises 25% Cl (Table 1) plus 35% vegetable oil carrier and 40% other carrier/solvent, emulsifier, and/or spreader/binder Results Whitefly adults were inoculated on the 5$^{th}$ leaf form cane tip on 10 plants per plots. Whitefly eggs, nymphs, and adults were counted (eggs and nymphs from a 1.65 cm$^2$ disk were counted), 10 leaves from each plot. Samples were taken and counted on day 0, day 5, day 8, day 14, day 19, day 22, day 29, and day 34. Tables 43 to 45 show the mean results. As the data indicates, plants sprayed with C14 had reduced whitefly eggs, nymphs, and adults, compared to untreated plants. In addition, combination of C14 with other pesticide, Oberon (23.1% spiromesifen, 10% trade secret ingredients), further reduced the whitefly eggs, nymphs, and adults population, indicating a synergistic effect.

TABLE 44

Silverleaf Whitefly Eggs per 16.5 cm$^2$ of Melon Leaf Following Various Insecticides (mean results)

| Treatment | Oz/acre | Day 0 | Day 5 | Day 8 | Day 14 | Day 19 | Day 22 | Day 29 | Day 34 | PTA[y,z] |
|---|---|---|---|---|---|---|---|---|---|---|
| Untreated | — | 92.50 | 63.00 abc | 75.25 | 1.74 a | 24.50 | 22.75 ab | 13.25 | 10.75 | 38.14 a |
| Movento | 3.0 | 71.00 | 59.00 abcd | 32.25 | 1.06 e | 14.75 | 16.25 abcd | 7.25 | 6.75 | 21.00 d |
| Movento | 5.0 | 68.75 | 54.25 abcd | 38.75 | 1.18 de | 22.25 | 7.00 e | 7.50 | 6.75 | 21.82 cd |
| Oberon 2SC | 7.0 | 59.75 | 80.75 a | 54.75 | 1.16 de | 19.00 | 9.75 de | 6.00 | 4.25 | 27.21 bcd |
| Oberon 2SC | 8.5 | 44.75 | 40.25 bcd | 40.75 | 1.26 cde | 13.50 | 10.75 de | 5.75 | 4.25 | 19.57 d |
| Oberon 2SC fb C14 fb | 7.0 fb 64.0 | 56.50 | 33.75 cd | 50.50 | 1.22 cde | 10.25 | 15.25 abcde | 7.50 | 6.25 | 19.89 d |
| C14 | 64.0 | 43.00 | 58.00 abcd | 54.25 | 1.52 abc | 23.00 | 10.75 de | 9.25 | 7.00 | 28.00 abcd |
| C14 | 96.0 | 67.00 | 79.50 a | 51.25 | 1.63 ab | 23.50 | 13.50 cde | 9.00 | 8.25 | 32.89 ab |
| Venom 20 SG | 14.32 | 41.50 | 46.25 bcd | 47.50 | 1.27 cde | 22.75 | 13.75 bcde | 5.25 | 6.50 | 23.07 bcd |
| Esteem 0.86 EC | 9.84 | 56.75 | 47.75 bcd | 52.75 | 1.12 de | 23.50 | 23.00 a | 12.75 | 11.00 | 26.18 bcd |
| Knack 0.86 EC | 9.84 | 64.25 | 64.25 ab | 62.25 | 1.68 a | 18.50 | 20.00 abc | 8.00 | 4.75 | 32.14 abc |
| NNI-1010 20SC | 3.2 | 64.00 | 57.25 abcd | 48.75 | 1.37 bcd | 23.00 | 9.50 de | 9.50 | 9.25 | 25.86 bcd |
| NAI-2302 15 EC | 27.0 | 80.50 | 32.25 d | 50.50 | 1.50 abc | 17.25 | 9.50 de | 12.85 | 11.05 | 24.33 bcd |
| NNI-0871 SC | 17.0 | 42.75 | 52.25 abcd | 33.25 | 1.20 de | 24.00 | 7.00 e | 10.75 | 10.50 | 22.00 cd |
|  |  | NS | LSD = 29.76 | NS | LSD = 0.30 | NS | LSD = 9.15 | NS | NS | LSD = 10.84 |

[y]Log transformed data used for analysis.
[z]PTA = post-treatment average.
Mean separations within columns by LSD$_{0.05}$.
NS = non-significant.

TABLE 45

Silverleaf Whitefly Nymphs per 16.5 cm$^2$ of Melon Leaf Following Various Insecticides (mean results)

| Treatment | Oz/acre | Day 0 | Day 5 | Day 8 | Day 14 | Day 19 | Day 22 | Day 29 | Day 34 | PTA[y,z] |
|---|---|---|---|---|---|---|---|---|---|---|
| Untreated | — | 19.25 | 42.75 | 188.25 a | 117.25 a | 63.50 a | 1.72 a | 1.52 a | 1.50 a | 76.64 a |
| Movento | 3.0 | 21.25 | 60.75 | 73.00 b | 47.75 cde | 27.25 cde | 1.27 c | 1.08 cd | 1.21 abcd | 36.86 cd |
| Movento | 5.0 | 27.25 | 41.50 | 96.50 b | 32.50 e | 18.75 e | 1.29 bc | 0.86 d | 1.12 cd | 32.50 d |
| Oberon 2SC | 7.0 | 29.75 | 55.50 | 108.50 b | 36.00 e | 47.25 abc | 1.12 c | 1.05 cd | 1.05 cd | 40.39 bcd |
| Oberon 2SC | 8.5 | 26.75 | 36.75 | 82.00 b | 56.75 bcde | 34.25 bcde | 1.10 c | 1.07 cd | 0.98 d | 35.36 cd |
| Oberon 2SC fb C14 fb | 7.0 fb 64.0 | 19.75 | 25.50 | 86.25 b | 31.00 e | 40.75 bcd | 1.27 c | 1.31 abc | 1.23 abcd | 34.36 cd |
| C14 | 64.0 | 11.00 | 38.75 | 83.75 b | 69.75 bcd | 34.00 bcde | 1.40 abc | 1.32 abc | 1.18 bcd | 41.75 bcd |
| C14 | 96.0 | 25.25 | 44.50 | 120.75 b | 81.00 b | 48.50 abc | 1.49 abc | 1.32 abc | 1.28 abcd | 53.21 b |
| Venom 20 SG | 14.32 | 15.00 | 40.50 | 79.00 b | 36.00 e | 20.75 de | 1.20 c | 1.17 bcd | 1.03 cd | 31.11 d |
| Esteem 0.86 EC | 9.84 | 22.50 | 43.50 | 104.50 b | 38.75 de | 36.50 bcde | 1.29 bc | 1.47 ab | 1.45 ab | 43.29 bcd |
| Knack 0.86 EC | 9.84 | 20.50 | 65.00 | 94.25 b | 43.25 cde | 32.25 bcde | 1.67 ab | 1.18 abcd | 1.28 abcd | 46.43 bc |
| NNI-1010 20SC | 3.2 | 27.50 | 45.50 | 62.50 b | 59.50 bcde | 54.00 ab | 1.10 c | 1.20 abcd | 1.08 cd | 39.14 bcd |
| NAI-2302 15 EC | 27.0 | 23.25 | 41.50 | 80.25 b | 72.00 bc | 33.75 bcde | 1.14 c | 1.25 abc | 1.34 abc | 41.89 bcd |
| NNI-0871 SC | 17.0 | 16.50 | 46.75 | 85.00 b | 43.75 cde | 34.75 bcde | 1.30 bc | 1.49 ab | 1.32 abc | 41.14 bcd |
|  |  | NS | NS | LSD = 59.33 | LSD = 32.32 | LSD = 21.87 | LSD = 0.40 | LSD = 0.34 | LSD = 0.31 | LSD = 14.76 |

[y]Log transformed data used for analysis.
[z]PTA = post-treatment average.
Mean separations within columns by LSD$_{0.05}$.
NS = non-significant.

TABLE 46

Adult Silverleaf Whitefly per Melon Leaf Following Various Insecticides (mean results)

| Treatment | Oz/acre | Day 0 | Day 5 | Day 8 | Day 14 | Day 19 | Day 22 | Day 29 | Day 34 | PTA[y,z] |
|---|---|---|---|---|---|---|---|---|---|---|
| Untreated | — | 6.20 | 13.93 a | 8.85 a | 3.83 | 9.55 a | 6.70 | 7.68 | 8.18 | 0.94 a |
| Movento | 3.0 | 9.00 | 2.50 cd | 1.80 bc | 1.35 | 4.53 b | 4.53 | 5.50 | 4.75 | 0.65 bc |
| Movento | 5.0 | 8.18 | 2.73 cd | 1.80 bc | 1.33 | 2.50 b | 3.40 | 3.78 | 3.05 | 0.54 bc |
| Oberon 2SC | 7.0 | 7.65 | 4.25 bcd | 2.72 bc | 2.45 | 3.68 b | 1.98 | 2.40 | 2.20 | 0.58 bc |

TABLE 46-continued

Adult Silverleaf Whitefly per Melon Leaf Following Various Insecticides (mean results)

| Treatment | Oz/acre | Day 0 | Day 5 | Day 8 | Day 14 | Day 19 | Day 22 | Day 29 | Day 34 | PTA$_{y,z}$ |
|---|---|---|---|---|---|---|---|---|---|---|
| Oberon 2SC | 8.5 | 7.10 | 2.95 cd | 1.65 bc | 1.53 | 3.30 b | 2.90 | 2.75 | 3.08 | 0.54 bc |
| Oberon 2SC fb | 7.0 fb | 7.83 | 3.28 cd | 2.78 bc | 1.00 | 3.45 b | 3.55 | 3.93 | 3.58 | 0.59 bc |
| C14 fb | 64.0 | | | | | | | | | |
| C14 | 64.0 | 7.20 | 4.45 bc | 3.20 bc | 2.53 | 3.65 b | 3.35 | 3.78 | 3.28 | 0.65 bc |
| C14 | 96.0 | 6.78 | 4.43 bc | 4.33 b | 2.55 | 4.20 b | 2.52 | 5.20 | 5.03 | 0.66 b |
| Venom 20 SG | 14.32 | 8.38 | 2.40 cd | 1.28 c | 0.78 | 5.25 b | 3.73 | 3.18 | 3.53 | 0.58 bc |
| Esteem 0.86 EC | 9.84 | 7.55 | 3.48 bcd | 2.33 bc | 2.03 | 3.90 b | 4.38 | 3.70 | 3.95 | 0.64 bc |
| Knack 0.86 EC | 9.84 | 8.48 | 4.20 bcd | 3.23 bc | 1.63 | 5.08 b | 3.28 | 3.83 | 3.75 | 0.66 b |
| NNI-1010 20SC | 3.2 | 8.75 | 2.00 d | 1.68 bc | 1.53 | 2.33 b | 1.18 | 2.70 | 2.23 | 0.47 c |
| NAI-2302 15 EC | 27.0 | 5.88 | 2.93 cd | 2.28 bc | 1.78 | 3.53 b | 2.66 | 3.78 | 4.67 | 0.64 bc |
| NNI-0871 SC | 17.0 | 8.20 | 5.55 b | 2.38 bc | 1.40 | 2.58 b | 1.98 | 2.00 | 2.35 | 0.55 bc |
| | | NS | LSD = 2.26 | LSD = 2.86 | NS | LSD = 3.46 | NS | NS | NS | LSD = 0.18 |

$^y$Log transformed data used for analysis.
$^z$PTA = post-treatment average.
Mean separations within columns by LSD$_{0.05}$.
NS = non-significant.

Example 16

Comparison of Extract-Based Product to Synthetic Product

A study was conducted to show that *Chenopodium ambrosioides* near *ambrosioides* essential oil extract based products have similar, if not identical, performance characteristics in greenhouse and field trials when compared with the synthetic blend product, C14, which consists of 25% C1+35% carrier (vegetable oil) and 40% other inerts (carrier, solvent, emulsifiier, and spreader/binder). The *Chenopodium ambrosioides* near *ambrosioides* extract-based products, referred to in this Example as C12, contains 25% C2 and 75% inerts (carrier, solvent, emulsifiier, and spreader/binder), as shown in Table 4. The actives in the extract-based product are 9-11.5% alpha-terpinene, 3.5-4.5% p-cymene, 2.5-3.5% d-limonene and minor terpenes and extract impurities in an amount that brings the total active to 25%. A range of percentages is given because the product tested was obtained from various lots of extract, and extract composition varies depending on climate, soil conditions and other factors. Inerts (carrier, solvent, emulsifiier, and spreader/binder) in C12 and C14 were identical. Greenhouse trials to evaluate plant sensitivity showed that the plant response to both C12 and C14 was virtually identical with neither material being injurious to plants when applied at twice the recommended label rate. In efficacy trials the recommended label rate (described below) of both C12 and C14 provided similar control of mites, *thrips* and mealybugs. In field trials, both C12 and C14 provided similar control of *thrips*, aphids and mites when applied at the same rate. No plant phytotoxicity effects were observed in the field trials. No material differences in performance were observed between C12 and C14.

Materials and Methods

Greenhouse and field applications of pesticides are conducted differently. In the greenhouse materials are normally applied as a % spray solution or a given amount of material per 100 gallons of spray solution. In these trials materials were applied with either a manual, hand-held trigger sprayer or with a $CO_2$ powered sprayer. Both methods achieved the desired result. C12 and C14 were compared at different spray concentrations for plant effects and efficacy. In the plant effects trials in the greenhouse, materials were foliarly applied 1-3 times at seven day intervals followed by a 4th soil drench application.

The traditional commercial greenhouse/nursery rating system for salability employs a 1 to 5 rating scale and generally reflects the overall condition of the entire plant. However, the whole plant rating system has limitations when applied to flowering plants. The 1-5 rating system employed in this report is for flowering plants and has two rating aspects—one for foliage and one for flowers. An explanation for each is given below.

Foliage
1=Robust plant;
2=slight stunting, distortion and/or chlorosis;
3=moderate stunting, distortion and/or chlorosis;
4=severe stunting, distortion and/or chlorosis;
5=dead or moribund.

Flowers
1=Flowers robust and well-formed;
2=slight stunting, distortion and/or discoloration;
3=moderate to severe stunting, distortion and/or discoloration;
4=Flowers fail to emerge from buds;
5=no flower buds.

Rating system 3 (Top Grade) below is an additional rating scheme. Unlike the other phytotoxicity ratings, in Top Grade the higher the number the better the plant. It is a rating scheme developed by plant pathologist, Dr. A. R. Chase, of Chase Research.

Top Grade
1=plant dead, unsalable;
2=poor, unsalable;
3=moderate, salable;
4=good, salable;
5=excellent, salable.

In the field trials materials were applied with $CO_2$ powered sprayers with a straight boom of spray nozzles, directly over the top of the plant or in a configuration to conform to plant. In each case researchers employed an array of commonly used flat fan nozzles. Spray solutions were applied at 30 gallons per acre (GPA) in 3 trials and 100 GPA for the 4$^{th}$. C12 and C14 were each applied at 2 pts per acre. Materials were applied 1-5 times in the field trials.

Results and Discussion

The two plant effects trials in the greenhouse employed C14 at 4, 8 and 16 quarts/100 gallons of spray solution (=1%, 2% and 4%, respectively). C12 was applied at 8 qts (2× the maximum recommended label rate). In one set of trials materials were foliarly applied three times to a variety of bedding plants with a soil drench as the fourth application. In another set of trials materials were applied foliarly three to four times. Evaluations were taken 8-9 days after the last application. The 4 qt spray solution is the maximum label rate for greenhouse applications. In no case did plants display significant phytotoxic effects at the 8 qt/100 gallon rate of 400 or 416.

There were no plant effects from any treatment after 3 foliar applications. Ratings were taken 8 days after a soil drench application.

Two greenhouse efficacy trials were conducted. In one trial on two spotted spider mites, a 1% solution of each material resulted in C12 providing greater numerical control of mites 7 days after treatment (DAT), but C14 providing better control at 14 DAT. Based on mite counts, there were no significant differences (P=0.05) among treatments.

In a second greenhouse trial C12 and C14 were applied at 1% solutions for control of the Madeira mealybug. The C14 treatment started with a higher number of crawlers/plant than C12 (45.4 vs. 21.3). There were numerical, but not significant differences in activity between C12 and C14 for control of mealybug crawlers. At 14 DAT4 both materials brought crawler numbers below that of the control.

Figure 7:
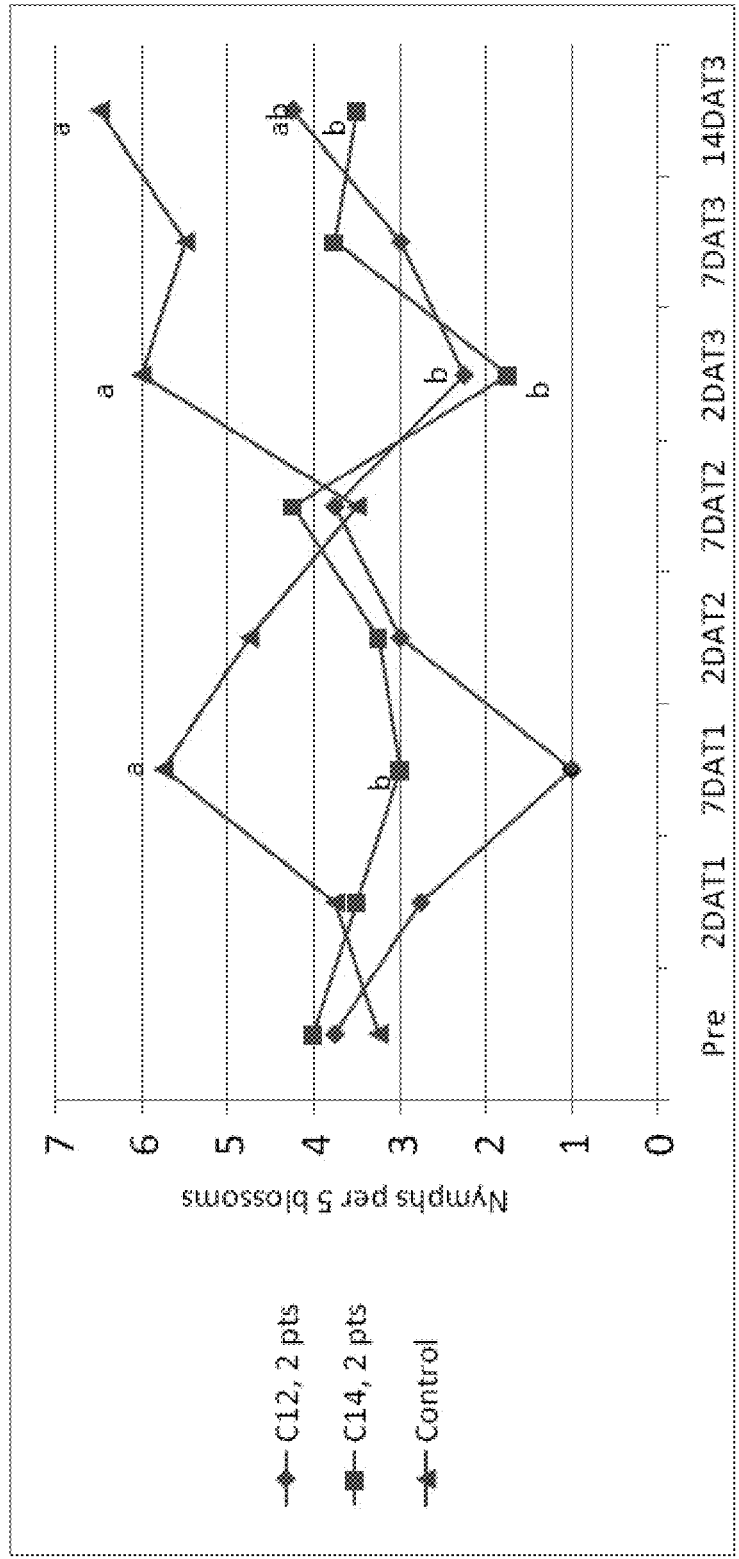
FIG. 7 depicts experimental results on control of Western Flower *Thrips* (*Frankliniella occidentalis*) on Peppers with C12 and C14. Hughson, Calif. Material applied with a CO2 sprayer employing three 8003 flat fan nozzles per row, operating at 30 psi and 30 GPA. Evaluation points with the same letter are not significantly different at P=0.05.
Figure 8:
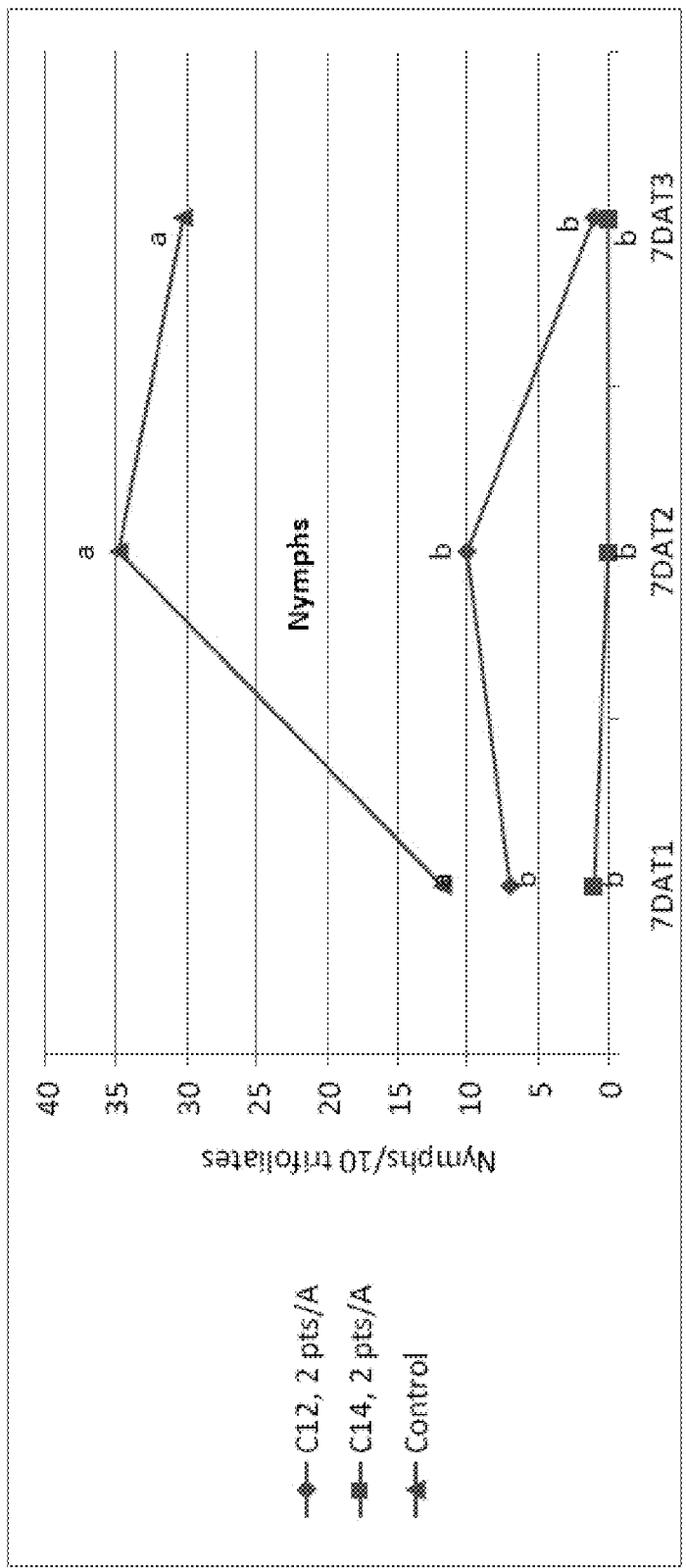
FIG. 8 depicts experimental results on control of Melon Aphid Nymphs (*Aphis gossypii*) on Tomatoes with C12 and C14. Ripon, Calif. Materials applied with a CO2 sprayer employing 8003 flat fan nozzles operating at 40 psi and 30 GPA. Evaluation points with the same letter are not significantly different at P=0.05.
Figure 9:
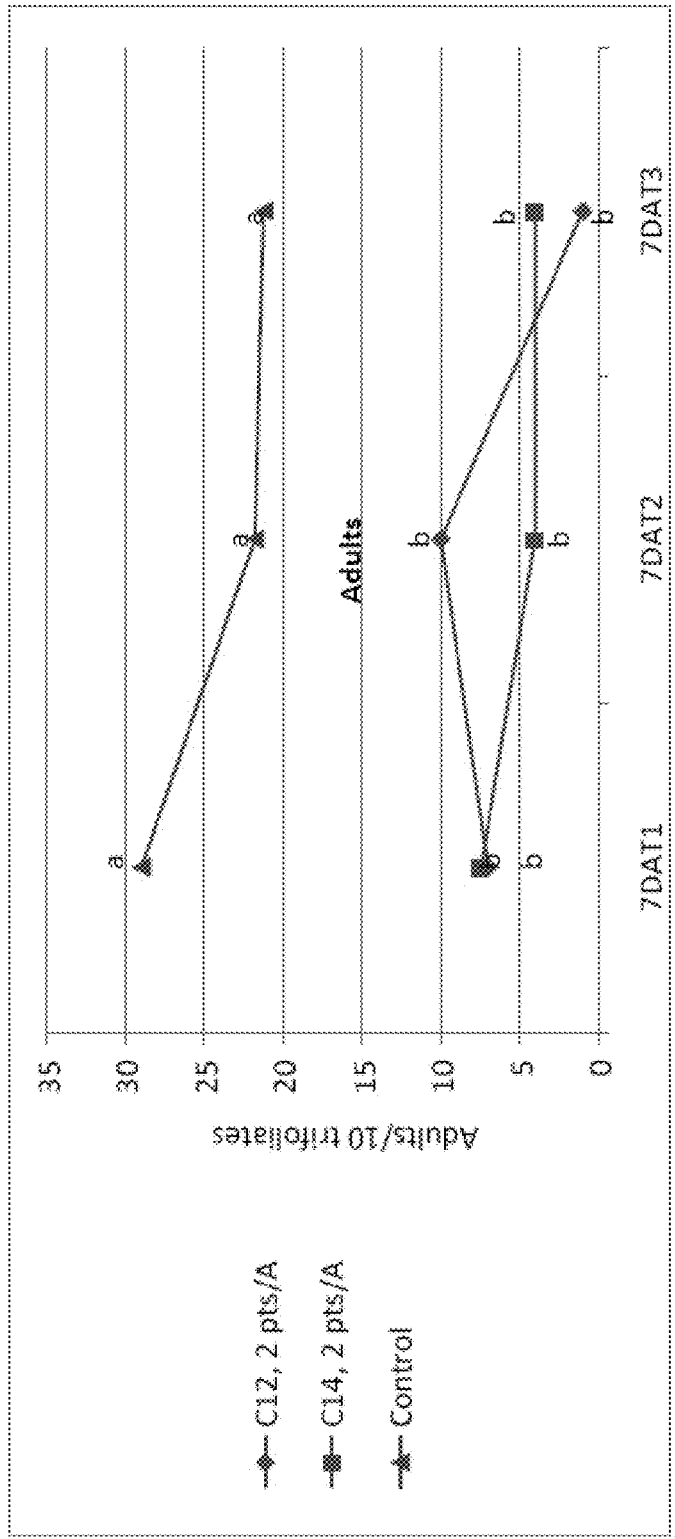
FIG. 9 depicts experimental results on control of Melon Aphid Adults (*Aphis gossypii*) on Tomatoes with C12 and C14. Ripon, Calif. Materials applied with a CO2 sprayer employing 8003 flat fan nozzles operating at 40 psi and 30 GPA. Evaluation points with the same letter are not significantly different at P=0.05.

Four trials were conducted in the field; one each with *thrips* and aphids, and two with mites. In the *thrips* trial on peppers, 2 pts/acre each of C12 and C14 performed numerically similar throughout the test period (FIG. 7). Only one evaluation event resulted in a significant difference in performance; Nymphs/5 blossoms at 7 DAT1 where C12 and C14 averaged 3 and 1, respectively. In the melon aphid trial on tomatoes the 2 pt/acre rates of both materials performed similarly; each significantly reducing aphid nymphs (FIG. 8) and adults (FIG. 9) below that of the control.

Figure 10:
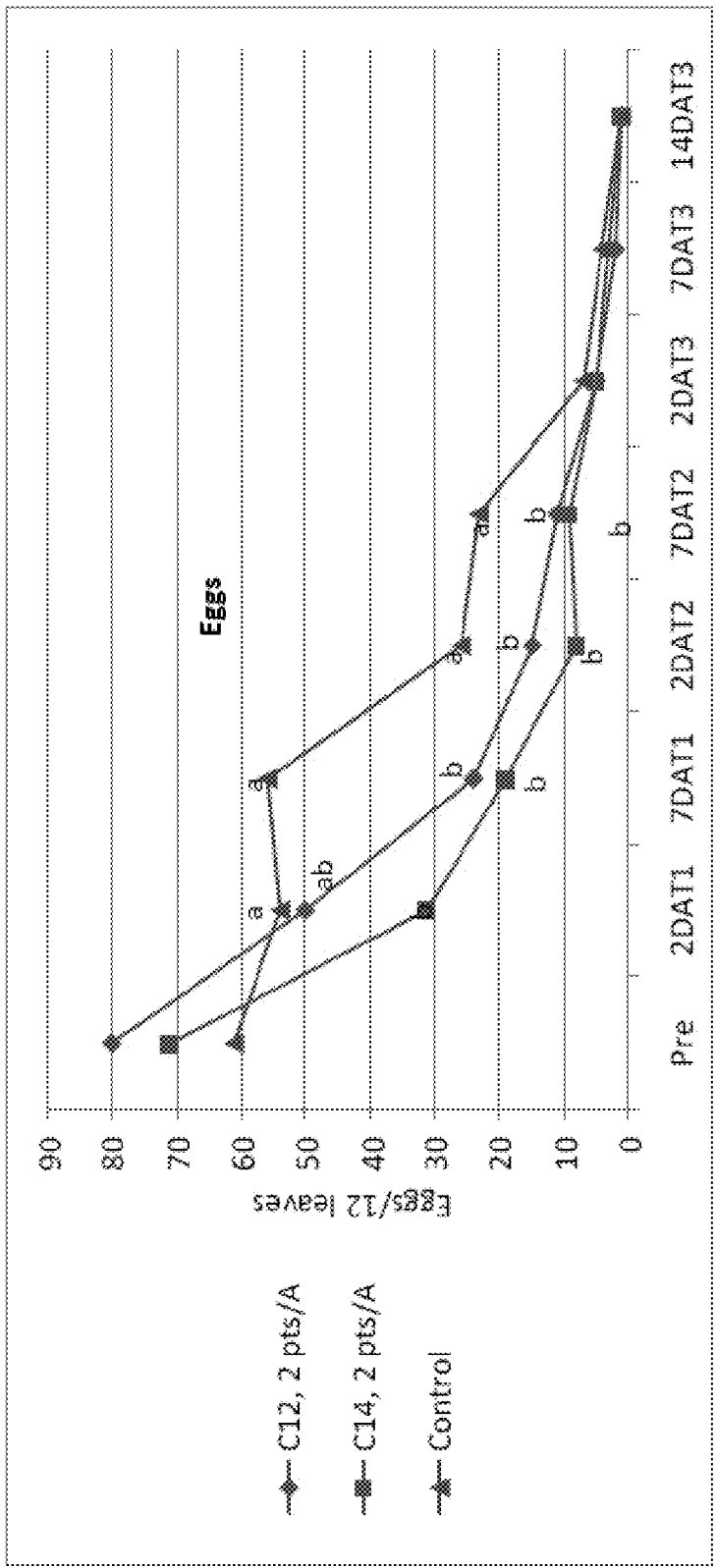
FIG. 10 depicts experimental results on control of Two Spotted Spider Mite Eggs (*Tetranychus urticae*) on Cotton with C12 and C14. Hughson, Calif. Materials applied with a CO2 sprayer employing three 8002 flat fan nozzles per row, operating at 30 psi and 30 GPA. Evaluation points with the same letter are not significantly different at P=0.05.
Figure 11:
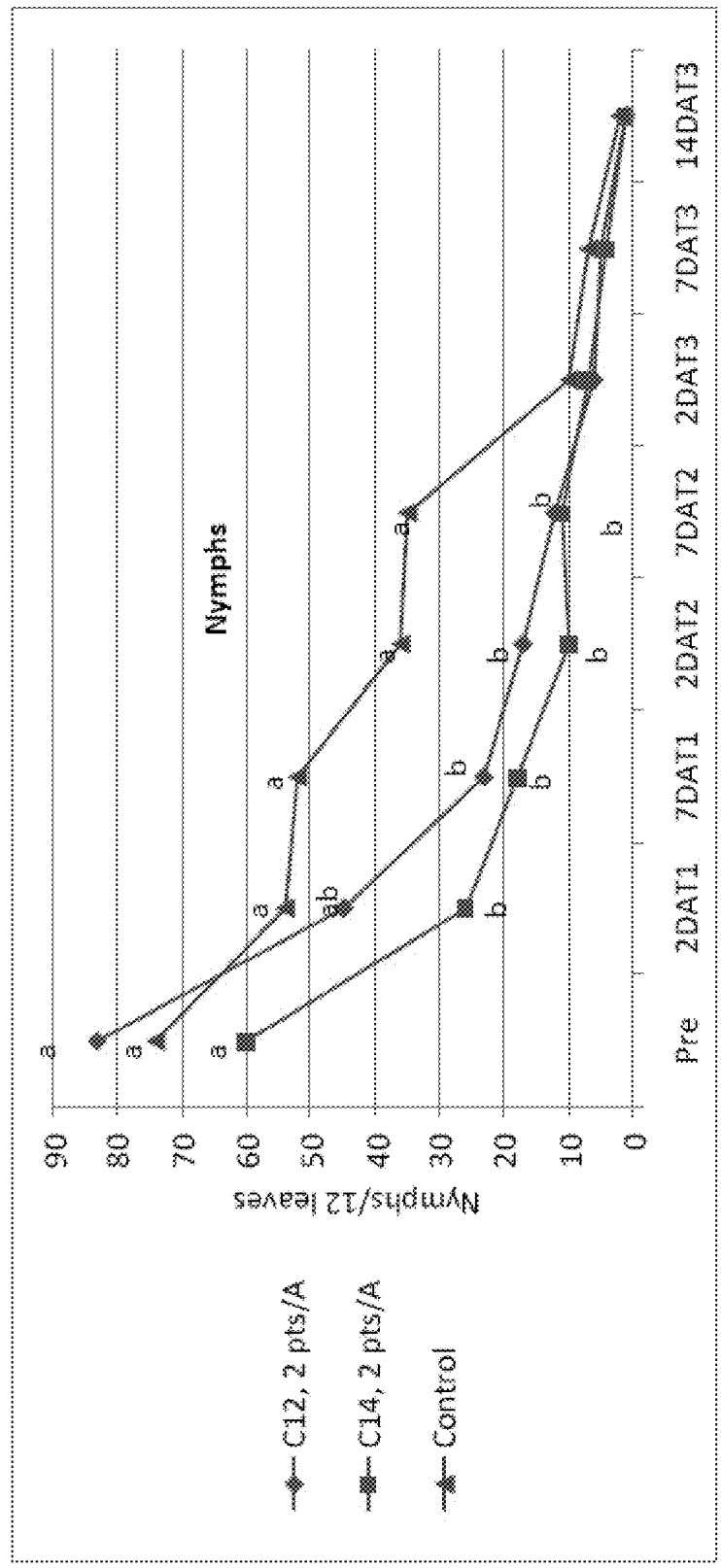
FIG. 11 depicts experimental results on control of Two Spotted Spider Mite Nymphs (*Tetranychus urticae*) on Cotton with C12 and C14. Hughson, Calif. Materials applied with a CO2 sprayer employing three 8002 flat fan nozzles per row, operating at 30 psi and 30 GPA. Evaluation points with the same letter are not significantly different at P=0.05.
Figure 12:
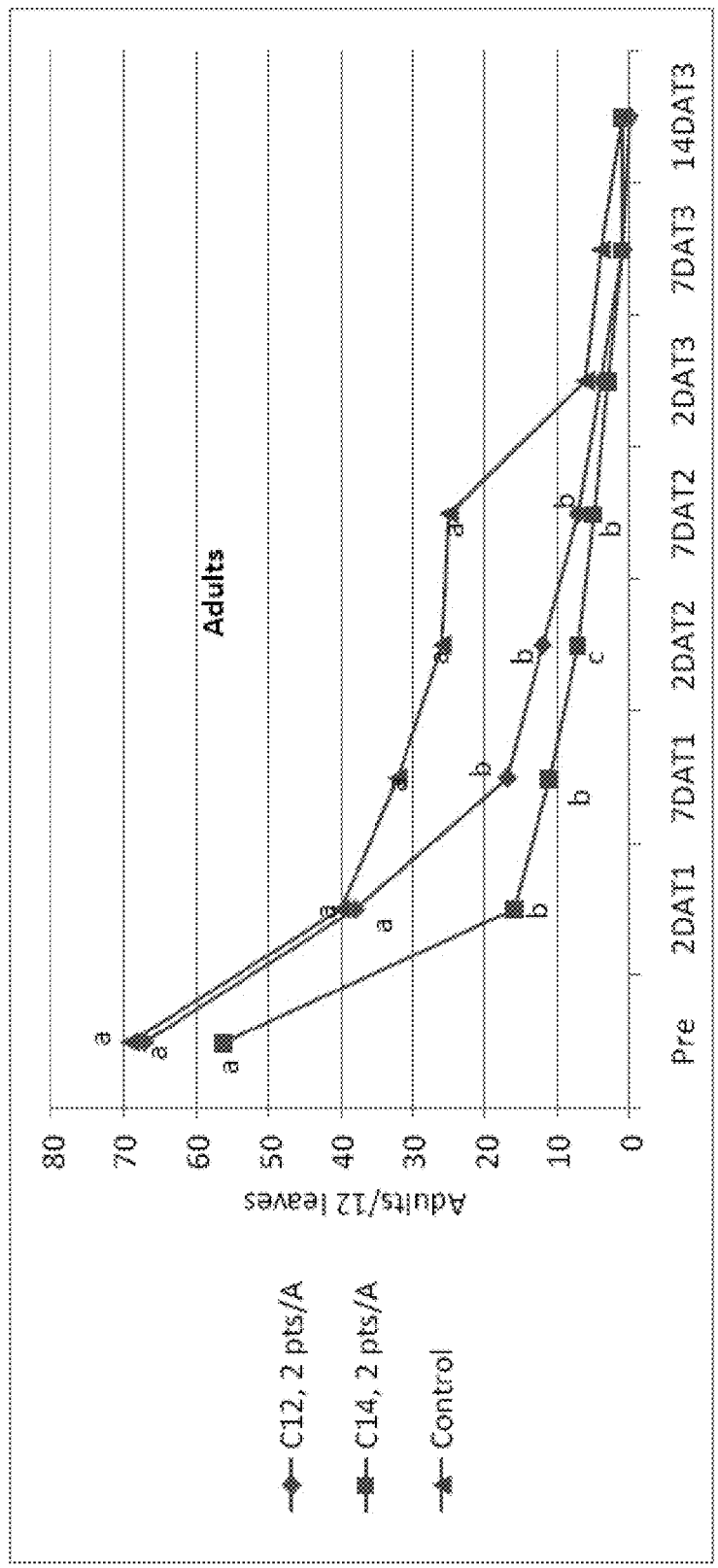
FIG. 12 depicts experimental results on control of Two Spotted Spider Mite Adults (*Tetranychus urticae*) on Cotton with C12 and C14. Hughson, Calif. Materials applied with a CO2 sprayer employing three 8002 flat fan nozzles per row, operating at 30 psi and 30 GPA. Evaluation points with the same letter are not significantly different at P=0.05.

In a mite trial on cotton all three life forms (eggs, nymphs and adults) were effectively controlled by both C12 and C14. Each provided significant reductions over the untreated control at most evaluation points throughout the trial (FIGS. 10, 11 and 12). On occasion a significant difference was revealed at some evaluation points between C12 and C14, but, in general they reduced mite numbers in similar fashion. In a second mite trial on eggplant the 2 pt/acre rates of C12 and C14 performed essentially the same, with counts of mite motils (nymphs and adults) being numerically similar at each evaluation interval.

In conclusion, greenhouse and field testing revealed no material differences in performance or plant safety between C12 and C14 when used at the same rates.

Example 17

Preventative Control of Spider Mites with Multiple Applications of C13

A 1% solution of C13 was applied to lima bean plants one, two, or three times at 5-day intervals. After the third application, each plant was infested with 10-15 adult female spider mites. Mites were counted on each plant and compared to untreated control plants 14 days after treatment (DAT).

Results

Figure 13:
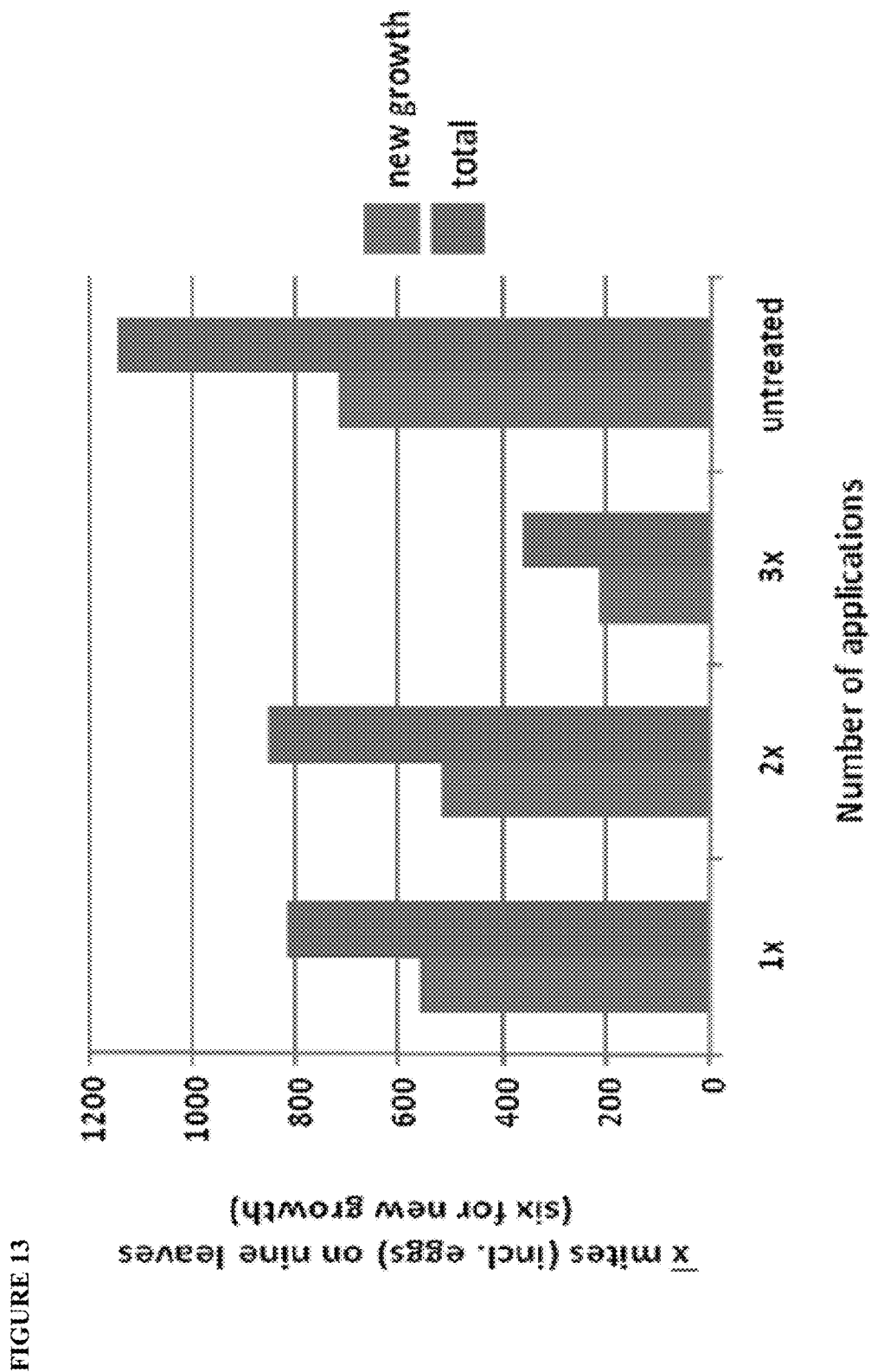
FIG. 13 depicts experimental results on preventative control of spider mites with multiple applications of C13.

The results are summarized in FIG. 13. One or two applications of C13 had a similar effect on the preventative control of the spider mite outbreak. A more robust effect was seen after three applications.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A spray formulation composition for controlling insects and/or mites consisting essentially of (i) a terpene blend consisting of substantially pure α-terpinene, substantially pure p-cymene and substantially pure limonene in a relative ratio of about 35-45:12-20:10-15, (ii) a carrier, and (iii) an adjuvant.

2. The composition of claim 1, wherein the carrier includes a vegetable oil.

3. The composition of claim 2, wherein the vegetable oil is canola oil.

4. The composition of claim 1, wherein the adjuvant includes an emulsifier.

5. The composition of claim 1, wherein the adjuvant includes a spreader-sticker.

6. The composition of claim 1, wherein the spray formulation is an emulsifiable concentrate.

7. The composition of claim 1, wherein the relative ratio is 40:15:12.

* * * * *